(12) United States Patent
Chinn et al.

(10) Patent No.: US 7,183,323 B2
(45) Date of Patent: Feb. 27, 2007

(54) SODIUM CHANNEL MODULATORS

(75) Inventors: Jason P. Chinn, Petaluma, CA (US); Seok-Ki Choi, Palo Alto, CA (US); Paul R. Fatheree, San Francisco, CA (US); Daniel Marquess, Half Moon Bay, CA (US); S. Derek Turner, Pacifica, CA (US)

(73) Assignee: Theravance, Inc., South San Francisco, CA (US)

( * ) Notice: Subject to any disclaimer, the term of this patent is extended or adjusted under 35 U.S.C. 154(b) by 230 days.

(21) Appl. No.: 10/824,738

(22) Filed: Apr. 15, 2004

(65) Prior Publication Data

US 2004/0204460 A1   Oct. 14, 2004

Related U.S. Application Data

(62) Division of application No. 09/943,420, filed on Aug. 30, 2001, now Pat. No. 6,756,400.

(60) Provisional application No. 60/229,572, filed on Aug. 31, 2000.

(51) Int. Cl.
*A01N 33/02* (2006.01)

(52) U.S. Cl. .................. 514/648; 514/652; 564/325; 564/330; 564/335; 564/353; 564/354

(58) Field of Classification Search ................ 564/325, 564/353, 354, 330, 335; 514/648, 652
See application file for complete search history.

(56) References Cited

U.S. PATENT DOCUMENTS

| | | | |
|---|---|---|---|
| 3,197,434 A | | 7/1965 | Preston et al. |
| 3,247,199 A | * | 4/1966 | Marxer et al. ................ 544/87 |
| 3,340,146 A | | 9/1967 | Werner |
| 3,449,418 A | * | 6/1969 | Werner ....................... 552/109 |
| 3,598,866 A | | 8/1971 | Nowak et al. |
| 4,008,265 A | | 2/1977 | Suzuki et al. |
| 5,736,568 A | * | 4/1998 | Rafferty et al. ............. 514/524 |

FOREIGN PATENT DOCUMENTS

| | | | |
|---|---|---|---|
| BE | 613 143 | | 7/1962 |
| DE | 1219039 | * | 6/1966 |
| GB | 1584428 | * | 2/1981 |
| NL | 6600012 | | 7/1966 |

OTHER PUBLICATIONS

Lowe et al., Chem. Abst. 46:48437 (1952).*
Benoit et al., Chem. Abst. 47:12092 (1953).*
Ando et al., "Aromatic polyether polyureas", Chemical Abstract Services, Accession No. 67:117575, XP002190008 (1963).
Ando et al., "Synthesis of polyamides by cyanoethylation of bisphenols. IX. Properties of some polyamides with p-phenyleneoxy groups in the chain", Chemical Abstract Services, Accession No. 67:22785, XP002190009 (1966).
Carissimi et al., "Preparation and pharmacology of ethylalkylamine ethers derived from hydroxy and dihydroxydiphenyl sulfones and their quaternary salts", Chemical Abstract Services, Accession No. CA53:8142c, XP002190011 (1954).
Gilbert et al., "Study of the effects of basic di- and tri-phenyl derivatives on malignant cell proliferations: an example of the application of correspondence factor analysis to structure-activity relationships (SAR)", Chemical Abstract Services, Accession No. 122:23229, XP002190010 (1994).

* cited by examiner

*Primary Examiner*—Peter O'Sullivan
(74) *Attorney, Agent, or Firm*—Jeffrey A. Hagenah

(57) ABSTRACT

The invention provides sodium channel modulating compounds of formula I:

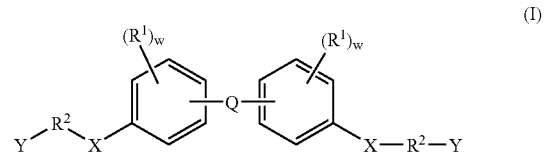

wherein X, Y, Q, $R^1$, w, and $R^2$ have any of the values defined in the specification, and salts thereof, which are useful for treating diseases or conditions associated with sodium channel activity, such as neuropathic pain. The invention also provides pharmaceutical compositions comprising a compound of formula (I) or a salt thereof, as well as therapeutic methods comprising administering such a compound or salt to a mammal (e.g. a human).

5 Claims, 3 Drawing Sheets

XXIX

XXX

SODIUM CHANNEL MODULATORS

CROSS REFERENCE TO RELATED APPLICATION

This application is a divisional application of U.S. patent application Ser. No. 09/943,420, filed Aug. 30, 2001, now U.S. Pat. No. 6,756,400 which claims priority from U.S. Provisional Applicaiton No. 60/229,572, filed 31 Aug. 2000, the entire contents of which are hereby incorporated by reference herein.

FIELD OF THE INVENTION

The invention is directed to novel compounds that bind to sodium channels and modulate their activity. The invention is also directed to pharmaceutical compositions comprising such compounds, methods of using such compounds to treat diseases associated with the activity of sodium channels, and processes and intermediates useful for preparing such compounds.

BACKGROUND

Voltage-gated ion channels play a critical role in the electrical activity of neuronal and muscle cells. Large families of voltage-gated ion channels (e.g. sodium channels) have been identified. These ion channels have been the target of significant pharmocologic study, due to their potential role in a variety of pathological conditions.

For example, the activity of sodium channels has been implicated in numerous pathological conditions, including neuropathic pain. Neuropathic pain is a chronic condition associated with diabetes, chronic inflammation, cancer and herpes virus infection. An estimated 75 million people worldwide are expected to suffer from neuropathic pain by the year 2010. Unfortunately, current treatment options typically provide only partial pain relief, and are limited by inconvenient dosing and by side effects, such as somnolence, ataxia, edema, gastrointestinal discomfort and respiratory depression.

Thus, despite the limited success that has been achieved using sodium channel modulators to treat pain, there continues to be a need for novel agents and methods that are useful for treating neuropathic pain, as well as other conditions associated with the activity of sodium channels. Particularly useful agents may be more potent or cause fewer side effects than existing agents.

SUMARY OF THE INVENTION

The present invention provides novel compounds that bind to sodium channels and modulate (e.g. block) their activity. Accordingly, the invention provides a compound of the invention, which is compound of formula I:

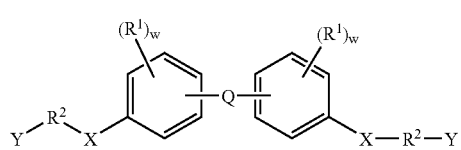

(I)

wherein:
Q is —O—, —S(O)$_m$—, —(CR$^5$R$^6$)$_p$—, —O(CR$^5$R$^6$)$_r$ O—, or —N(R$^k$)—;

each R$^1$ is independently alkyl, alkenyl, alkynyl, aryl, heteroaryl, cycloalkyl, heterocyclyl, or R$^a$;

each R$^2$ is independently a covalent bond or alkylene; wherein alkylene is optionally substituted with 1 to 4 substituents independently selected from R$^b$;

each X is independently oxy (—O—) or —N(R$^m$)—;

each Y is independently NR$^n$R$^p$ or a heterocyclyl containing at least one nitrogen atom, wherein each nitrogen of the heterocyclyl is substituted with R$^3$ or is linked to R$^2$, and wherein each heterocycle of Y is optionally substituted with 1, 2, 3, or 4 substituents independently selected from R$^4$;

each R$^3$ is independently hydrogen, alkyl, alkenyl, alkynyl, aryl, heteroaryl, cycloalkyl, oxo, or heterocyclyl; and each R$^4$ is independently alkyl, alkenyl, alkynyl, aryl, heteroaryl, cycloalkyl, heterocyclyl, or R$^b$; or R$^3$ and R$^4$ are joined to form a C$_{1-4}$ alkylene group, wherein the alkylene group is optionally substituted with 1 to 4 substituents independently selected from R$^b$;

each R$^5$ and R$^6$ is independently hydrogen, alkyl, alkenyl, alkynyl, aryl, heteroaryl, cycloalkyl, or heterocyclyl; or R$^5$ and R$^6$ together with the carbon atom to which they are attached form a ring having from 5 to 7 ring atoms, wherein the ring optionally contains 1 or 2 heteroatoms in the ring independently selected from oxygen, sulfur or nitrogen;

wherein for R$^1$–R$^6$, each alkyl, alkenyl, and alkynyl is optionally substituted with R$^x$, or with 1, 2, 3, or 4 substituents independently selected from R$^b$; for R$^1$–R$^6$, each aryl and heteroaryl is optionally substituted with 1 to 4 substituents independently selected from R$^c$, and for R$^1$–R$^6$, each cycloalkyl and heterocyclyl is optionally substituted with 1 to 4 substituents independently selected from R$^b$ and R$^c$;

each R$^a$ is independently —OR$^d$, —NO$_2$, halo, —S(O)$_m$ R$^d$, —SR$^d$, —S(O)$_2$OR$^d$, —S(O)$_m$NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$ CONR$^d$R$^e$, —OC(O)R$^d$, —CN, —C(O)NR$^d$R$^e$, —NR$^d$C(O) R$^e$, —OC(O)NR$^d$R$^e$, —NR$^d$C(O)OR$^e$, —NR$^d$C(O)NR$^d$ R$^e$, —CR$^d$(=N—OR$^e$), —CF$_3$, or —OCF$_3$;

each R$^b$ is independently R$^a$, oxo or =N—OR$^e$;

each R$^c$ is independently R$^a$, alkyl, alkenyl, or alkynyl; wherein each alkyl, alkenyl and alkynyl is optionally substituted with 1 to 4 substituents independently selected from R$^b$;

each R$^d$ and R$^e$ is independently hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from R$^h$; or R$^d$ and R$^e$ together with the atoms to which they are attached form a heterocyclic ring having from 5 to 7 ring atoms, wherein the heterocyclic ring optionally contains 1 or 2 additional heteroatoms independently selected from oxygen, sulfur or nitrogen;

each R$^f$ and R$^g$ is independently hydrogen, alkyl, aryl, heteroaryl, cycloalkyl, or heterocyclyl; wherein each alkyl, aryl, heteroaryl, cycloalkyl and heterocyclyl is optionally substituted with 1 to 4 substituents independently selected from R$^h$; or R$^f$ and R$^g$ together with the carbon atom to which they are attached form a ring having from 5 to 7 ring atoms, wherein the ring optionally contains 1 or 2 heteroatoms independently selected from oxygen, sulfur or nitrogen;

each R$^h$ is independently halo, C$_{1-6}$ alkyl, C$_{1-6}$ alkoxy, aryl, (aryl)-C$_{1-6}$ alkyl, heteroaryl, (heteroaryl)C$_{1-6}$ alkyl, hydroxy, amino, —NHC$_{1-6}$ alkyl, —N(C$_{1-6}$ alkyl)$_2$, —OC (O)C$_{1-6}$ alkyl, —C(O)C$_{1-6}$ alkyl, —C(O)OC$_{1-6}$ alkyl, —NHC(O)C$_{1-6}$ alkyl, —C(O)NHC$_{1-6}$ alkyl, carboxy, nitro, —CN, or —CF$_3$;

R$^k$ is hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from R$^h$;

R$^m$ is hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from R$^h$;

each R$^n$ and R$^p$ is independently hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from R$^h$; and each R$^x$ is independnetly aryl, heteroaryl, cycloalkyl or heterocyclyl; wherein each aryl or heteroaryl is optionally substituted with 1 to 4 substituents selected from the group consisting of R$^c$, and wherein each cycloalkyl and heterocyclyl is optionally substituted with 1 to 4 substituents selected from R$^b$;

m is 0, 1, or 2;
n is 1, 2, 3, 4, 5, 6, 7, 8, 9, or 10;
p is 1, 2, or 3;
r is 2, or 3; and
each w is independently 0, 1, 2, 3, or 4;
or a pharmaceutically-acceptable salt thereof;

provided that when any Y is NR$^n$R$^p$ or a nitrogen-linked heterocyclyl, then the R$^2$ attached to that Y is not a covalent bond or methylene.

The invention also provides a pharmaceutical composition comprising a compound of the invention and pharmaceutically acceptable carrier.

The invention also provides a method of treating a disease or condition associated with sodium channel activity (e.g. neuropathic pain) in a mammal, comprising administering to the mammal, a therapeutically effective amount of a compound of the invention. The invention also provides a method of treating a disease or condition associated with sodium channel activity (e.g. neuropathic pain) in a mammal, comprising administering to the mammal, a therapeutically effective amount of a pharmaceutical composition of the invention.

The invention also provides processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with sodium channel activity (e.g. neuropathic pain) in a mammal.

Preferred compounds of the invention are the compounds of formula I shown in Table I below.

TABLE I

Preferred Compounds of Formula I

| Compound | Structure |
|---|---|
| 1 | 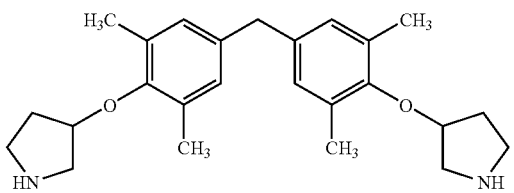 |
| 2 | |
| 3 | 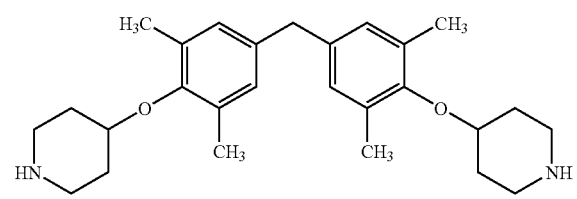 |
| 4 | 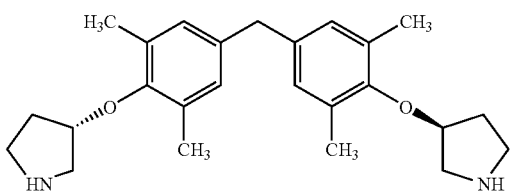 |

TABLE I-continued
Preferred Compounds of Formula I
| Compound | Structure |
|---|---|
| 5 | 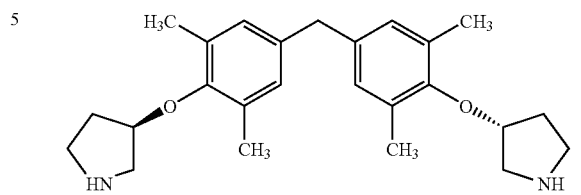 |
| 6 | 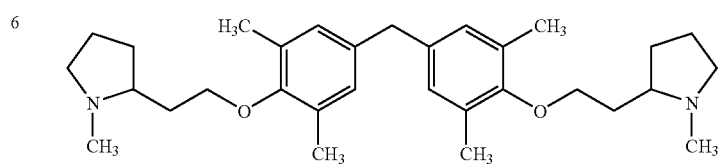 |
| 7 | 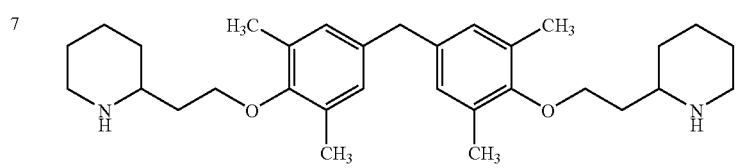 |
| 8 | 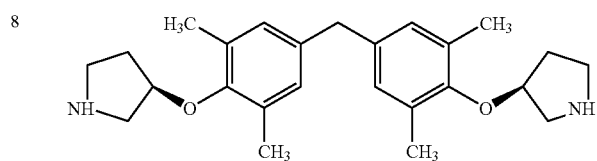 |
| 9 | 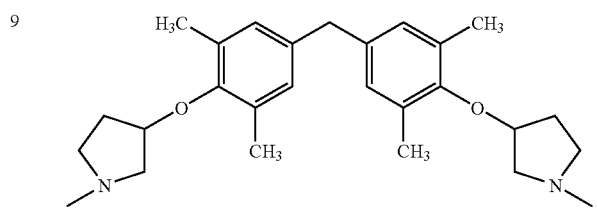 |
| 10 | 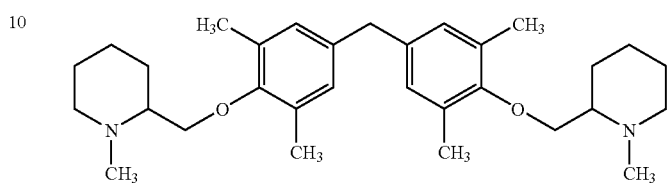 |
| 11 | 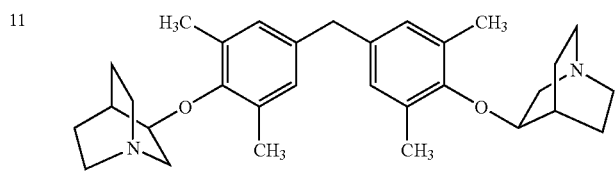 |
| 12 | 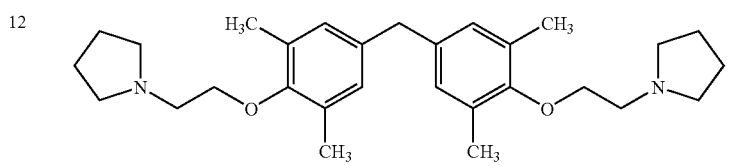 |

TABLE I-continued

Preferred Compounds of Formula I

| Compound | Structure |
|---|---|
| 13 | 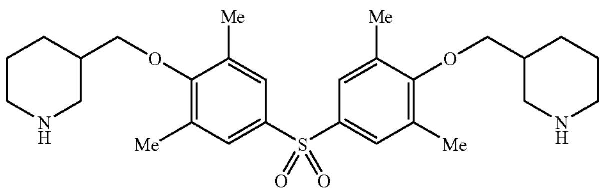 |
| 14 | 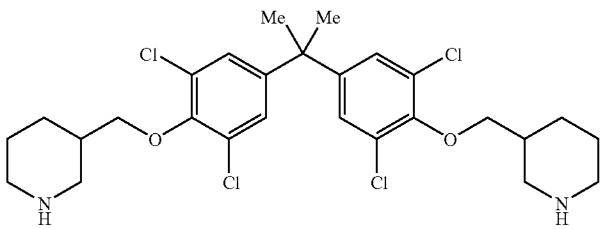 |
| 15 | 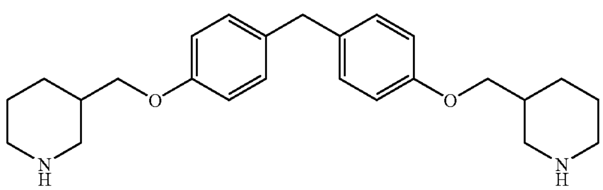 |
| 16 | 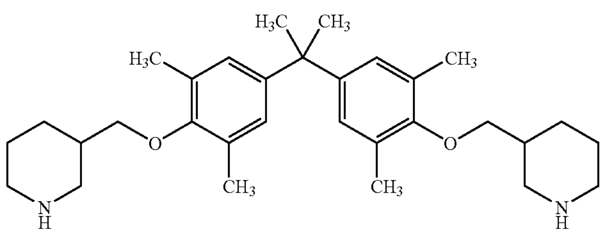 |
| 17 | 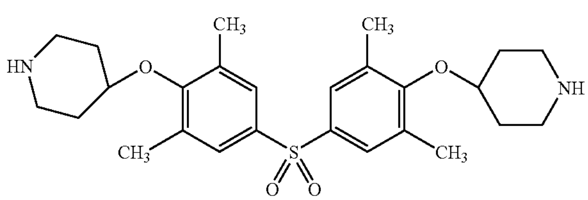 |
| 18 | 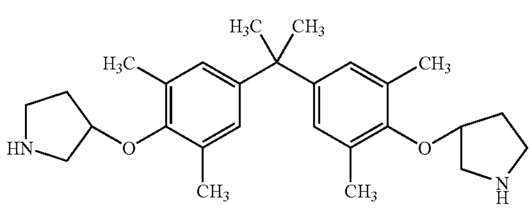 |
| 19 | 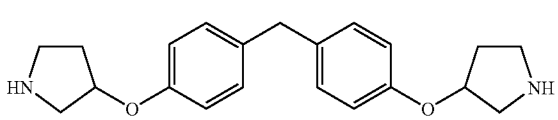 |

TABLE I-continued
Preferred Compounds of Formula I
| Compound | Structure |
|---|---|
| 20 | 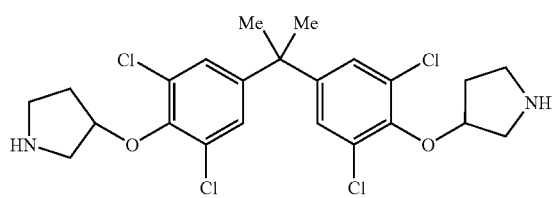 |
| 21 | 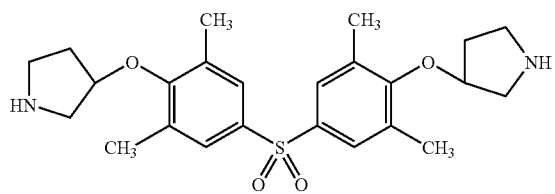 |
| 22 | 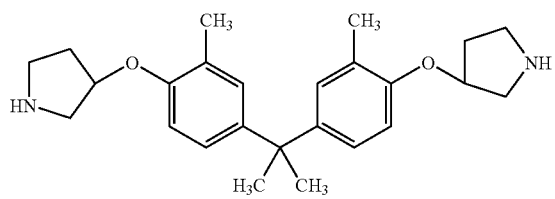 |
| 23 | 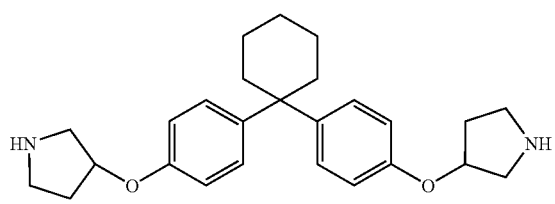 |
| 24 | 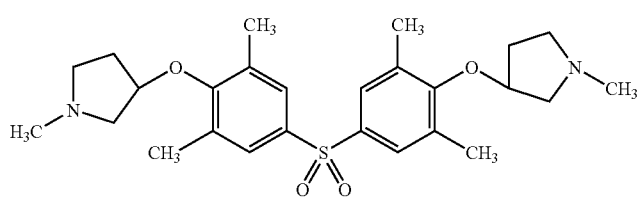 |
| 25 | 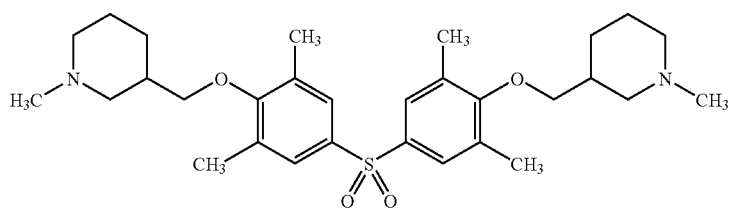 |
| 26 | 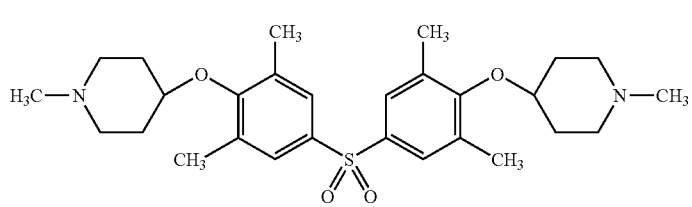 |

TABLE I-continued
Preferred Compounds of Formula I
| Compound | Structure |
|---|---|
| 27 | 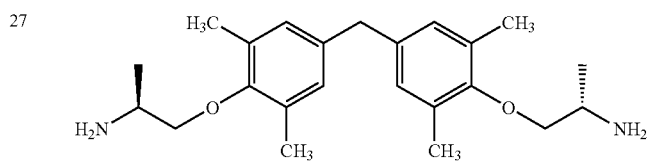 |
| 28 | 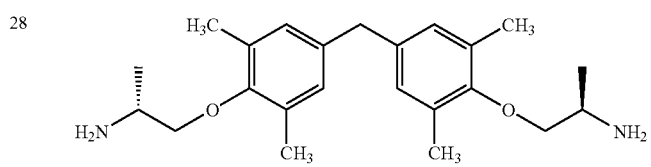 |
| 29 | 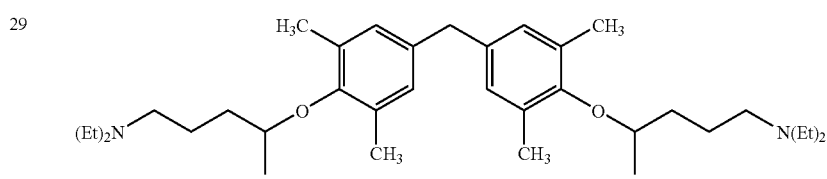 |
| 30 | 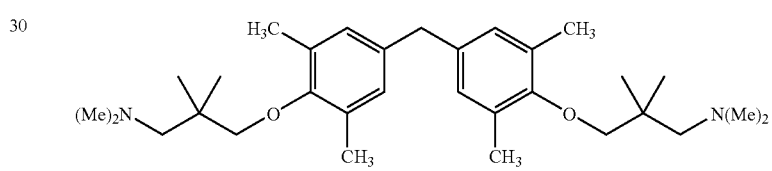 |
| 31 | 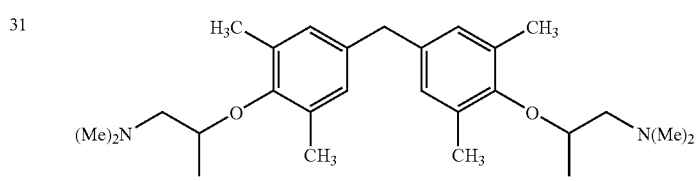 |
| 32 | 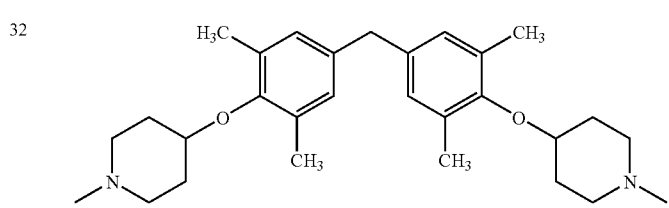 |
| 33 | 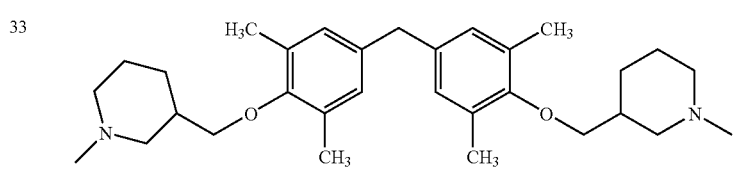 |
| 34 | 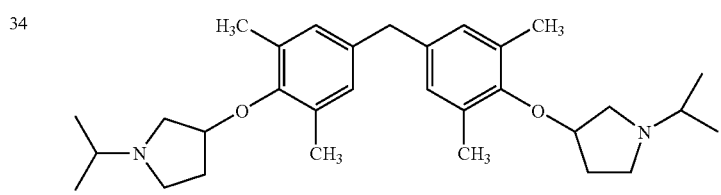 |

TABLE I-continued

Preferred Compounds of Formula I

| Compound | Structure |
| --- | --- |
| 35 | 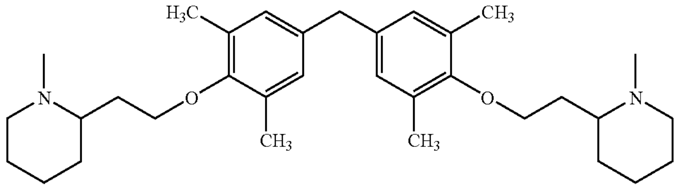 |
| 36 | 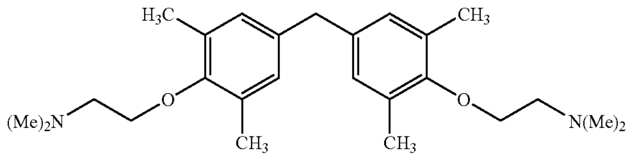 |
| 37 | 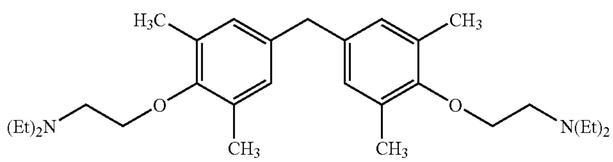 |
| 38 | 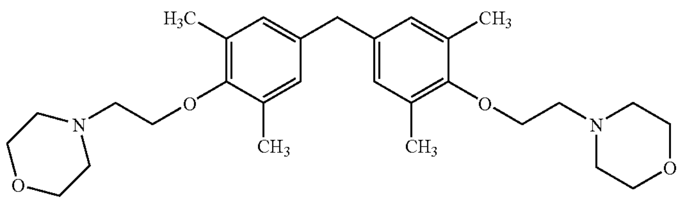 |
| 39 | 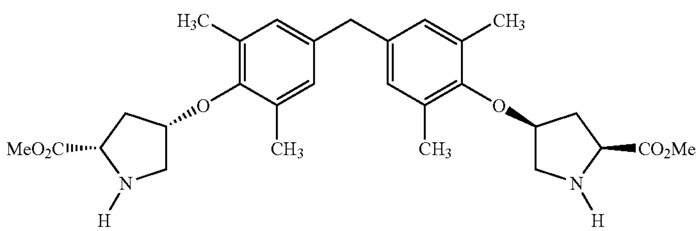 |
| 40 | 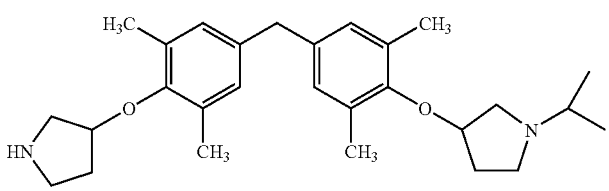 |
| 41 | 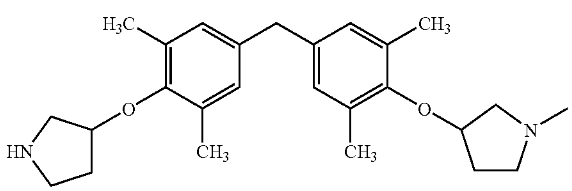 |

TABLE I-continued

Preferred Compounds of Formula I

| Compound | Structure |
|---|---|
| 42 | 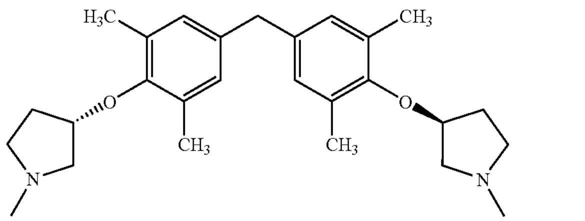 |
| 43 | 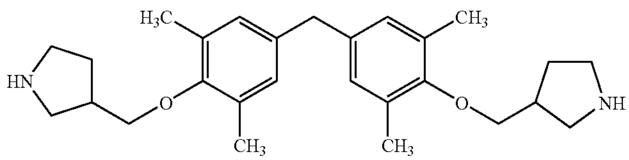 |
| 44 | 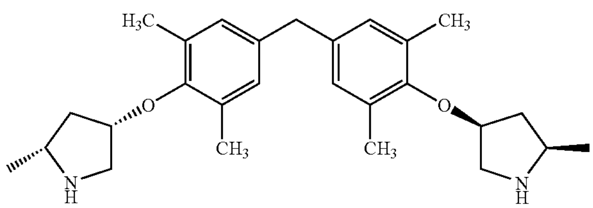 |
| 45 | 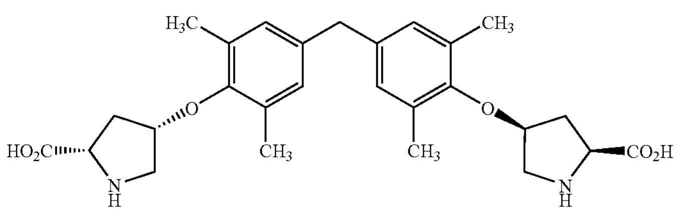 |
| 46 | 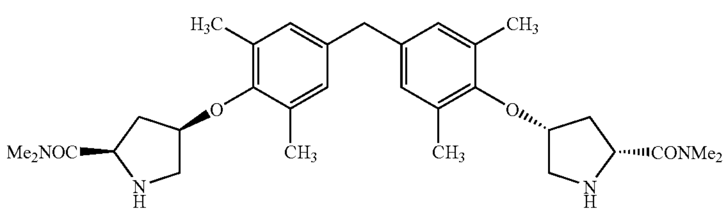 |
| 47 | 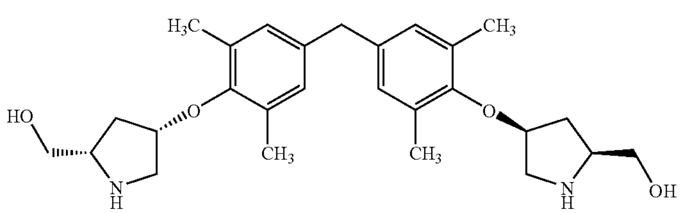 |
| 48 | 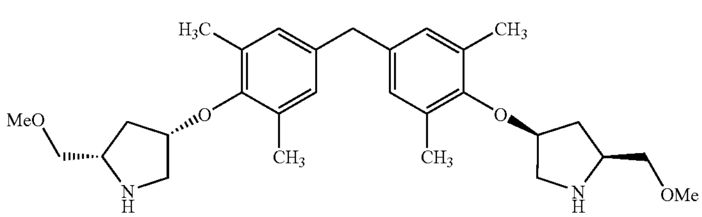 |

TABLE I-continued
Preferred Compounds of Formula I
| Compound | Structure |
|---|---|
| 49 | 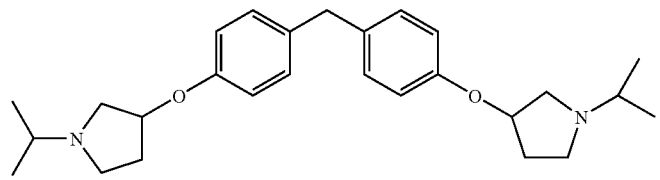 |
| 50 | 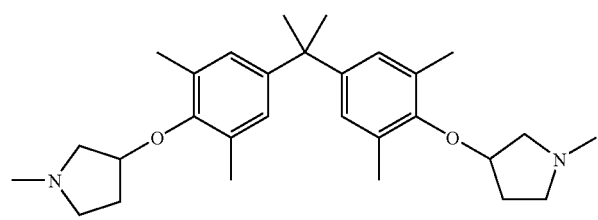 |
| 51 | 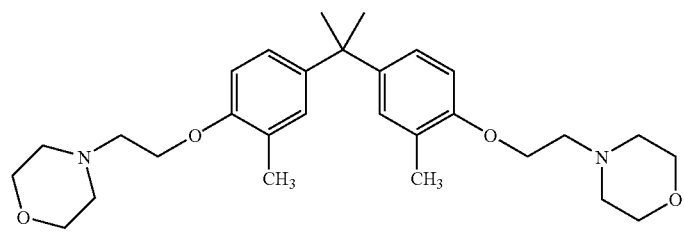 |
| 52 | 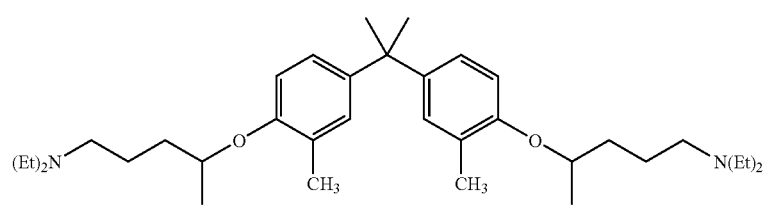 |
| 53 | 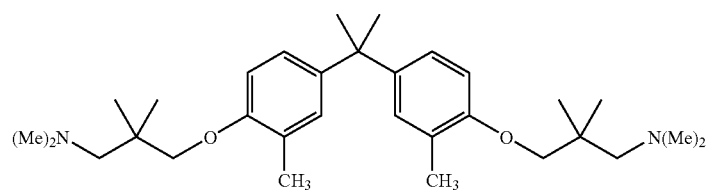 |
| 54 | 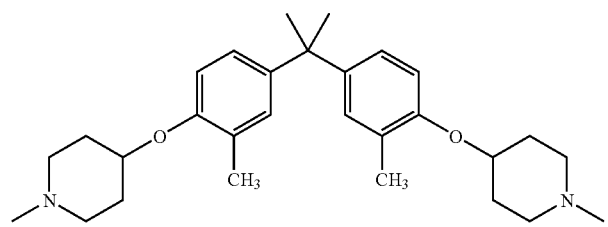 |
| 55 | 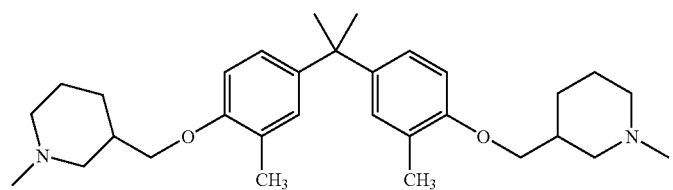 |

TABLE I-continued
Preferred Compounds of Formula I
| Compound | Structure |
|---|---|
| 56 | 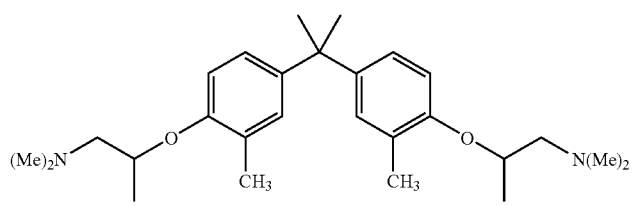 |
| 57 | 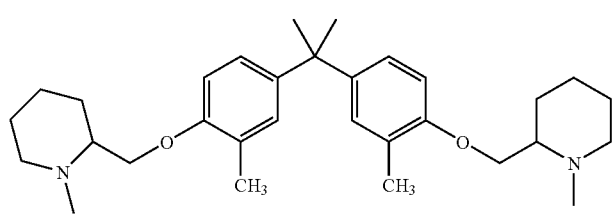 |
| 58 | 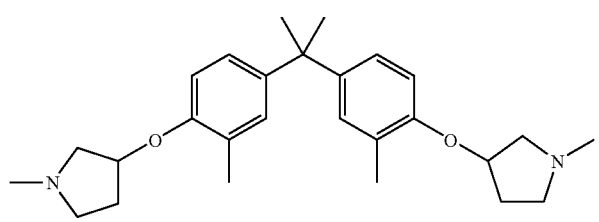 |
| 59 | 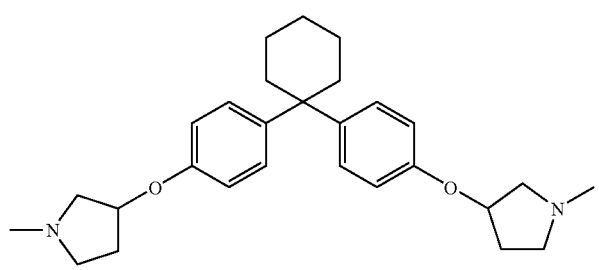 |
| 60 | 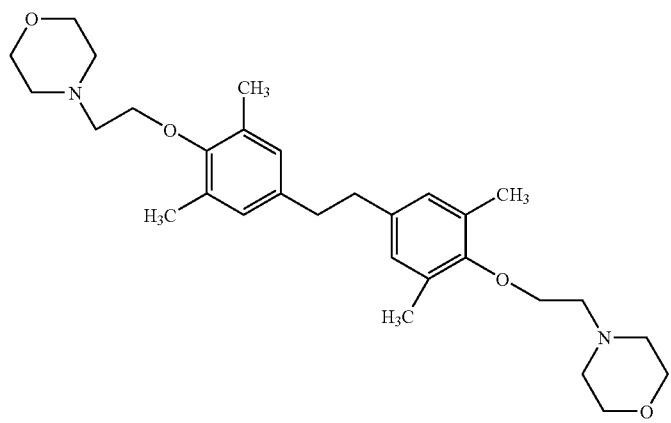 |

TABLE I-continued
Preferred Compounds of Formula I
| Compound | Structure |
|---|---|
| 61 | 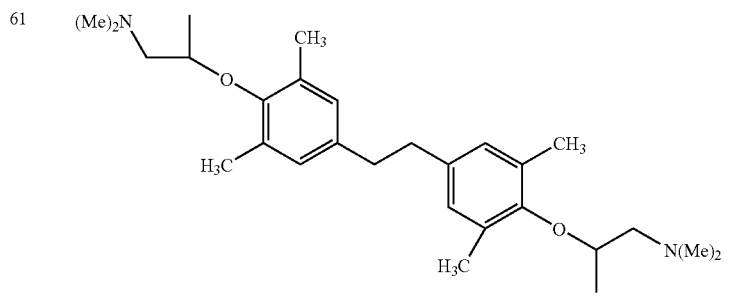 |
| 62 | 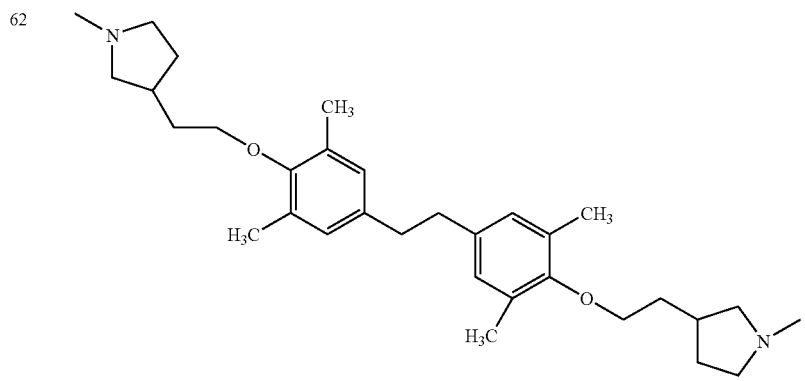 |
| 63 | 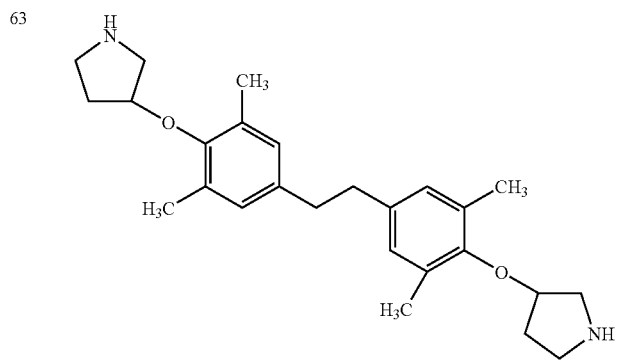 |
| 64 | 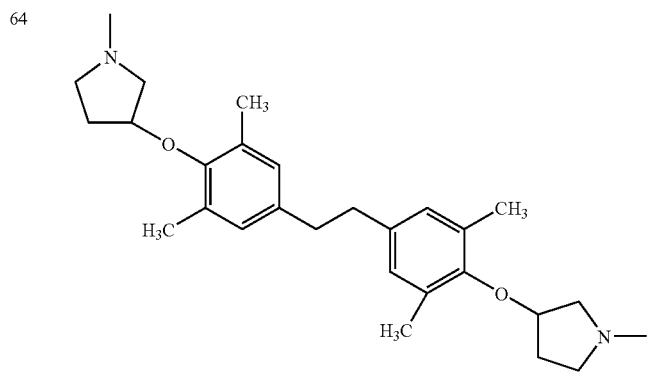 |

TABLE I-continued
Preferred Compounds of Formula I
| Compound | Structure |
|---|---|
| 65 | 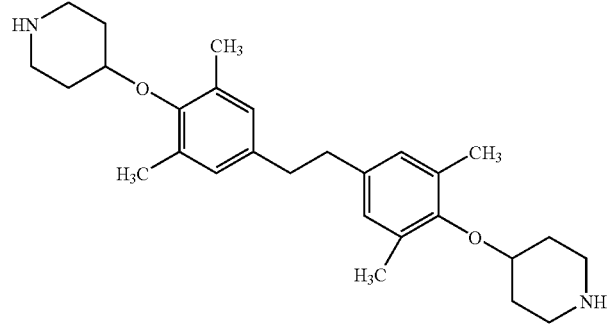 |
| 66 | 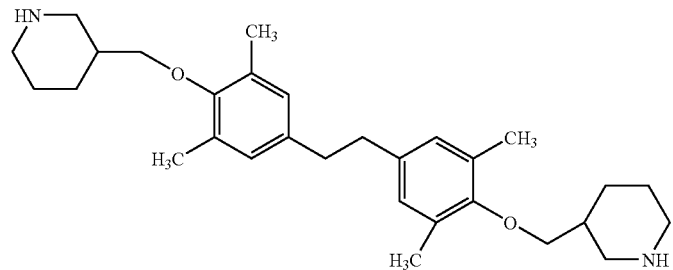 |
| 67 | 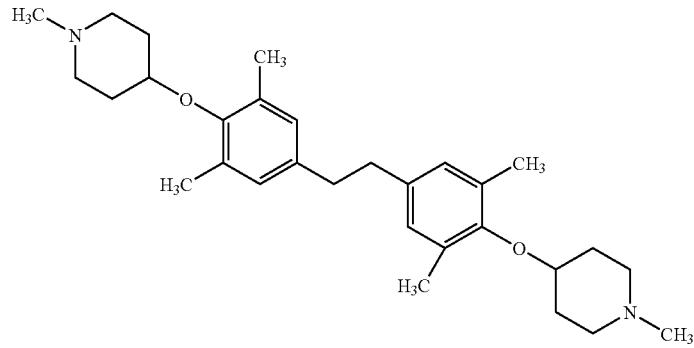 |
| 68 | 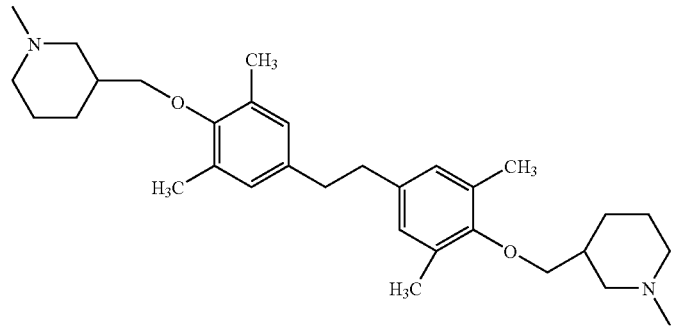 |

TABLE I-continued
Preferred Compounds of Formula I
| Compound | Structure |
|---|---|
| 69 | 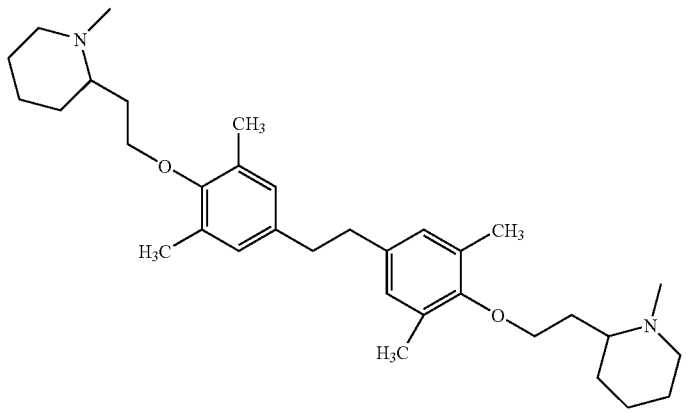 |
| 70 | 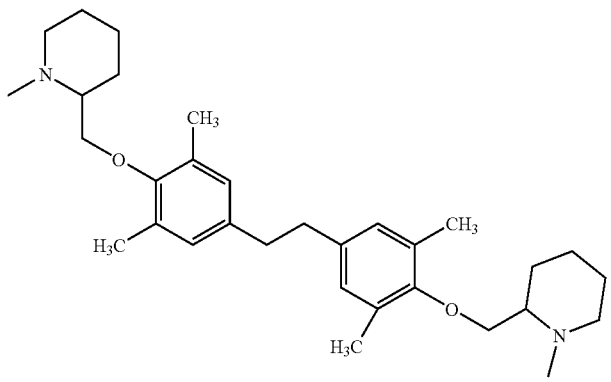 |
| 71 | 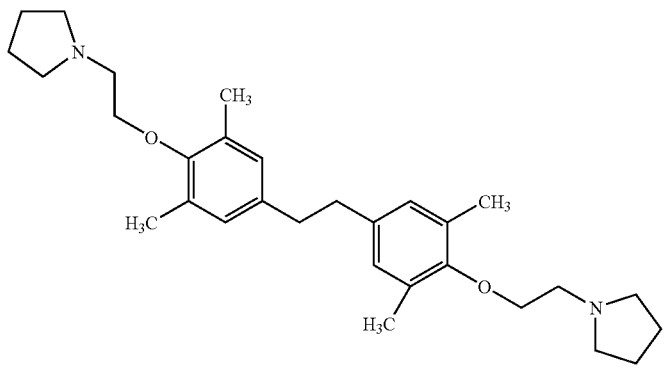 |
| 72 | 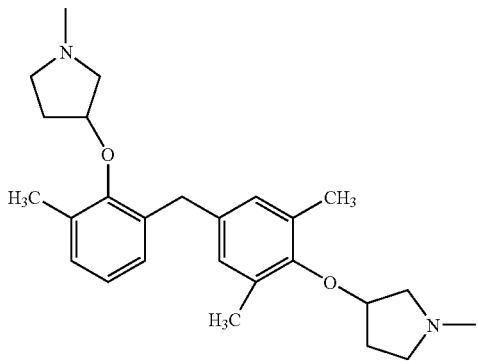 |

TABLE I-continued
Preferred Compounds of Formula I
| Compound | Structure |
|---|---|
| 73 | 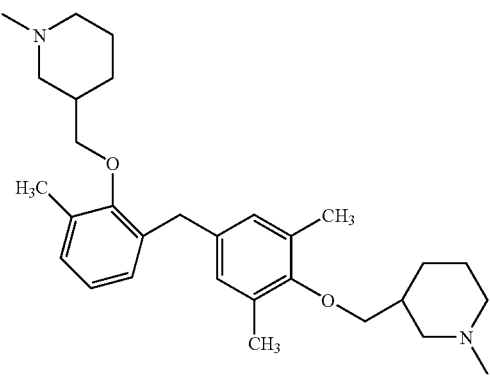 |
| 74 | 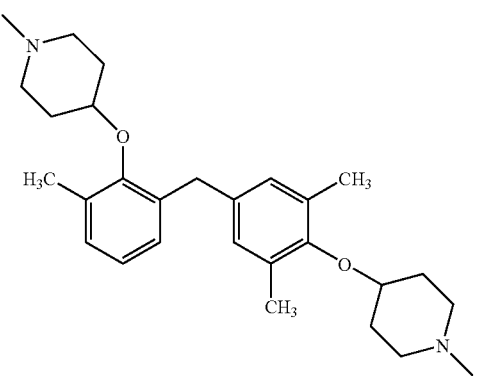 |
| 75 | 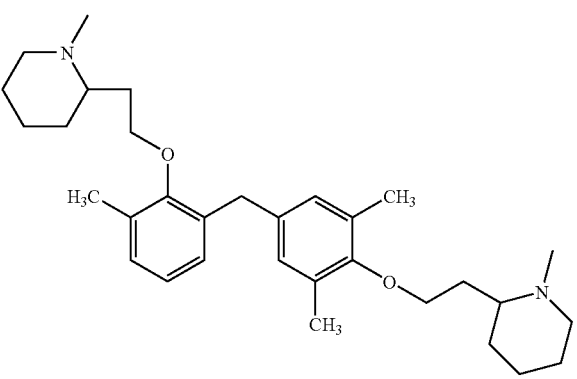 |
| 76 | 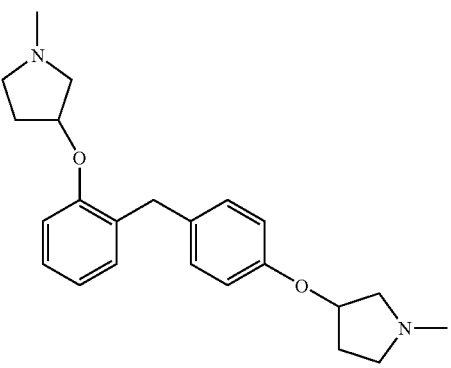 |

TABLE I-continued

Preferred Compounds of Formula I

| Compound | Structure |
|---|---|
| 77 | 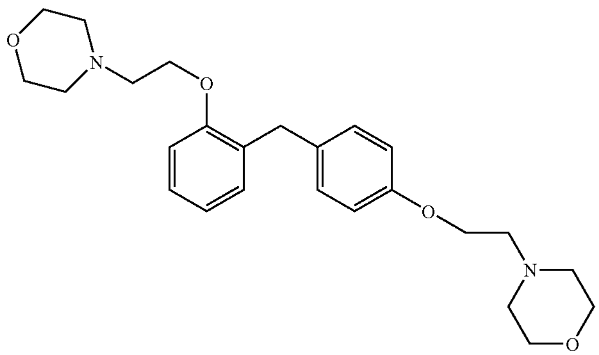 |
| 78 | 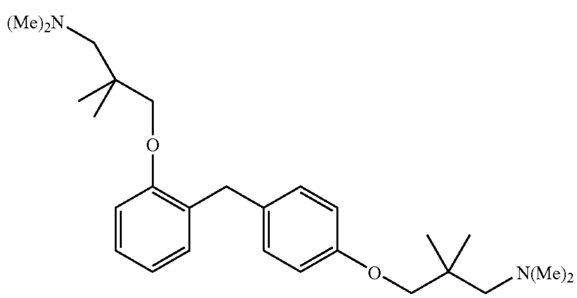 |
| 79 | 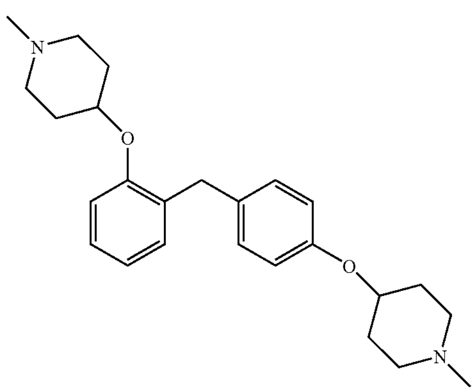 |
| 80 | 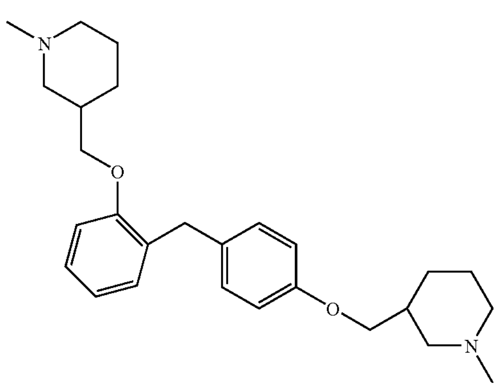 |

TABLE I-continued

Preferred Compounds of Formula I

| Compound | Structure |
|---|---|
| 81 | 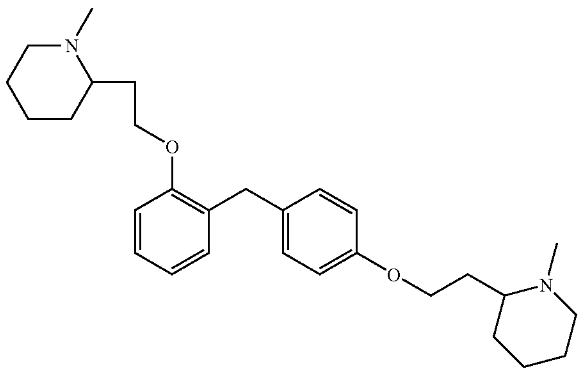 |
| 82 | 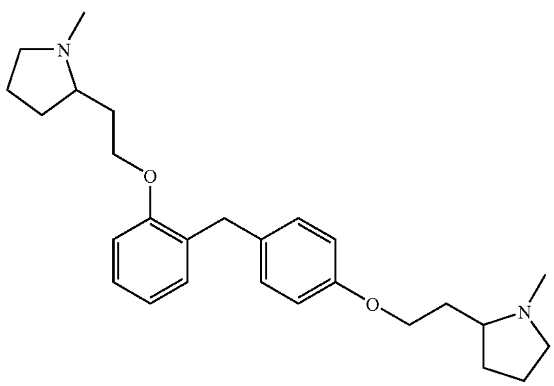 |
| 83 | 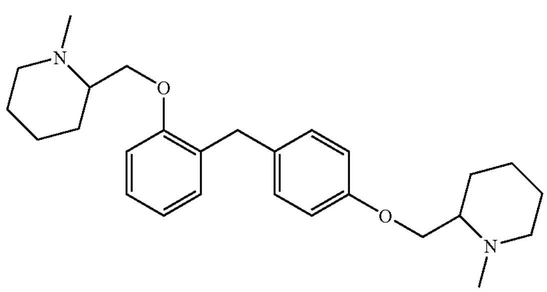 |
| 84 | 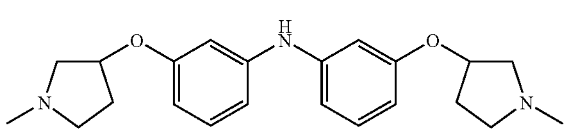 |
| 85 | 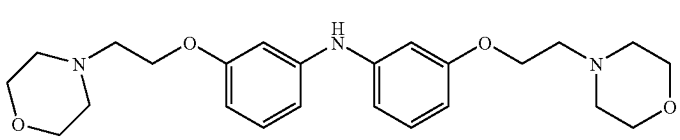 |
| 86 | 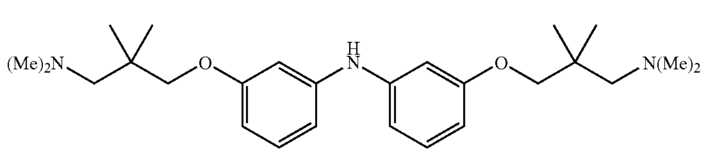 |

TABLE I-continued
Preferred Compounds of Formula I
| Compound | Structure |
|---|---|
| 87 | 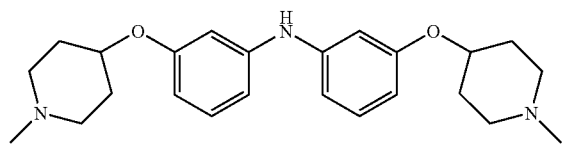 |
| 88 | 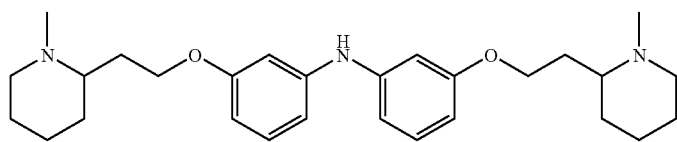 |
| 89 | 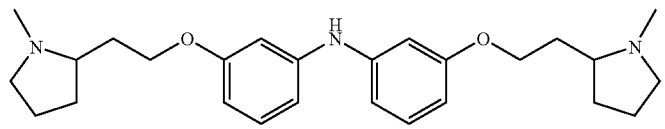 |
| 90 | 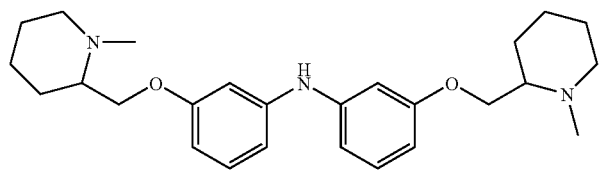 |
| 91 | 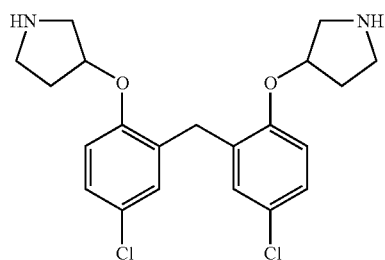 |
| 92 | 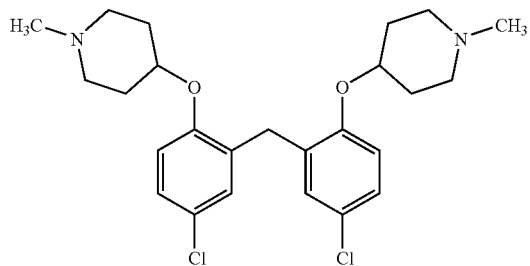 |
| 93 | 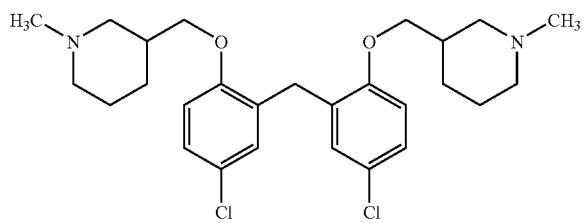 |

TABLE I-continued

Preferred Compounds of Formula I

| Compound | Structure |
|---|---|
| 94 | 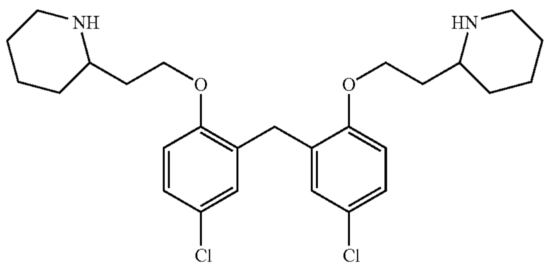 |
| 95 | 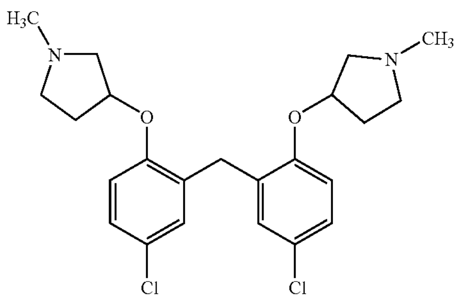 |
| 96 | 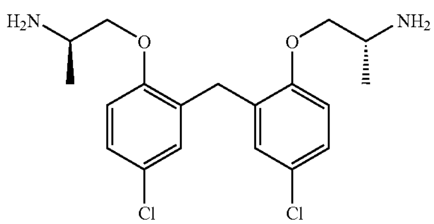 |
| 97 | 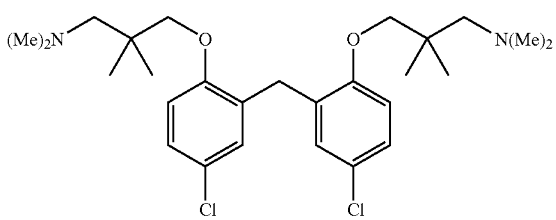 |
| 98 | 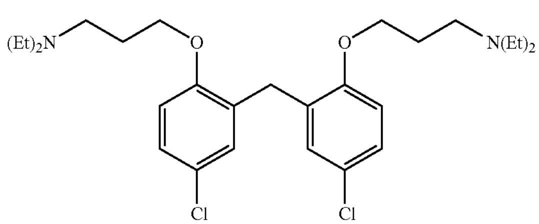 |
| 99 | 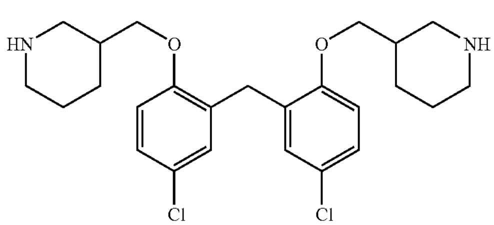 |

TABLE I-continued

Preferred Compounds of Formula I

| Compound | Structure |
|---|---|
| 100 | (structure) |
| 101 | (structure) |
| 102 | (structure) |
| 103 | (structure) |
| 104 | (structure) |
| 105 | (structure) |
| 106 | (structure) |
| 107 | (structure) |
| 108 | (structure) |

TABLE I-continued
Preferred Compounds of Formula I
| Compound | Structure |
|---|---|
| 109 | 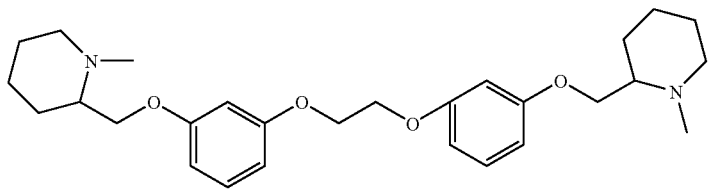 |
| 110 | 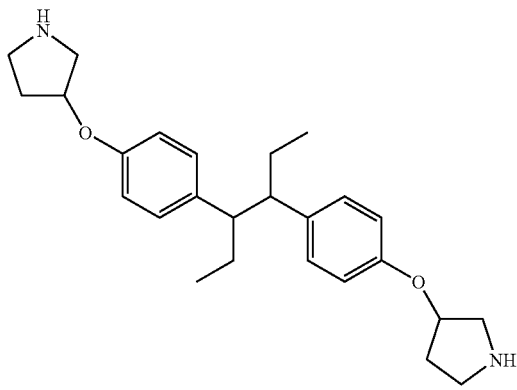 |
| 111 | 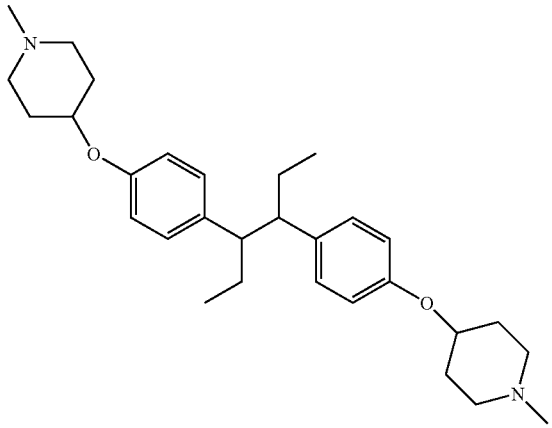 |
| 112 | 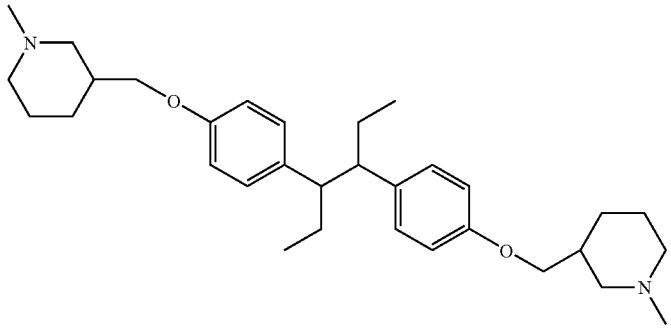 |

TABLE I-continued
Preferred Compounds of Formula I
| Compound | Structure |
|---|---|
| 113 | 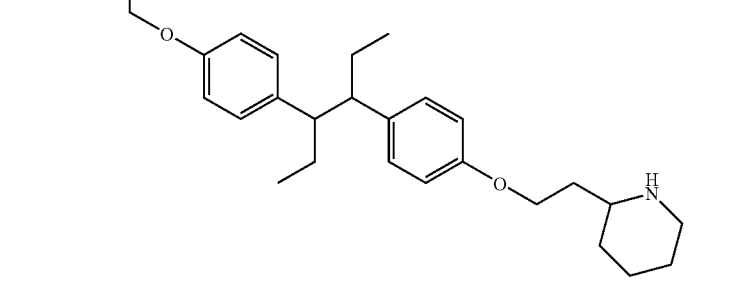 |
| 114 | 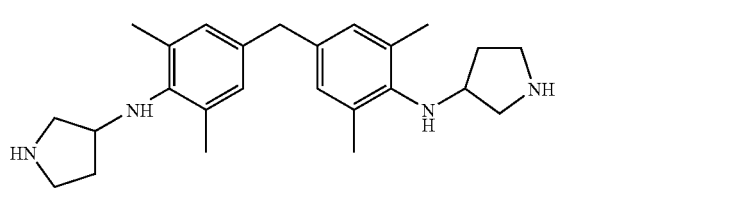 |
| 115 | 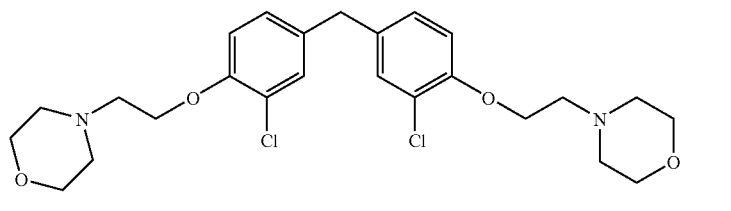 |
| 116 | 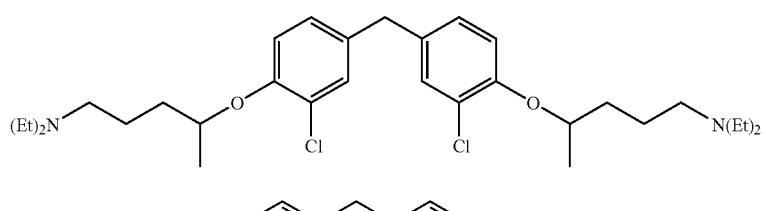 |
| 117 | 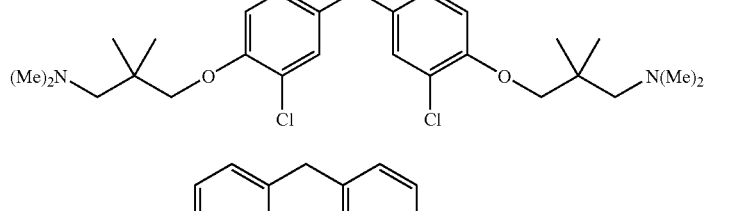 |
| 118 | 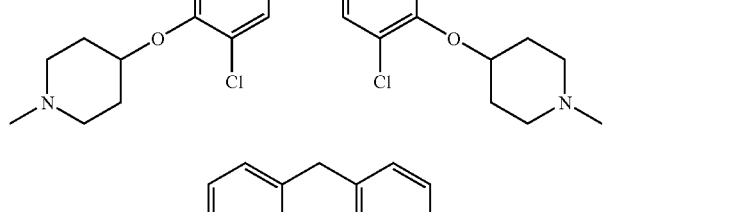 |
| 119 | 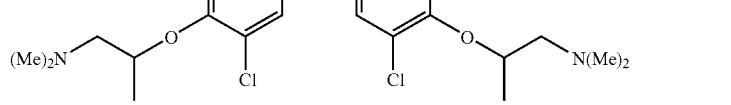 |

TABLE I-continued
Preferred Compounds of Formula I
| Compound | Structure |
|---|---|
| 120 | 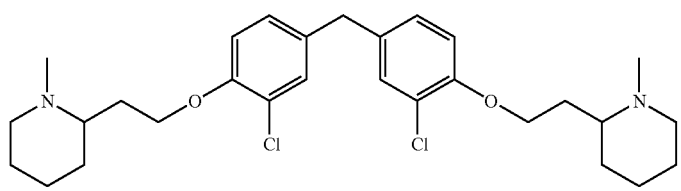 |
| 121 | 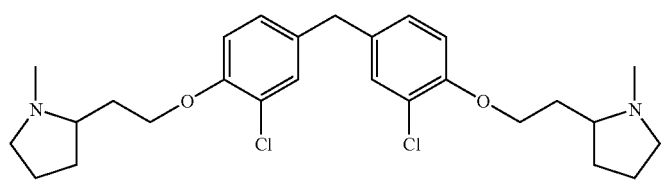 |
| 122 | 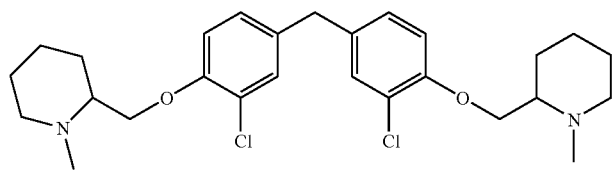 |
| 123 | 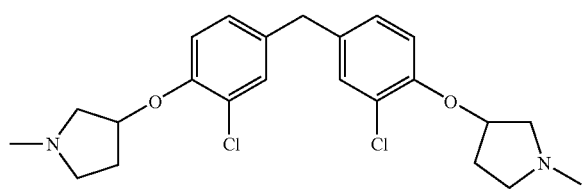 |
| 124 | 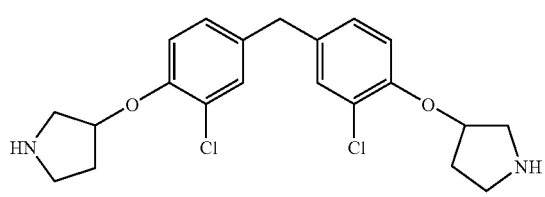 |
| 125 | 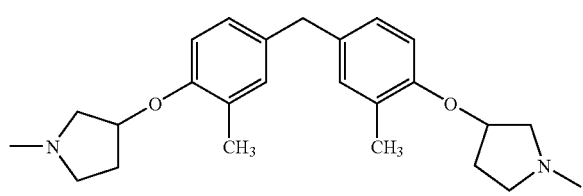 |
| 126 | 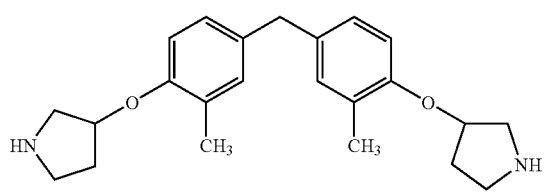 |

TABLE I-continued
Preferred Compounds of Formula I
| Compound | Structure |
|---|---|
| 127 | 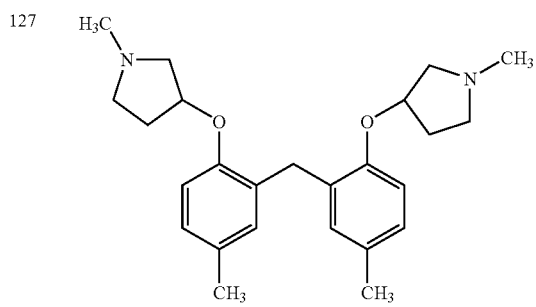 |
| 128 | 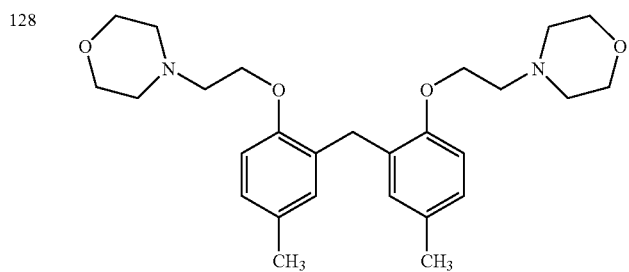 |
| 129 | 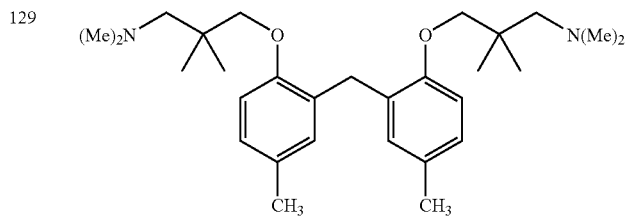 |
| 130 | 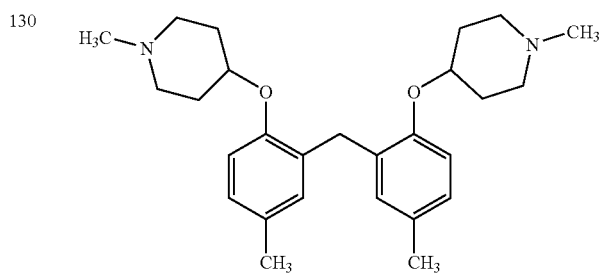 |
| 131 | 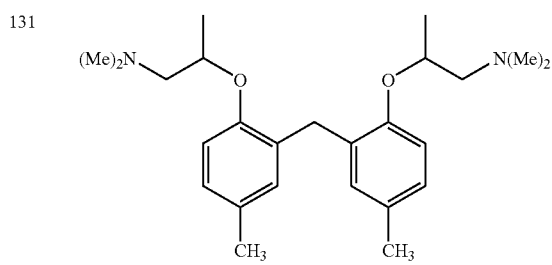 |

TABLE I-continued
Preferred Compounds of Formula I
| Compound | Structure |
|---|---|
| 132 | 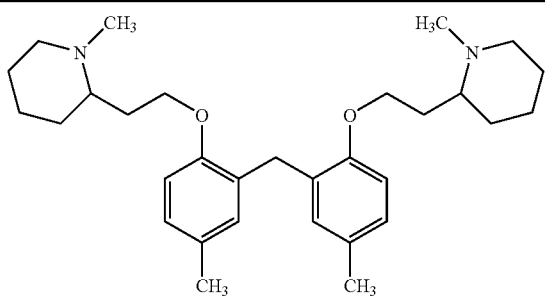 |
| 133 | 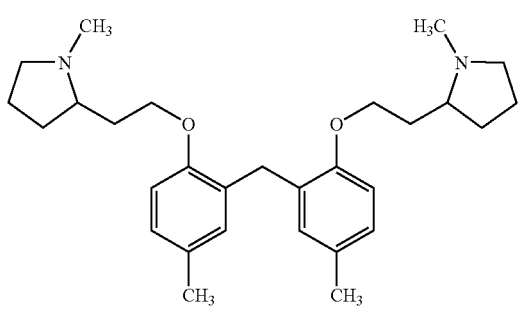 |
| 134 | 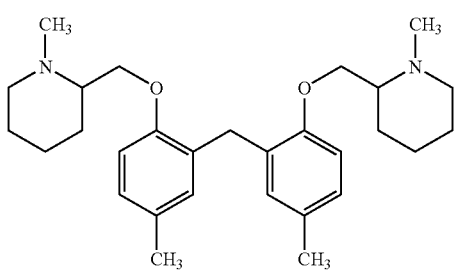 |
| 135 | 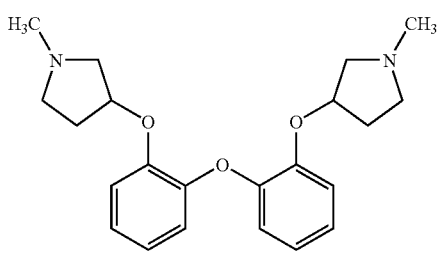 |
| 136 | 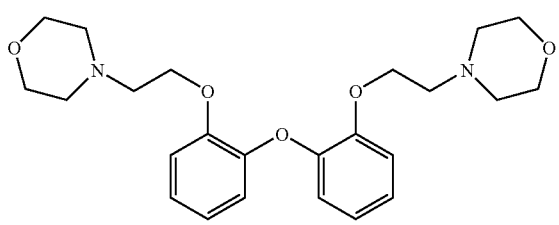 |
| 137 | 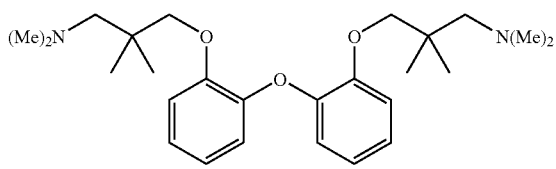 |

TABLE I-continued
Preferred Compounds of Formula I
| Compound | Structure |
|---|---|
| 138 | 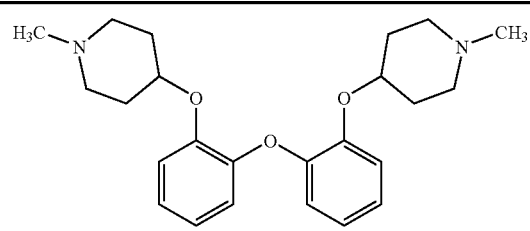 |
| 139 | 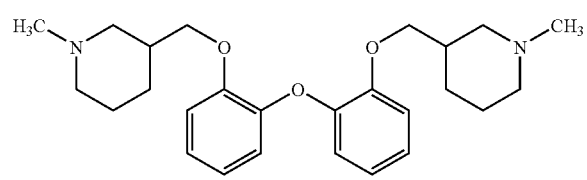 |
| 140 | 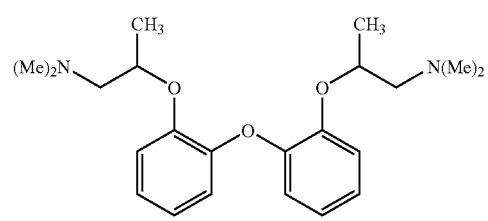 |
| 141 | 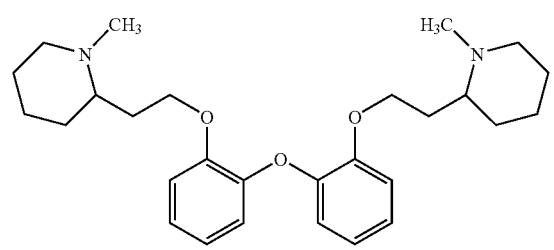 |
| 142 | 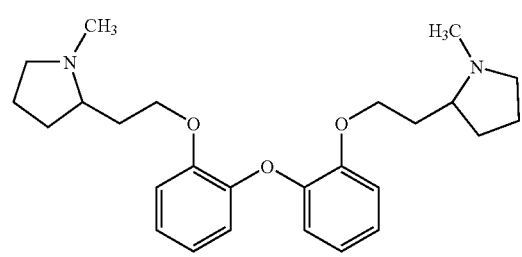 |
| 143 | 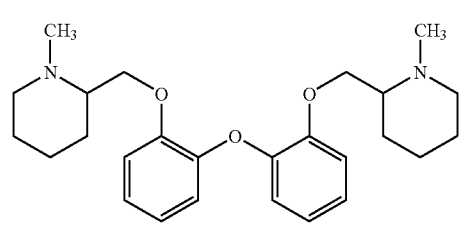 |
| 144 | 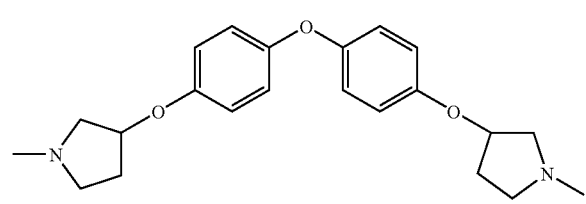 |

TABLE I-continued
Preferred Compounds of Formula I
| Compound | Structure |
|---|---|
| 145 | 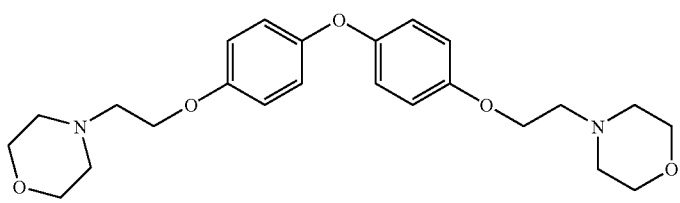 |
| 146 | 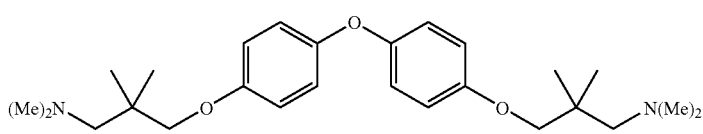 |
| 147 | 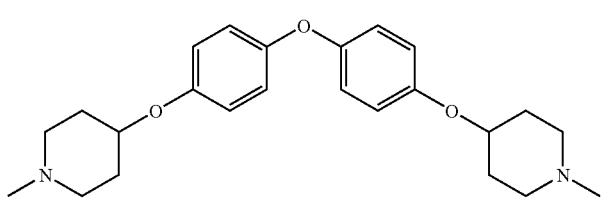 |
| 148 | 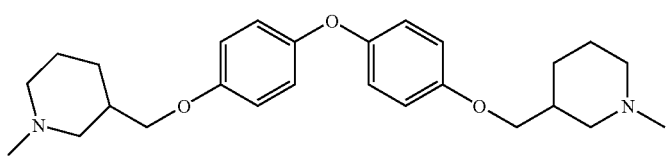 |
| 149 | 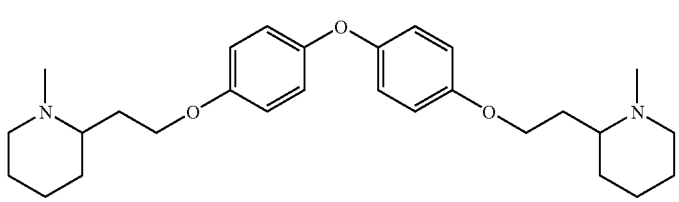 |
| 150 | 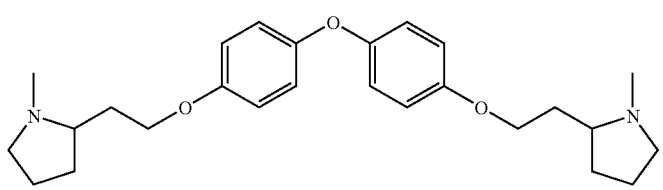 |
| 151 | 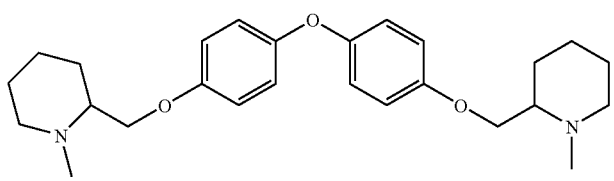 |
| 152 | 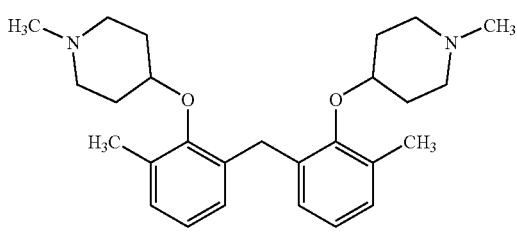 |

TABLE I-continued

Preferred Compounds of Formula I

| Compound | Structure |
|---|---|
| 153 | 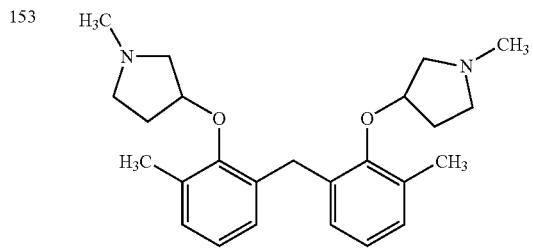 |
| 154 | 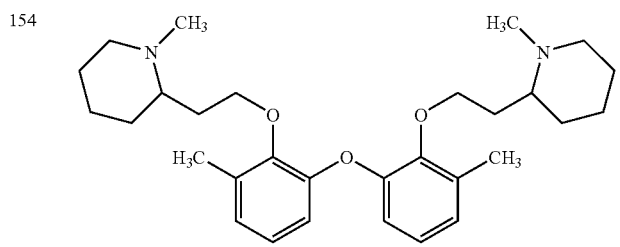 |

DETAILED DESCRIPTION OF THE INVENTION

Figure 1:
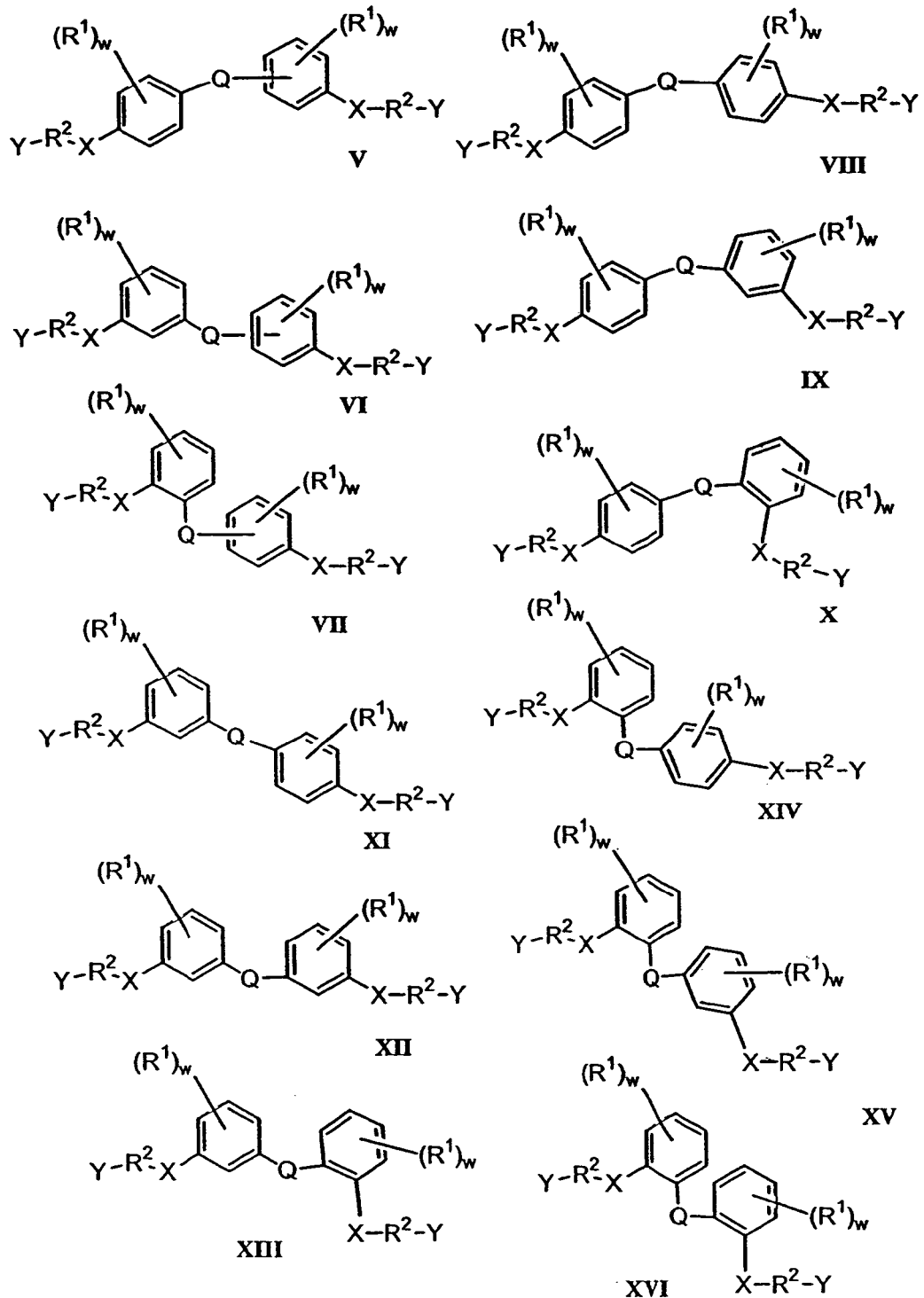
FIGS. 1–3 illustrate compounds of formulae V–XXX that are compounds of the invention.

When describing the compounds, compositions and methods of the invention, the following terms have the following meanings, unless otherwise indicated.

The term "alkyl" refers to a monovalent saturated hydrocarbon group which may be linear or branched or combinations thereof. Such alkyl groups preferably contain from 1 to 20 carbon atoms; more preferably, from 1 to 10 carbon atoms; and still more preferably, from 1 to 6 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl" refers to a monovalent unsaturated hydrocarbon group containing at least one carbon-carbon double bond, typically 1 or 2 carbon-carbon double bonds, and which may be linear or branched or combinations thereof. Such alkenyl groups preferably contain from 2 to 20 carbon atoms; more preferably from 2 to 10 carbon atoms; and still more preferably, from 2 to 6 carbon atoms. Representative alkenyl groups include, by way of example, vinyl, allyl, isopropenyl, but-2-enyl, n-pent-2-enyl, n-hex-2-enyl, n-hept-2-enyl, n-oct-2-enyl, n-non-2-enyl, n-dec-4-enyl, n-dec-2,4-dienyl and the like.

The term "alkynyl" refers to a monovalent unsaturated hydrocarbon group containing at least one carbon-carbon triple bond, typically 1 carbon-carbon triple bond, and which may be linear or branched or combinations thereof. Such alkynyl groups preferably contain from 2 to 20 carbon atoms; more preferably from 2 to 10 carbon atoms; and still more preferably, from 2 to 6 carbon atoms. Representative alkynyl groups include, by way of example, ethynyl, propargyl, but-2-ynyl and the like.

The term "alkoxy" refers to a group of the formula —OR, where R is an alkyl group as defined herein. Representative alkoxy groups include, by way of example, methoxy, ethoxy, n-propoxy, isopropoxy, n-butoxy, sec-butoxy, isobutoxy, tert-butoxy, n-pentoxy, n-hexoxy and the like.

The term "alkylene" refers to a divalent saturated hydrocarbon group which may be linear or branched or combinations thereof. Such alkylene groups preferably contain from 1 to 20 carbon atoms; more preferably, from 1 to 10 carbon atoms; and still more preferably, from 1 to 6 carbon atoms. Representative alkylene groups include, by way of example, methylene, ethylene, propylene and the like.

The term "cycloalkyl" refers to a monovalent saturated carbocyclic group which may be monocyclic or multicyclic. Each ring of such cycloalkyl groups preferably contains from 3 to 10 carbon atoms. This term also includes cycloalkyl groups fused to an aryl or heteroaryl group in which the point of attachment is on the non-aromatic (cycloalkyl) portion of the group. Representative cycloalkyl groups include, by way of example, cyclopropyl, cyclobutyl, cyclopentyl, cyclohexyl, cycloheptyl, cyclooctyl, 1,2,3,4-tetrahydronaphth-2-yl, decahydronaphthyl, indan-1-yl, adamantyl, norbornyl and the like.

The term "aryl" refers to a monovalent unsaturated aromatic carbocyclic group which may be monocyclic or multicyclic (i.e., fused). Such aryl groups preferably contain from 6 to 20 carbon atoms; more preferably, from 6 to 10 carbon atoms. This term also includes aryl groups fused to a cycloalkyl or heterocyclyl group in which the point of attachment is on the aromatic (aryl) portion of the group. Representative aryl groups include, by way of example, phenyl, napthyl, azulenyl, indan-5-yl, 1,2,3,4-tetrahydronaphth-6-yl, 2,3-dihydrobenzofuran-5-yl and the like.

The term "heteroaryl" refers to a monovalent aromatic group which contains at least one heteroatom, preferably 1 to 4 heteroatoms, selected from N, S and O within at least one aromatic ring and which may be monocyclic or multicyclic (i.e., fused). Such heteroaryl groups preferably contain from 5 to 20 atoms; more preferably, from 5 to 10 atoms. This term also includes heteroaryl groups fused to a cycloalkyl or heterocyclyl group in which the point of attachment is on the aromatic (heteroaryl) portion of the group. Representative heteroaryl groups include, by way of example, pyrroyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like.

The term "heterocyclyl" or "heterocyclic" refers to a monovalent saturated or partially unsaturated cyclic non-aromatic group which contains at least one heteroatom, preferably 1 to 4 heteroatoms, selected from N, S and O within at least one cyclic ring and which maybe monocyclic or muliticyclic. Such heterocyclyl groups preferably contain from 3 to 20 atoms; more preferably, from 3 to 10 atoms. The point of attachment of the heterocyclyl group may be a carbon or nitrogen atom. This term also includes heterocyclyl groups fused to an aryl or heteroaryl group in which the point of attachment is on the non-aromatic (heterocyclyl) portion of the group. Representative heterocyclyl groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl and the like.

The term "halo" refers to a fluoro, chloro, bromo or iodo.

The term "oxo" refers to a group of the formula =O.

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids. Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylaamine, 2-diethylaminoethanol, 2-dimethylaminoethanol, ethanolamine, ethylenediamine, N-ethylmorpholine, N-ethylpiperidine, glucamine, glucosanine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, benzenesulfonic, benzoic, camphosulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The phrase "disease or condition associated with sodium channel activity" includes all disease states and/or conditions that are acknowledged now, or that are found in the future, to be associated with the activity of sodium channels. Such disease states include, but are not limited to, pathophysiological disorders, including hypertension, cardiac arrhythmogenesis, insulin-dependent diabetes, non-insulin dependent diabetes mellitus, diabetic neuropathy, seizures, tachycardia, ischemic heart disease, cardiac failure, angina, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, cerebrovascular ischemia, CNS diseases, epilepsy, Parkinson's disease, asthma, incontinence, urinary dysfunction, micturition disorder, irritable bowel syndrome, restenosis, sub-arachnoid hemorrhage, Alzheimers disease, drug dependence/addiction, schizophrenia, Huntington's chorea, tension-type headache, trigeminal neuralgia, cluster headache, migraine (acute and prophylaxis), inflammatory pain, neuropathic pain and depression.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, timethyl amine, diethylamine, triethylamnine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention may contain one or more chiral centers. Accordingly, the invention includes racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

Specific and preferred values listed below for radicals, substituents, and ranges, are for illustration only, they do not exclude other defined values or other values within defined ranges for the radicals and substituents A specific value for each $R^1$ is independently $C_{1-10}$ alkyl, $C_{2-10}$ alkenyl, $C_{2-10}$ alkynyl, cycloalkyl, or $R^a$.

A specific value for each $R^1$ is independently $C_{1-10}$ alkyl or halo.

A more specific value for each $R^1$ is independently methyl, ethyl, propyl, chloro, bromo, fluoro, or isopropyl.

A more specific value for each $R^1$ is independently methyl, or chloro.

A specific value for each $R^2$ is independently a covalent bond or $C_{1-10}$ alkylene.

A more specific value for each $R^2$ is independently a covalent bond, methylene, 1,2-ethylene, 1,3-propylene, (2R)-2-(methyl)ethane-1,2-diyl, (2S)2-(methyl)ethane-1,2-diyl, 1-(methyl)butane-1,4-diyl, 1-(methyl)ethane-1,2-diyl, or 2,2-(dimethyl)propane-1,3-diyl.

A specific value for each $R^2$ is independently a covalent bond, methylene, or ethylene.

A specific value for Q is —O—, —S(O)$_m$—, or —(CR$^5$R$^6$)$_p$—.

A specific value for Q is —O—, —S(O)$_m$—, or —N(R$^k$)—.

A specific value for Q is —(CR$^5$R$^6$)$_p$—, or —O(CR$^5$R$^6$)$_r$O—.

A specific value for Q is —O—, —S(O)$_m$—, —(CR$^5$R$^6$)$_p$—, or —N(R$^k$)—;

A more specific value for Q is methylene, 1,2-ethylene, 3,4-hexylene, dimethylmethylene, oxy, —NH—, —OCH$_2$CH$_2$O—, or a group —C(R$^5$)(R$^6$)— wherein R$^5$ and R$^6$ together with the carbon to which they are attached form a cyclohexylene ring.

A specific value for X is oxy.

A specific value for X is —NH—.

A specific value for each Y is independently NR"R$^p$.

A specific value for each Y is independently a heterocyclyl containing at least one nitrogen atom, wherein each nitrogen of the heterocyclyl is substituted with R$^3$ or linked to R$^2$, and wherein each heterocycle of Y is optionally substituted with 1, 2, 3, or 4 substituents independently selected from R$^4$.

A specific value for each Y is independently a heterocyclyl containing at least one nitrogen atom, wherein each nitrogen of the heterocyclyl is substituted with R$^3$.

A specific value for each Y is independently a heterocyclyl containing at least one nitrogen atom, wherein each nitrogen of the heterocyclyl is linked to R$^2$, and wherein each heterocycle of Y is optionally substituted with 1, 2, 3, or 4 substituents independently selected from R$^4$.

A specific value for each Y is independently a heterocyclyl selected from pyrrolidinyl, piperidinyl, and morpholinyl, wherein each heterocycle of Y is optionally substituted with 1, 2, 3, or 4 substituents independently selected from R$^4$.

A specific value for each Y is independently a heterocyclyl selected from pyrrolidino, piperidino, and morpholino, wherein each heterocycle of Y is optionally substituted with 1, 2, 3, or 4 substituents independently selected from R$^4$.

A more specific value for each Y is independently amino, diethylamino, dimethylamino, 1-methyl-4-piperidinyl, 1-methyl-3-piperidinyl, 1-methyl-2-piperidinyl, 4-piperidinyl, 3-piperidinyl, 2-piperidinyl, 1-isopropyl-3-pyrrolidinyl, morpholino, (2R,4R)-2-methoxycarbonyl-4-pyrrolidinyl, 1-methyl-3-pyrrolidinyl, 1-methyl-2-pyrrolidinyl, 3-pyrrolidinyl, 2-pyrrolidinyl, 1-pyrrolidinyl, (2S,4R)-2-methyl-4-pyrrolidinyl, (2R,4R)-2-carboxy-4-pyrrolidinyl, (2S,4S)-2-(N,N-dimethylamino)carbonyl-4-pyrrolidinyl, (2R,4R)-2-hydroxymethyl-4-pyrrolidinyl, or (2R,4R)-2-methoxymethyl-4-pyrrolidinyl.

A specific value for each w is 0.
A specific value for each w is 1.
A specific value for each w is 2.
A specific value for each y is independently 1 or 2.
A specific value for each z is independently 0, 1, or 2.

A specific group of compounds of formula I are compounds wherein each $R_2$ is independently a covalent bond or methylene; Q is SO$_2$ or —CR$^5$R$^6$—; each w is independently 0, 1, or 2; and each y is 1 or 2.

A preferred compound of formula I is a compound of formula II:

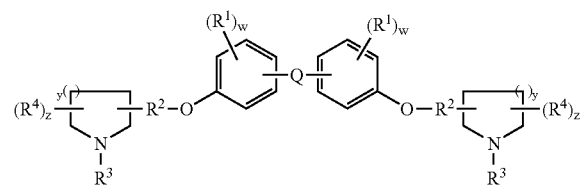

(II)

wherein:
Q is —O—, —S(O)$_m$—, or —CR$^5$R$^6$—;
each $R^1$ is independently alkyl, alkenyl, alkynyl, aryl, heteroaryl, cycloalkyl, heterocyclyl, or $R^a$;
each $R^2$ is independently a covalent bond or alkylene; wherein alkylene is optionally substituted with 1 to 4 substituents independently selected from $R^b$;
each $R^3$ is independently hydrogen, alkyl, alkenyl, alkynyl, aryl, heteroaryl, cycloalkyl, oxo, or heterocyclyl; and each $R^4$ is independently alkyl, alkenyl, alkynyl, aryl, heteroaryl, cycloalkyl, heterocyclyl, or $R^b$; or $R^3$ and $R^4$ are joined to form a $C_{1-4}$ alkylene group, wherein the alkylene group is optionally substituted with 1 to 4 substituents independently selected from $R^b$;
each $R^5$ and $R^6$ is independently hydrogen, alkyl, alkenyl, alkynyl, aryl, heteroaryl, cycloalkyl, or heterocyclyl; or $R^5$ and $R^6$ together with the carbon atom to which they are attached form a ring having from 5 to 7 ring atoms, wherein the ring optionally contains 1 or 2 heteroatoms in the ring independently selected from oxygen, sulfur and nitrogen;
wherein for $R^1$–$R^6$, each alkyl, alkenyl, and alkynyl is optionally substituted with $R^x$, or with 1 to 4 substituents independently selected from $R^b$; each aryl and heteroaryl is optionally substituted with 1 to 4 substituents independently selected from $R^c$, and each cycloalkyl and heterocyclyl is optionally substituted with 1 to 4 substituents independently selected from $R^b$ and $R^c$;
each $R^a$ is independently —OR$^d$, —NO$_2$, halo, —S(O)$_m$R$^d$, —SR$^d$, —S(O)$_2$OR$^d$, —S(O)$_m$NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(=N—OR$^e$), —CF$_3$, or —OCF$_3$;
each $R^b$ is independently $R^a$, oxo or =N—OR$^e$;

each $R^c$ is independently $R^a$, alkyl, alkenyl, or alkynyl; wherein each alkyl, alkenyl and alkynyl is optionally substituted with 1 to 4 substituents independently selected from $R^b$;

each $R^d$ and $R^e$ is independently hydrogen, alkyl, alkenyl, alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from $R^h$; or $R^d$ and $R^e$ together with the atoms to which they are attached form a heterocyclic ring having from 5 to 7 ring atoms, wherein the heterocyclic ring optionally contains 1 or 2 additional heteroatoms independently selected from oxygen, sulfur and nitrogen;

each $R^f$ and $R^g$ is independently hydrogen, alkyl, aryl, heteroaryl, cycloalkyl, or heterocyclyl; wherein each alkyl, aryl, heteroaryl, cycloalkyl and heterocyclyl is optionally substituted with 1 to 4 substituents independently selected from $R^h$; or $R^f$ and $R^g$ together with the carbon atom to which they are attached form a ring having from 5 to 7 ring atoms, wherein the ring optionally contains 1 or 2 heteroatoms independently selected from oxygen, sulfur and nitrogen;

each $R^h$ is independently halo, $C_{1-6}$ alkyl, $C_{1-6}$ alkoxy, aryl, (aryl)-$C_{1-6}$ alkyl, heteroaryl, (heteroaryl)-$C_{1-6}$ alkyl, hydroxy, amino, —NH$C_{1-6}$ alkyl, —N($C_{1-6}$ alkyl)$_2$, —OC(O)$C_{1-6}$ alkyl, —C(O)$C_{1-6}$ alkyl, —C(O)O$C_{1-6}$ alkyl, —NHC(O)$C_{1-6}$ alkyl, —C(O)NH$C_{1-6}$ alkyl, carboxy, nitro, —CN, or —CF$_3$; and each $R^x$ is independently aryl, heteroaryl, cycloalkyl or heterocyclyl; wherein each aryl or heteroaryl is optionally substituted with 1 to 4 substituents selected from the group consisting of $R^c$, and wherein each cycloalkyl and heterocyclyl is optionally substituted with 1 to 4 substituents selected from $R^b$;

m is 0, 1, or 2;
n is an integer from 1 to 10;
each w is independently 0, 1, 2, 3, or 4;
each y is independently 0, 1, 2, or 3; and
each z is independently 0, 1, 2, 3, or 4;
or a pharmaceutically-acceptable salt thereof.

Specifically, for a compound of formula II, each $R^1$ can independently be $C_{1-10}$ alkyl, $C_{2-10}$ alkenyl, $C_{2-10}$ alkynyl, cycloalkyl, or $R^a$.

Specifically, for a compound of formula II, each $R^1$ can independently be $C_{1-10}$ alkyl or halo.

Specifically, for a compound of formula II, each $R^1$ can independently be methyl, ethyl, propyl, chloro, bromo, fluoro, or isopropyl.

Specifically, for a compound of formula II, each $R^2$ can independently be a covalent bond or $C_{1-10}$ alkylene.

Specifically, for a compound of formula II, each $R^2$ can independently be a covalent bond, methylene, ethylene, propylene, or isopropylene.

Specifically, for a compound of formula II, each $R^3$ can independently be hydrogen, $C_{1-10}$ alkyl, or oxo.

Specifically, for a compound of formula II, each $R^3$ can independently be hydrogen, methyl, ethyl, propyl, isopropyl, benzyl, phenethyl, or pyridylmethyl.

Specifically, for a compound of formula II, each $R^3$ can independently be hydrogen, methyl, ethyl, propyl, or isopropyl.

Specifically, for a compound of formula II, each $R^4$ can independently be $C_{1-10}$ alkyl, $C_{2-10}$ alkenyl, $C_{2-10}$ alkynyl, or $R^b$.

Specifically, for a compound of formula II, $R^3$ and $R^4$ can be joined to form a $C_{1-4}$ alkylene group, wherein the alkylene group is optionally substituted with 1 to 4 substituents independently selected from $R^b$.

Specifically, for a compound of formula II, Q can be SO$_2$ or —CR$^5$R$^6$—.

Specifically, for a compound of formula II, each each $R^5$ and $R^6$ can independently be hydrogen, or $C_{1-10}$ alkyl.

Specifically, for a compound of formula II, $R^5$ and $R^6$ together with the carbon atom to which they are attached can form a ring having from 5 to 7 ring atoms, wherein the ring optionally contains 1 or 2 heteroatoms in the ring independently selected from oxygen, sulfur and nitrogen.

Specifically, for a compound of formula II, each $R^1$ and $R^5$ together with the carbon atom to which they are attached can form a carbocyclic ring having from 5 to 7 atoms.

Specifically, for a compound of formula II, each w can be 0.

Specifically, for a compound of formula II, each each w can be 1.

Specifically, for a compound of formula II, each w can be 2.

Specifically, for a compound of formula II, each y can independently be 1 or 2.

Specifically, for a compound of formula II, each z can independently be 0, 1, or 2.

A specific compound of formula II is a compound wherein $R_2$ is a covalent bond or methylene; Q is SO$_2$ or —CR$^5$R$^6$—; each w is independently 0, 1, or 2; and each y is 1 or 2.

A specific compound of formula II is-a compound of formula III:

(III)

wherein

Q is —O—, —S(O)$_m$—, or —CR$^5$R$^6$—;

each $R^7$ is independently hydrogen, $C_{1-10}$ alkyl, $C_{2-10}$ alkenyl, $C_{2-10}$ alkynyl, cycloalkyl, or $R^a$;

each $R^2$ is independently a covalent bond or $C_{1-6}$ alkylene; wherein alkylene is optionally substituted with 1 to 4 substituents independently selected from $R^b$;

each $R^3$ is independently hydrogen, $C_{1-10}$ alkyl, or oxo (forming an N-oxide);

each $R^5$ and $R^6$ is independently hydrogen or $C_{1-10}$ alkyl; or $R^5$ and $R^6$ together with the carbon atom to which they are attached form a ring having from 5 to 7 ring atoms, wherein the ring optionally contains 1 or 2 heteroatoms in the ring independently selected from oxygen, sulfur and nitrogen;

wherein for $R^3$, $R^5$, $R^6$, and $R^7$, each alkyl, alkenyl, and alkynyl is optionally substituted with $R^x$, or with 1 to 4 substituents independently selected from $R^b$; and each cycloalkyl is optionally substituted with 1 to 4 substituents independently selected from $R^b$ and $R^c$;

each $R^a$ is independently —OR$^d$, —NO$_2$, halo, —S(O)$_m$R$^d$, —SR$^d$, —S(O)$_2$OR$^d$, —S(O)$_m$NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(=N—OR$^e$), —CF$_3$, or —OCF$_3$;

each $R^b$ is independently $R^a$, oxo or =N—OR;

each $R^c$ is independently $R^a$, $C_{1-10}$ alkyl, $C_{2-10}$ alkenyl, or $C_{2-10}$ alkynyl; wherein each alkyl, alkenyl and alkynyl is optionally substituted with 1 to 4 substituents independently selected from $R^b$;

each $R^d$ and $R^e$ is independently hydrogen, $C_{1-10}$ alkyl, $C_{2-10}$ alkenyl, $C_{2-10}$ alkynyl, aryl, heteroaryl, cycloalkyl, or heterocyclyl; wherein each alkyl, alkenyl, alkynyl, aryl, heteroaryl, cycloalkyl and heterocyclyl is optionally substituted with 1 to 4 substituents independently selected from $R^h$; or $R^d$ and $R^e$ together with the atoms to which they are attached form a heterocyclic ring having from 5 to 7 ring atoms, wherein the heterocyclic ring optionally contains 1 or 2 additional heteroatoms independently selected from oxygen, sulfur and nitrogen;

each $R^f$ and $R^g$ is independently hydrogen, $C_{1-10}$ alkyl, aryl, heteroaryl, cycloalkyl, or heterocyclyl; wherein each alkyl, aryl, heteroaryl, cycloalkyl and heterocyclyl is optionally substituted with 1 to 4 substituents independently selected from $R^h$; or $R^f$ and $R^g$ together with the carbon atom to which they are attached form a ring having from 5 to 7 ring atoms, wherein the ring optionally contains 1 or 2 heteroatoms independently selected from oxygen, sulfur and nitrogen;

each $R^h$ is independently halo, $C_{1-6}$ alkyl, $C_{1-6}$ alkoxy, aryl, (aryl)-$C_{1-6}$ alkyl, heteroaryl, (heteroaryl)-$C_{1-6}$ alkyl, hydroxy, amino, —NH$C_{1-6}$ alkyl, —N($C_{1-6}$ alkyl)$_2$, —OC(O)$C_{1-6}$ alkyl, —C(O)$C_{1-4}$ alkyl, —C(O)O$C_{1-6}$ alkyl, —NHC(O)$C_{1-6}$ alkyl, —C(O)NH$C_{1-6}$ alkyl, carboxy, nitro, —CN, or —CF$_3$; and each $R^x$ is independently aryl, heteroaryl, cycloalkyl or heterocyclyl; wherein each aryl or heteroaryl is optionally substituted with 1 to 4 substituents selected from the group consisting of $R^c$, and wherein each cycloalkyl and heterocyclyl is optionally substituted with 1 to 4 substituents selected from $R^b$; and each y is independently 1, 2, or 3;

or a pharmaceutically-acceptable salt thereof

Specifically, each $R^7$ can independently be hydrogen, $C_{1-10}$ alkyl or halo.

Specifically, each $R^7$ can independently be methyl, ethyl, propyl, chloro, bromo, fluoro, or isopropyl.

Figure 2:
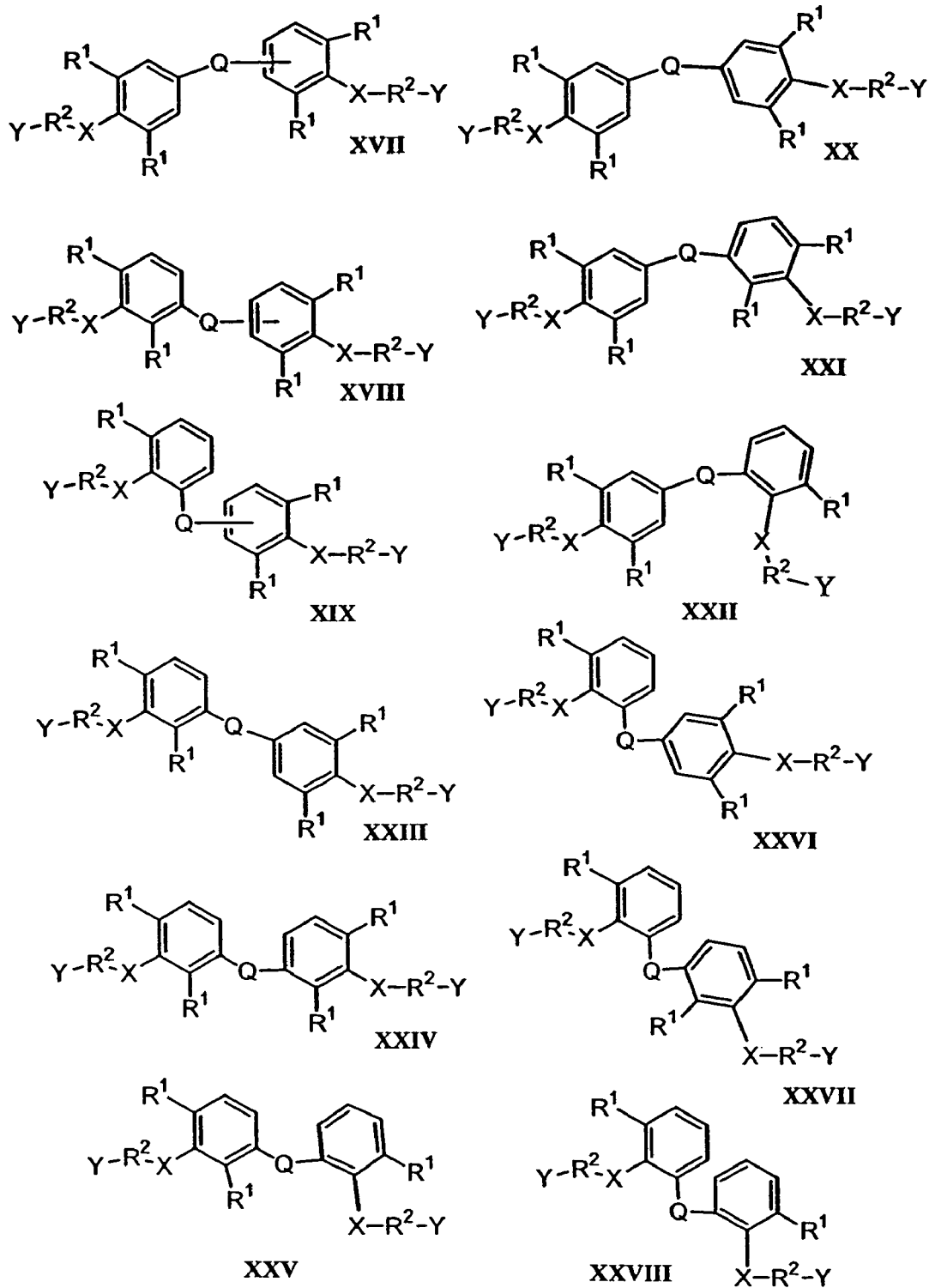
Figure 3:
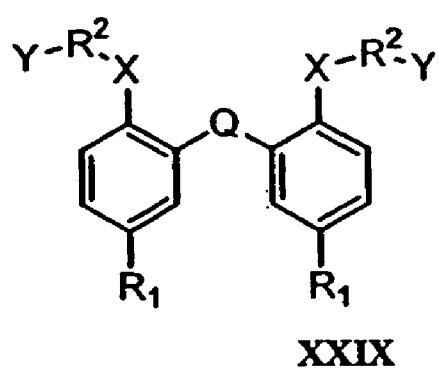
Figure 3:
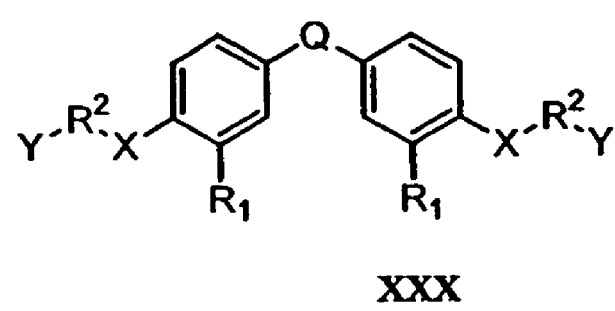

A specific compound of formula I is a compound of any one of formulae V–XXX, shown in FIGS. 1–3, wherein X, Y, Q, $R^1$, $R^2$, and w have any of the values, specific values, or preferred values defined herein.

For a compound of any one of formulae V–XXX, a specific value for $R^1$ is methyl, or chloro.

For a compound of any one of formulae V–XXX, a specific value for Q is methylene, 1,2-ethylene, 3,4-hexylene, dimethylmethylene, oxy, —NH—, —OCH$_2$CH$_2$O—, or a group —C($R^5$)($R^6$)— wherein $R^5$ and $R^6$ together with the carbon to which they are attached form a cyclohexylene ring.

For a compound of any one of formulae V–XXX, a specific value for X is oxy or —NH—.

For a compound of any one of formulae V–XXX, a specific value for $R^2$ is a covalent bond, methylene, 1,2-ethylene, 1,3-propylene, (2R)2-(methyl)ethane-1,2-diyl, (2S)-2-(methyl)ethane-1,2-diyl, 1-(methyl)butane- 1,4-diyl, 1-methyl)ethane-1,2-diyl, or 2,2-(dimethyl)propane-1,3-diyl.

For a compound of any one of formulae V–XXX, a specific value for Y is amino, diethylamino, dimethylamino, 1-methyl-4-piperidinyl, 1-methyl-3-piperidinyl, 1-methyl-2-piperidinyl, 4-piperidinyl, 3-piperidinyl, 2-piperidinyl, 1-isopropyl-3-pyrrolidinyl, morpholino, (2R,4R)-2-methoxycarbonyl-4-pyrrolidinyl, 1-methyl-3-pyrrolidinyl, 1-methyl-2-pyrrolidinyl, 3-pyrrolidinyl, 2-pyrrolidinyl, 1-pyrrolidinyl, (2S,4R)-2-methyl-4-pyrrolidinyl, (2R,4R)-2-carboxy-4-pyrrolidinyl, (2S,4S)-2-(N,N-dimethylamino)carbonyl-4-pyrrolidinyl, (2R,4R)-2-hydroxymethyl-4-pyrrolidinyl, or (2R,4R)-2-methoxymethyl-4-pyrrolidinyl.

A preferred compound of the invention is a compound of any one of formulae V–XXX, wherein each $R^1$ is independently methyl, or chloro; Q is methylene, 1,2-ethylene, 3,4-hexylene, dimethylmethylene, oxy, —NH—, —OCH$_2$CH$_2$O—, or a group —C($R^5$)($R^6$)— wherein $R^5$ and $R^6$ together with the carbon to which they are attached form a cyclohexylene ring; each X is independently oxy or —NH—; each $R^2$ is independently a covalent bond, methylene, 1,2-ethylene, 1,3-propylene, (2R)-2-(methyl)ethane-1,2-diyl, (2S)-2-(methyl)ethane-1,2-diyl, 1-(methyl)butane-1,4-diyl, 1-(methyl)ethane-1,2-diyl, or 2,2-(dimethyl)propane-1,3-diyl; and each Y is independently amino, diethylamino, dimethylamino, 1-methyl-4-piperidinyl, 1-methyl-3-piperidinyl, 1-methyl-2-piperidinyl, 4-piperidinyl, 3-piperidinyl 2-piperidinyl, 1-isopropyl-3-pyrrolidinyl, morpholino, (2R,4R)-2-methoxycarbonyl-4-pyrrolidinyl, 1-methyl-3-pyrrolidinyl, 1-methyl-2-pyrrolidinyl, 3-pyrrolidinyl, 2-pyrrolidinyl, 1-pyrrolidinyl, (2S,4R)-2-methyl-4-pyrrolidinyl, (2R,4R)-2-carboxy-4-pyrrolidinyl, (2S,4S-2-(N,N-dimethylamino)carbonyl-4-pyrrolidinyl, (2R,4R)-2-hydroxymethyl-4-pyrrolidinyl, or (2R,4R)-2-methoxymethyl-4-pyrrolidinyl.

Another preferred compound of formula I is a compound of formula XX:

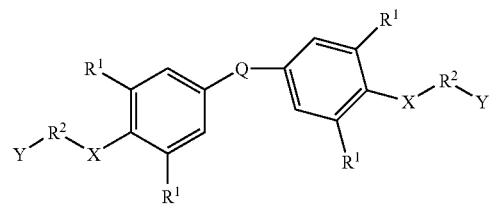

(XX)

wherein Q is methylene, 1,2-ethylene, 3,4-hexylene, dimethylmethylene, oxy, or a group —C($R^5$)($R^6$)— wherein $R^5$ and $R^6$ together with the carbon to which they are attached form a cyclohexylene ring. Preferably, for a compound of formula XX, each $R^1$ is independently methyl or chloro.

Another preferred compound of formula I is a compound of formula XXIX:

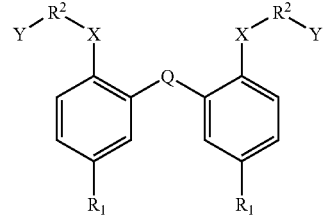

(XXIX)

wherein Q is methylene. Preferably, for a compound of formula XXIX, each $R^1$ is independently chloro.

Another preferred compound of formula I is a compound of formula XXX:

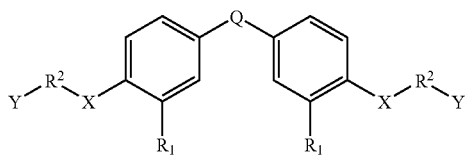

(XXX)

wherein Q is methylene. Preferably, for a compound of formula XXX, each $R^1$ is chloro.

General Synthetic Procedures

The compounds of the invention can be prepared using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

Processes for preparing compounds of formula I are provided as further embodiments of the invention and are illustrated by the following procedures in which the meanings of the generic radicals are as given above unless otherwise qualified. For example, a compound of formula I (wherein each X is oxy) an be prepared from an intermediate diol of formula (I) by condensation with two equivalents of the alcohol ROH, as illustrated in the following scheme.

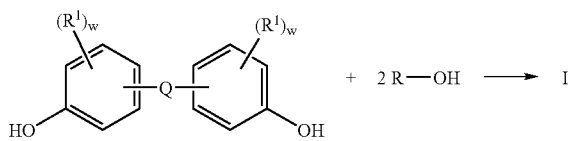

(IV)

reagents and conditions suitable for preparing this bis-ether of formula I from the diol of formula IV are well known in the art. For example, the reaction can conveniently be carried out under conditions similar to those described in the Examples below.

Pharmaceutical Compositions

The invention also provides pharmaceutical compositions comprising a compound of the invention. Accordingly, the compound, preferably in the form of a pharmaceutically acceptable salt, can be formulated for oral or parenteral administration for the therapeutic or prophylactic treatment of diseases or conditions associated with sodium channel activity.

By way of illustration, the compound can be admixed with conventional pharmaceutical carriers and excipients and used in the form of tablets, capsules, elixirs, suspensions, syrups, wafers, and the like. Such pharmaceutical compositions will contain from about 0.1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991. Such patches may be constructed for continuous, pulsatile, or on demand delivery of pharmaceutical agents.

The active compound is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day.

In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

According to the invention, a compound can be administered in a single daily dose or in multiple doses per day. The treatment regimen may require administration over extended periods of time, for example, for several days or for from one to six weeks.

Suitable formulations for use in the present invention can be found in *Remington's Pharmaceutical Sciences*, Mace Publishing Company, Philadelphia, Pa., 17th ed. (1985). The following non-limiting examples illustrate representative pharmaceutical compositions of the invention.

Formulation Example A

This example illustrates the preparation of a representative pharmaceutical composition for oral administration of a compound of this invention:

| Ingredients | Quantity per tablet, (mg) |
|---|---|
| Active Compound | 200 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of a compound of this invention:

| Ingredients | Quantity per tablet, (mg) |
|---|---|
| Active Compound | 400 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of a compound of this invention.

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 mL |

Formulation Example D

This example illustrates the preparation of a representative pharmaceutical composition containing a compound of this invention.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 mL |
| HCl (1 N) | q.s. to pH 4 |
| Water (distilled, sterile) | q.s. to 20 mL |

Formulation Example E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection

Formulation Example F

This example illustrates the preparation of a representative pharmaceutical composition containing a compound of this invention.

An injectable preparation is prepared having the following composition:

| Ingredients | |
| --- | --- |
| Active Compound | 0.1–5.0 g |
| Hydroxypropyl-β-cyclodextrin | 1–25 g |
| 5% Aqueous Dextrose Solution (sterile) | q.s. to 100 mL |

The above ingredients are blended and the pH is adjusted to 3.5±0.5 using 0.5 N HCl or 0.5 N NaOH.

Formulation Example G

This example illustrates the preparation of a representative pharmaceutical composition for topical application of a compound of this invention.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example H

This example illustrates the preparation of a representative pharmaceutical composition containing a compound of this invention.

A suppository totaling 2.5 grams is prepared having the following composition:

| Ingredients | |
| --- | --- |
| Active Compound | 500 mg |
| Witepsol H-15* | balance |

(*triglycerides of saturated vegetable fatty acid; a product of Riches-Nelson, Inc., New York, N.Y.)

Utility

The compounds of this invention, and their pharmaceutically acceptable salts, exhibit biological activity and are useful for medical treatment. The ability of a compound to block sodium channel activity or to treat neuropathic pain can be demonstrated using the tests described herein, or can be demonstrated using tests that are known in the art.

The following synthetic and biological examples are offered to illustrate the invention, and are not to be construed in any way as limiting the scope of the invention.

EXAMPLES

In the examples below, the following abbreviations have the following meanings. Any abbreviations not defined have their generally accepted meaning. Unless otherwise stated, all temperatures are in degrees Celsius.

BOC, Boc=tert-butoxycarbonyl
DCM=dichloromethane
DMSO=dimethyl sulfoxide
EtOAc=ethyl acetate
HATU=O-(7-azabenzotriazol-1-yl)-N,N,N',N'-tetramethyluronium hexafluorophosphate
HOAT=1-hydroxy-7-azabenzotriazole
TFA=trifluoroacetic acid
THF=tetrahydrofuran
MeCN=acetonitrile
$MgSO_4$=anhydrous magnesium sulfate General: Unless noted otherwise, reagents, starting material (including amino alcohols, and bis-phenols) and solvents were purchased from commercial suppliers (Aldrich, Fluka, Sigma, and etc.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent ($CD_3OD$ or $CDCl_3$), and spectra were acquired with a Varian Gemini 2000 instrument (300 MHz) under standard parameters; and mass spectrometric identification was performed by an electrospray ionization method (ESMS) with a Perkin Elmer instrument (PE SCIEX API 150 EX).

Analytical HPLC: Crude compound was dissolved in 50% MeCN/$H_2O$ (with 0.1% TFA) at 0.5–1.0 mg/mL concentration, and analyzed using a reverse-phased analytical column (Agilent Zorbax Bonus-RP, 2.1×50 mm, ID=5 μm); at a flow rate of 0.5 mL/min; with 10% MeCN/$H_2O$ (0.1% TFA) as a solvent (0–0.5 min) (10 to 70% linear gradient, 0.5–5 min); and UV detection at 214, 254, and 280 nm.

Preparative HPLC purification: Crude compound was dissolved in 50% MeCN/$H_2O$ (with 0.1% TFA) at 30–45 mg/mL concentration, filtered, and injected onto a reversed phase column (YMC Pack-Pro C18, 50a×20 mm, ID=5 μm); with a linear solvent gradient: 10 to 60% MeCN (0.1% TFA)/H$_2$O (0.1% TFA) over 50 min; at a flow rate of 40 mL/min; with UV detection at 214, 254, or 280 nm.

General Procedure A

N-Boc Protected Amino Alcohols

N-Boc-amino alcohols were prepared from the corresponding amino alcohol by treating with di-tert-butyl-dicarbonate ((Boc)$_2$O) in CH$_2$Cl$_2$ or methanol under standard conditions such as those described in the following representative example.

To a cold solution of methanol (300 mL) containing 3-(hydroxy-methyl)piperidine (25 g, 217 mmole) cooled with ice bath was added (Boc)$_2$O (57 g, 261 mmole) under stream of nitrogen. The reaction mixture was stirred and allowed to warm gradually to room temperature. After stirring overnight, the mixture was concentrated in vacuo, yielding an oily residue that was partitioned between EtOAc (250 mL) and 0.1 M NaOH (250 mL). The organic phase was collected, and dried over MgSO$_4$. The solution was passed through silica gel column (dry volume of 200 mL), followed by rinsing with EtOAc (500 mL). The filtrates were combined, and concentrated in vacuo, to give white crystals, which were washed with hexanes (200 mL), and dried in air to afford N-Boc-(3-hydroxymethyl)-piperidine (43.3 g, ~93%).

Example 1

Preparation of Compound 1

To a stirred cold solution of THF containing 4,4'-methylene-bis(2,6-dimethylphenol) (1.54 g, 6 mmol), N-Boc-3-pyrrolidinol (2.42 g, 13 mmol), and triphenylphosphine (3.41 g, 13 mmol) at 0° C., under nitrogen atmosphere, was added dropwise a solution of diethylazo-dicarboxylate (DEAD; 2.05 mL, 13 mmol) in THF. The mixture was allowed to return gradually to ambient temperature, where stirring continued for 20 hours. After concentrating the mixture in vacuo, the residue was taken up in dichloromethane (40 mL), and cooled to 0° C. While stirring under nitrogen atmosphere, trifluoroacetic acid (10 mL) was added dropwise. The mixture was returned to ambient temperature and stirred for 2 hours. The mix was then concentrated in vacuo, and partitioned between ethyl acetate (75 mL) and 1N HCl (15 mL) in a separatory funnel. After gentle shaking, the aqueous layer was collected, filtered, and fractionated by preparative HPLC. Appropriate fractions of the desired product were combined and lyophilized to afford the title compound as its TFA salt. ESMS (C$_{25}$H$_{34}$N$_2$O$_2$): calcd. 394.5572; obsd. 395.3 [M+H]$^+$. Retention time (anal. HPLC: 10–70% MeCN/H$_2$O over 5 min)=2.61 min. $^1$H-NMR (CD$_3$OD, 299.96 MHz): δ (ppm) 6.83 (s, 4H), 4.74 (m, 2H), 3.74 (s, 2H), 3.20–3.61 (m, 8H), 2.22–2.37 (m, 2H), 2.21 (s, 12H), 2.02–2.19 (m, 2H).

Example 2

Preparation of Compound 2

To a stirred, cold solution of TBF (20 mL) containing 4,4'-methylene-bis(2,6-dimethylphenol) (0.55 g, 2.15 mmol), N-Boc-3-(hydroxymehtyl)-piperidine (1.0 g, 4.64 mmol), and triphenylphosphine (1.18 g, 4.50 mmol) in ice bath, was added dropwise diethyl azodicarboxylate (DEAD; 0.79 g, 4.54 mmol) in THF (5 mL). The mixture was stirred at 0° C. for 2 hours, and was allowed to warm to ambient temperature where it was stirred for 12 hours. After concentration in vacuo, the residue was dissolved in EtOAc (100 mL) and washed with 0.1 M NaOH (2×100 mL). The organic phase was dried over MgSO$_4$, and concentrated in vacuo to afford colorless oil.

Deprotection of N-Boc group of the product was performed by treating with TFA. It was dissolved in CH$_2$CL$_2$ (10 mL), cooled in ice bath, and treated slowly with CF$_3$CO$_2$H (10 mL) under nitrogen atmosphere. The mixture was stirred for 2 hours in ice bath, and concentrated to oily residue. It was partitioned between EtOAc (150 mL) and 1.0 M NaOH (150 mL). The organic phase was dried over MgSO$_4$, and concentrated. The resulting oily product was purified by flash silica column chromatography, eluting with 50% EtOAc/hexanes to 5% i-PrNH$_2$/10% MeOH/50% EtOAc/hexanes, to provide the title compound (540 mg). ESMS (C$_{29}$H$_{42}$N$_2$O$_2$): calcd. 450.66; obsd. 451.4 [M+H]$^+$. Thin layer chromatography: R$_f$=0.14 (5% i-PrNH$_2$/50% EtOAc/Hexanes; silica TLC).

Examples 3–12

Unless otherwise noted, compounds 3–12 were prepared using a procedure similar to that described in Example 1, except replacing the N-Boc-3-pyrrolidinol used therein with the requsite alcohol.

Example 3

Compound 3 was prepared using N-Boc-4-hydroxypiperidine. ESMS (C$_{27}$H$_{38}$N$_2$O$_2$): calcd. 422.61; obsd. 423.2 [M+H]$^+$. HPLC: Retention time (anal. HPLC: 10–70% MeCN/H$_2$O over 5 min)=2.75 min.

Example 4

Compound 4 was prepared using (R)N-Boc-3-hydoxypyrrolidne. ESMS (C$_{25}$H$_{34}$N$_2$O$_2$): calcd. 394.5572; obsd. 395.3 [M+H]$^+$. Retention time (anal. HPLC: 10–70% MeCN/H$_2$O over 5 min)=2.61 min.

Example 5

Compound 5 was prepared using (S)-N-Boc-3-hydoxypyrrolidine. ESMS: (C$_{25}$H$_{34}$N$_2$O$_2$).calcd. 394.5572; obsd. 395.3 [M+H]$^+$. Retention time (anal. HPLC: 10–70% MeCN/H$_2$O over 5 min)=2.61 min.

Example 6

Compound 6 was prepared using N-methyl-2-(2-hydroxyethyl)pyrrolidine (without treatment with TFA). ESMS (C$_{31}$H$_{46}$N$_2$O$_6$): calcd. 478.7; obsd. 479.3 [M+H]$^+$. Retention time (anal. HPLC: 10–70% MeCN/H$_2$O over 5 min)=3.1 min.

Example 7

Compound 7 was prepared using N-Boc-2-(2-hydroxyethyl)piperidine. ESMS (C$_{31}$H$_{46}$N$_2$O$_2$): calcd. 478.7; obsd. 479.3 [M+H]$^+$. Retention time (anal. HPLC: 10–70% MeCN/H$_2$O over 5 min)=3.2 min.

Example 8

Compound 8 was prepared from the mono-adduct isolated from the synthesis of compound 5 using N-Boc-(R)-3-pyrrolidinol. ESMS ($C_{25}H_{34}N_2O_2$): calcd. 394.5572; obsd. 395.3 [M+H]$^+$. Retention time (anal. HPLC: 10–70% MeCN/H$_2$O over 5 min)=2.61 min.

Example 9

Compound 9 was prepared using N-methyl-3-hydroxypyrrolidine (except treatment with TFA). ESMS ($C_{27}H_{38}N_2O_2$): calcd. 422.611; obsd. 423.1 [M+H]$^+$. Retention time (anal. HPLC: 10–70% MeCN/H$_2$O over 5 min)=2.57 min.

Example 10

Compound 10 was prepared using 1-methyl-2-piperidinemethanol. ESMS ($C_{31}H_{46}N_2O_2$): calcd. 478.7185; obsd. 479.4 [M+H]$^+$. Retention time (anal. HPLC: 10–70% MeCN/H$_2$O over 5 min)=3.09 min.

Example 11

Compound 11 was prepared using 3-hydroxyquinuclidinol. ESMS ($C_{31}H_{42}N_2O_2$): calcd. 474.7; obsd. 475.2 [M+H]$^+$. Retention time (anal. HPLC: 10–70% MeCN/H$_2$O over 5 min)=3 min.

Example 12

Compound 12 was prepared using N-(2-hydroxyethyl)-pyrrolidine. ESMS ($C_{29}H_{42}N_2O_2$): calcd. 450.7 ; obsd. 451.1 [M+H]$^+$. Retention time (anal. HPLC: 10–70% MeCN/H$_2$O over 5 min)=2.8 min.

Example 13

Preparation of Compound 13

To a stirred solution of THF (30 mL) containing N-Boc-3-piperidinyl-methanol (1.0 g, 4.65 mmol), bis(4-hydroxy-3,5-dimethylphenyl)sulfone (2.23 mmol), and triphenylphosphine (1.34 g, 5.11 mmol) cooled in ice bath was added diethylazadicarboxylate (0.89 g, 5.11 mmol) dropwise under nitrogen atmosphere. The reaction mixture was stirred in ice bath, and allowed to warm gradually to room temperature while stirred overnight. After quenching the reaction mixture by adding 5 mL of water, it was concentrated in vacuo. The residue was partitioned between alkaline brine (150 mL) and EtOAc (150 mL). The organic phase was collected, dried over Na$_2$SO$_4$, and evaporated in vacuo, yielding pale red solid. It was dissolved in CH$_2$Cl$_2$ (10 mL), cooled in ice bath, and treated with TFA (10 mL) under nitrogen stream. The mixture was stirred for 2 hours at 5° C. Evaporation of the solution afforded the crude product. After being solubilized in aqueous acetonitrile, the mixture was purified by preparative reversed phase HPLC to provide the title compound. Retention time (anal. HPLC: 10–70% MeCN/H$_2$O over 5 min)=2.8 min. ESMS ($C_{28}H_{40}N_2O_4S$): calcd. 500.70; obsd. 501.4 [M+H]$^+$.

Examples 14–16

Compounds 14–16 were prepared using a procedure similar to that described in Example 13, except replacing the bis(4-hydroxy-3,5-dimethylphenyl)sulfone used therein with the requsite diol.

Example 14

Compound 14 was prepared using 2,2-bis(4-hydroxy-3,5-dichlorophenyl)propane. Retention time (anal. HPLC: 10–70% MeCN/H$_2$O over 5 min)=3.55 min. ESMS ($C_{27}H_{34}N_2O_2Cl_4$): calcd. 560.39; obsd. 561.2 [M+H]$^+$.

Example 15

Compound 15 was prepared using bis(4-hydroxyphenyl)methane. Retention time (anal. HPLC: 10–70% MeCN/H$_2$O over 5 min)=2.8 min. ESMS ($C_{25}H_{34}N_2O_2$): calcd. 394.56; obsd. 395.2 [M+H]$^+$.

Example 16

Compound 16 was prepared using 4,4'-isopropylidene-bis (2,6-dimethylphenol). ESMS ($C_{31}H_{46}N_2O_2$): calcd. 478.72; obsd. 479.1 [M+H]$^+$. HPLC: Retention time (anal. HPLC: 10–70% MeCN/H$_2$O over 5 min)=3.3 min. Thin layer chromatography: R$^f$=0.17 (5% i-PrNH$_2$/10% MeOH/CH$_2$Cl$_2$).

Example 17

Preparation of Compound 17

Compound 17 was prepared using a procedure similar to that described in Example 2, except replacing the starting materials used therein with 4,4'-sulfonyl-bis(2,6-dimethylphenol) and N-Boc-4-hydroxypiperidine. ESMS ($C_{26}H_{36}N_2O_4S$): calcd. 472.65; obsd. 473.4 [M+H]$^+$. HPLC: Retention time (anal. HPLC: 10–70% MeCN/H$_2$O over 5 min) 2.4 min.

Examples 18–26

Unless otherwise noted, compounds 18–26 were prepared using a procedure similar to that described in Example 1, except replacing the starting materials used therein with the starting materials described below.

Example 18

Compound 18 was prepared from 4,4'-isopropylidenebis (2,6-dimethylphenol) and N-Boc-3-hydroxypyrrolidine. ESMS: ($C_{27}H_{38}N_2O_2$) calcd. 422.611; obsd. 423.4 [M+H]$^+$. Retention time (anal. HPLC: 10–90% MeCN/H$_2$O over 5 min)=2.60 min. $^1$H-NMR (CD30D, 299.96 MHz): δ (ppm) 6.90 (s, 4H), 4.78 (m, 2H), 3.40–3.68 (m, 8H), 2.00–2.40 (m, 16H), 1.60 (s, 6H).

Example 19

Compound 19 was prepared from 4,4'-methylene-bis(1-phenol) and N-Boc-3-hydroxypyrrolidine. ESMS ($C_{21}H_{26}N_2O$): calcd. 338.4; obsd. 339.1 [M+H]$^+$. Retention time (anal. HPLC: 10–70% MeCN/H$_2$O over 5 min)=2.1 min.

Example 20

Compound 20 was prepared from 4,4'-isopropylidenebis (2,6-dichlorophenol) and N-Boc-3-hydroxypyrrolidine. ESMS ($C_{23}H_{26}Cl_4N_2O_2$): calcd. 504.2825; obsd. 505.1 [M+H]$^+$. Retention time (anal. HPLC: 10–90% MeCN/H$_2$O over 5 min)=2.62 min.

Example 21

Compound 21 was prepared from 4,4'-sulfonylbis(2,6-dimethylphenol) and N-Boc-3-hydroxypyrrolidine. ESMS ($C_{24}H_{32}N_2O_4S$): calcd. 444.5952; obsd. 445.2[M+H]$^+$. Retention time (anal. HPLC: 10–70% MeCN/H$_2$O over 5 min)=2.19 min.

Example 22

Compound 22 was prepared from 2,2-bis(4-hydroxy-3-methylphenyl)propane and N-Boc-3-hydroxypyrrolidine. ESMS ($C_{25}H_{34}N_2O_2$): calcd. 394.6 ; obsd. 394.9 [M+H]$^+$. Retention time (anal. HPLC: 10–70% MeCN/H$_2$O over 5 min)=2.7 min.

Example 23

Compound 23 was prepared from 1,1-bis(4-hydroxyphenyl)cyclohexane and N-Boc-3-hydroxypyrrolidine. ESMS ($C_{26}H_{34}N_2O_2$): calcd. 406.6; obsd. 407.0 [M+H]$^+$. Retention time (anal. HPLC: 10–70% MeCN/H$_2$O over 5 min)=2.8 min.

Example 24

Compound 24 was prepared from bis(4-hydroxy-3,5-dimethylphenyl)sulfone and N-methyl-3-hydroxypyrrolidine. ESMS ($C_{26}H_{36}N_2O_4S$): calcd. 472.6 ; obsd. 473.1 [M+H]$^+$. Retention time (anal. HPLC: 10–70% MeCN/H$_2$O over 5 min)=2.2 min.

Example 25

Compound 25 was prepared from bis(4-hydroxy-3,5-dimethylphenyl)sulfone and N-methyl-3-hydroxymethylpiperidine. ESMS ($C_{30}H_{44}N_2O_4S$): calcd. 528.8 ; obsd. 529.2 [M+H]$^+$. Retention time (anal. HPLC: 10–70% MeCN/H$_2$O over 5 min)=2.7 min.

Example 26

Compound 26 was prepared from bis(4-hydroxy-3,5-dimethylphenyl)sulfone and N-methyl-4-hydroxypiperidine. ESMS ($C_{28}H_{40}N_2O_4S$): calcd. 500.7 ; obsd. 501.3 [M+H]$^+$. Retention time (anal. HPLC: 10–70% MeCN/H$_2$O over 5 min)=2.4 min.

Examples 27 to 39

Unless otherwise noted, compounds 27 to 39 were prepared similarly as described in Example 1, except replacing the N-Boc-3-pyrrolidinol used with the requisite alcohol.

Example 27

Compound 27 was prepared using (S)N-phthalimido-2-amino-propanol (after coupling, the phthalimide group was deprotected by treatment with hydrazine). ESMS ($C_{23}H_{34}N_2O_2$): calcd. 370.26; obsd. 371.1 [M+H]$^+$. Retention time (anal. HPLC: 10–70% MeCN/H$_2$O over 5 min)= 2.688 min. $^1$H-NMR (CD$_3$OD, 299.96 MHz): δ (ppm) 1.31 (d, impurity), 1.47 (d, 6H), 2.27 (s, 12H), 3.68–3.95 (m, 8H), 6.87 (s, 4H).

Example 28

Compound 28 was prepared using (R)-N-phthalimido-2-amino-propanol (after coupling, the phthalimide group was deprotected by treatment with hydrazine). ESMS ($C_{23}H_{34}N_2O_2$): calcd. 370.26; obsd. 371.1 [M+H]$^+$. Retention time (anal. HPLC: 10–70% MeCN/H$_2$O over 5 min)= 2.666 min. $^1$H-NMR (CD$_3$OD, 299.96 MHz): δ (ppm) 1.31 (d, impurity), 1.47 (d, 6H), 2.27 (s, 12H), 3.68–3.95 (m, 8H), 6.87 (s, 4H).

Example 29

Compound 29 was prepared using N,N-di-ethyl-5-amino-2-pentanol (without treatment with TFA). ESMS ($C_{35}H_{58}N_2O_2$): calcd. 538.45; obsd. 539.4 [M+H]$^+$. Retention time (anal. HPLC: 2–70% MeCN/H$_2$O over 4 min) =3.394 min.

Example 30

Compound 30 was prepared using N,N-di-methyl-3-amino-2,2-di-methyl-propanol (without treatment with TFA). ESMS ($C_{31}H_{50}N_2O_2$): calcd. 482.39; obsd. 483.3 [M+H]$^+$. Retention time (anal. HPLC: 2–70% MeCN/H$_2$O over 4 min)=3.225 min.

Example 31

Compound 31 was prepared using N,N-di-methyl-3-amino-2-propanol (without treatment with TFA). ESMS ($C_{27}H_{42}N_2O_2$): calcd. 426.32; obsd. 427.3 [M+H]$^+$. Retention time (anal. HPLC: 2–70% MeCN/H$_2$O over 4 min)= 3.039 min.

Example 32

Compound 32 was prepared using 4-hydroxy-N-methyl-piperidine (without treatment with TFA). ESMS ($C_{29}H_{42}N_2O_2$): calcd. 450.6648; obsd. 451.1 [M+H]$^+$. Retention time (anal. HPLC: 10–70% MeCN/H$_2$O over 5 min)=2.80 min.

Example 33

Compound 33 was prepared using N-methyl-piperidine-3-methanol (without treatment with TFA). ESMS ($C_{31}H_{46}N_2O_2$): calcd. 478.7185; obsd. 479.3 [M+H]$^+$. Retention time (anal. HPLC: 10–70% MeCN/H$_2$O over 5 min)=3.15 min.

Example 34

Compound 34 was prepared using N-isopropyl-3-pyrrolidinol (without treatment with TFA). ESMS ($C_{31}H_{46}N_2O_2$): calcd. 478.7185; obsd. 479.3 [M+H]$^+$. Retention time (anal. HPLC: 10–70% MeCN/H$_2$O over 5 min)=3.05 min.

Example 35

Compound 35 was prepared using N-methyl-2-piperidineethanol (without treatment with TFA). ESMS ($C_{33}H_{50}N_2O_2$): calcd. 506.7723; obsd. 507.3 [M+H]$^+$. Retention time (anal. HPLC: 10–70% MeCN/H$_2$O over 5 min)=3.22 min.

Example 36

Compound 36 was prepared using N,N-dimethylethanolamine (without treatment with TFA). ESMS ($C_{25}H_{38}N_2O_2$): calcd. 398.589; obsd. 399.0 [M+H]$^+$. Retention time (anal. HPLC: 10–70% MeCN/H$_2$O over 5 min)=2.65 mm.

Example 37

Compound 37 was prepared using N,N-diethylethanolamine (without treatment with TFA). ESMS ($C_{29}H_{46}N_2O_2$): calcd. 454.6965; obsd. 455.1 [M+H]$^+$. Retention time (anal. HPLC: 10–70% MeCN/H$_2$O over 5 min)=3.05 min.

Example 38

Compound 38 was prepared using 4-(2-hydroxyethyl)-morpholine (without treatment with TFA). ESMS ($C_{29}H_{42}N_2O_4$): calcd. 482.6636; obsd. 483.3 [M+H]$^+$. Retention time (anal. HPLC: 10–70% MeCN/H$_2$O over 5 min) 2.76 min.

Example 39

Compound 39 was prepared using N-Boc-4-(R)-hydroxy-(L)-proline methyl ester. ESMS ($C_{29}H_{38}N_2O_6$): calcd. 510.6306; obsd. 511.3 [M+H]$^+$. Retention time (anal. HPLC: 10–70% MeCN/H$_2$O over 5 min)=2.85 min.

Examples 40 to 48

Compounds 40 to 48 were prepared using a procedure similar to that described in Example 1. Specific changes to the synthetic procedures are described below.

Example 40

To a 0° C. solution of N-Boc-3-pyrrolidinol (37.5 mmol), 4,4'-methylene-bis(2,6-dimethylphenol) (25 mmol), and triphenylphosphine (37.5 mmol) in THF, under nitrogen atmosphere, was added diethyl azodicarboxylate (DEAD; 37.5 mmol) dropwise over 10 mins. After the ice bath was allowed to warm to rt, the reaction mixture was stirred at rt for 16 hrs. The mixture was then concentrated in vacuo, and then purified by silica gel chromatography (10:90 Ethyl Acetate: DCM), which afforded a mono ether adduct as a product. This intermediate was used as a reactant in next reaction.

To a 0° C. solution of N-isopropyl-3-hydroxypyrrolidine (25 mmol), the intermediate (10 mmol), and triphenylphosphine (25 mmol) in THF, under a nitrogen atmosphere, was added DEAD (25 mmol) dropwise over 10 mins. The reaction mixture was stirred at 0° C. for 4 hrs and at rt for 16 hrs. After concentrated, the mixture was taken up in 50 mL of DCM, chilled to 0° C., and followed by addition of 10 mL of TFA. The mix was stirred for 2 hrs, and concentrated in vacuo. The residue was taken up in 75 mL of Ethyl Acetate, and extracted into 20 mL of 1N HCl. The aqueous layer was collected, and purified by prep HPLC to afford Compound 40. ESMS ($C_{28}H_{40}N_2O_2$): calcd. 436.6379; obsd. 437.1 [M+H]$^+$. Retention time (anal. HPLC: 10–70% MeCN/H$_2$O over 5 min)=2.82 min.

Example 41

Compound 41 was prepared similarly as described for compound 40 except replacing N-isopropyl-3-pyrrolidinol with N-methyl-3-pyrrolidinol. ESMS ($C_{26}H_{36}N_2O_2$): calcd. 408.5841; obsd. 409.2 [M+H]$^+$. Retention time (anal. HPLC: 10–70% MeCN/H$_2$O over 5 min) 2.69 min.

Example 42

Paraformaldehyde (54 mg, 1.8 mmol) was added to a solution of compound 5 (AMI 7778) (186.8 mg) in ethanol before the mixture was heated at 100° C. for 30 mins. The mixture was cooled to ambient temperature and solid sodium cyanoborohydride (75.6 mg, 1.2 mmol) was added in portions. The mixture was stirred for 2 hrs at ambient temperature, and then quenched with water. The solution was concentrated under reduced pressure, and purified by prep HPLC to give compound 42. ESMS ($C_{27}H_{38}N_2O_2$): calcd. 422.611; obsd. 423.1 [M+H]$^+$. Retention time (anal. HPLC: 10–70% MeCN/H$_2$O over 5 min)=2.64 min.

Example 43

First, N-benzyl-pyrrolidine-3-methanol was prepared as follows. Methyl N-benzyl-5-oxo-pyrrolidine-3-carboxylate (11.66 g, 50 mmol) was dissolved in diethyl ether and cooled to 0° C. This solution was added to a 0° C. suspension of lithium aluminum hydride in diethyl ether under nitrogen atmosphere. After addition, the mixture was refluxed for 1 hr. and then cooled with an ice bath. To quench the reaction, sodium sulfate decahydrate was added and the mixture was stirred for 1 hr. After filtration, the filtrate was collected, and concentrated to dryness to give N-Benzyl-pyrrolidine-3-methanol. ESMS ($C_{12}H_{17}NO$): calcd. 191.13; obsd. 192–2 [M+H]$^+$. Retention time (anal. HPLC: 10–70% MeCN/H$_2$O over 5 min)=0.95 min.

To a 0° C. solution of the N-Benzyl-pyrrolidine-3-methanol (25 mmol), 4,4'-methylene-bis(2,6-dimethylphenol) (10 mmol), and triphenylphosphine (25 mmol) in THF, under nitrogen atmosphere, was added diethyl azodicarboxylate (DEAD; 25 mmol) dropwise over 10 mins. The reaction mixture was warmed up gradually to rt over 4 hr, and stirred for additional 16 hrs. The mixture was then concentrated in vacuo, and taken up in 35 mL of ethanol prior to being placed in a Parr bottle. To this solution was added wet PdOH (1 g, 20% by weight), and followed by addition of 5 mL of 6N HCl. This mixture was shaken under a 50 psi atmosphere of hydrogen for 6 days, filtered through celite, and concentrated under reduced pressure. The resulting residue was then taken up in 75 mL of ethyl acetate and extracted into 20 mL of 1N HCl. The aqueous solution was collected, and purified by prep HPLC to afford compound 43. ESMS ($C_{27}H_{38}N_2O_2$): calcd. 422.611; obsd. 423.1 [M+H]$^+$. Retention time (anal. HPLC: 10–70% MeCN/H$_2$O over 5 min)=2.95 min.

Example 44

To a 0° C. solution of N-Boc-4-(R)-hydroxy-(L)-proline methyl ester (150 mmol), 4,4'-methylene-bis-(2,6-dimethylphenol) (50 mmol), and triphenylphosphine (150 mmol) in THF, under nitrogen atmosphere, was added diethyl azodicarboxylate (DEAD; 150 mmol) dropwise over 20 mins. The reaction mixture was warmed up gradually to rt over 4 hrs, and stirred at rt for additional 16 hrs. The mixture was then concentrated and purified by silica gel chromatography (DCM:EtOAc 95:5) to afford an intermediate di-ester (I). ESMS ($C_{39}H_{54}N_2O_{10}$): calcd. 710.38; obsd. 711.5 [M+H]$^+$. Retention time (anal. HPLC: 25–95% MeCN/H$_2$O over 5 min)=4.95 min.

The intermediate I (5.7 g, 8.02 mmol) was dissolved in TBF, and placed in a nitrogen atmosphere before dropwise addition of lithium borohydride in THF (2.0 M, 12.03 mL, 24.0 6 mmol). The mixture was stirred for 15 hrs, and concentrated in vacuo, and taken up in ethyl acetate. It was washed with phosphoric acid, saturated sodium bicarbonate, and brine. After dried over sodium sulfate and filtered, the organic phase was concentrated to dryness to give an intermediate alcohol (II). ESMS ($C_{37}H_{54}N_2O_8$): calcd. 654.39; obsd. 655.1 [M+H]$^+$. Retention time (anal. HPLC: 25–95% MeCN/H$_2$O over 5 min)=4.60 min.

To the intermediate 11 (521 mg, 0.8 mmol) dissolved in DCM, under nitrogen atmosphere, was added triethylamine (446 uL, 2.4 mmol) and then methanesulfonylchloride (186 uL, 2.4 mmol) in DCM. The mixture was stirred for 15 hrs, and then concentrated in vacuo. It was taken up in ethyl acetate, and washed with phosphoric acid, saturated sodium bicarbonate, and brine. After dried over sodium sulfate, and filtered, the organic phase was concentrated to dryness to give an intermediate sulfonate (II). ESMS ($C_{39}H_{58}N_2O_{12}S_2$): calcd. 810.34; obsd. 811.5 [M+H]$^+$. Retention time (anal. HPLC: 25–95% MeCN/H$_2$O over 5 min)=5.0 min.

To the intermediate III (6.4 g, 7.9 mmol) dissolved in THF, under nitrogen atmosphere, was added dropwise a solution of lithium triethylborohydride in TBF (1.0 M, 80 mL, 80 mmol). The mixture was stirred for 15 hrs, and concentrated. The residue was taken up in 50 mL of dichloromethane, and chilled to 0° C. prior to addition of 10 mL of TFA. The mixture was stirred for 2 hrs, concentrated in vacuo, and taken up in 75 mL of Ethyl Acetate. It was extracted with 20 mL of 1N HCl. The aqueous layer was collected, and purified by prep HPLC to afford compound 44. ESMS ($C_{27}H_{38}N_2O_2$): calcd. 422.611; obsd. 423.1 [M+H]$^+$. Retention time (anal. HPLC: 10–70% MeCN/H$_2$O over 5 min)=2.90 min.

Example 45

To a solution of the intermediate ester (I)—which was used in synthesis of compound 44—(3.43 g, 4.83 mmol) in methanol was added a solution of NaOH (1.16 g, 29 mmol) in methanol (total methanol volume was 20 mL). The mixture was stirred for 4 hrs, and concentrated under reduced pressure. The residue was dissolved in water and stirred while 6N HCl was added dropwise until precipitates were formed (pH=6). It was collected and dried under vacuum to give N-Boc derivative of compound 45. ESMS ($C_{37}H_{50}N_2O_{10}$): calcd. 682.35; obsd. 683.0 [M+H]$^+$. Retention time (anal. HPLC: 25–95% MeCN/H$_2$O over 5 min)= 4.20 min.

The N-Boc intermediate (683 mg, 1 mmol) was taken up in 10 mL of dichloromethane, and-cooled to 0° C. before addition of 7.5 mL of TFA. The mixture was stirred for 2 hrs, and concentrated in vacuo. It was taken up in 75 mL of Ethyl Acetate, and extracted with 20 mL of 1N HCl. The aqueous solution was purified by prep HPLC to afford compound 45. ESMS ($C_{27}H_{34}N_2O_6$): calcd. 482.6636; obsd. 483.3 [M+H]$^+$. Retention time (anal. HPLC: 10–70% MeCN/H$_2$O over 5 min)=2.62 min.

Example 46

A solution of the N-Boc derivative of compound 45 (683 mg, 1 mmol), HOAT (340 mg, 2.5 mmol), HATU (950 mg, 2.5 mmol), diisopropylethylamine (540 uL, 3.0 mmol), and dimethylamine (2.0 M, 1.25 mL, 2.5 mmol) in DMF was stirred for 16 hrs, and then concentrated in vacuo. It was taken up in 50 mL of dichloromethane, and cooled to 0° C., before addition of 10 mL of TFA. After stirred for 2 hrs, the mixture was concentrated under reduced pressure, and taken up in 75 mL of Ethyl Acetate. It was extracted with 20 mL of 1N HCl, and the aqueous solution was purified by prep HPLC to afford compound 46. ESMS ($C_{31}H_{44}N_4O_4$): calcd. 536.7149; obsd. 537.2 [M+H]$^+$. Retention time (anal. HPLC: 10–70% MeCN/H$_2$O over 5 min)=2.75 min.

Example 47

To a cold solution of the intermediate alcohol 11 (655 mg, 1 mmol)—used in synthesis of compound 44—in 10 mL of dichloromethane at 0° C. was added 7.5 mL of TFA. The mixture was stirred for 2 hrs, and concentrated in vacuo. The residue was taken up in 75 mL of Ethyl Acetate, and extracted with 20 mL of 1N HCl. The aqueous solution was collected, and purified by prep HPLC to afford compound 47. ESMS ($C_{27}H_{38}N_2O_4$): calcd. 454.6098; obsd. 455.1 [M+H]$^+$. Retention time (anal. HPLC: 10–70% MeCN/H$_2$O over 5 min)=2.86 min.

Example 48

To a cold solution of the intermediate alcohol II (655 mg, 1 mmol)—used in synthesis of compound 44—and methyl iodide (426 mg, 3 mmol) in THF at 0° C. was added sodium hydride (60%, 240 mg, 6 mmol). After the addition, the mixture was stirred at rt for 16 hrs, and quenched with wet THF. The mixture was partitioned between ethyl acetate and water. The organic phase was washed with saturated sodium bicarbonate, and brine. After dried over sodium sulfate, and filtered, the filtrate was concentrated under reduced pressure. The residue was taken up in 10 mL of dichloromethane, and chilled to 0° C., before treatment with 7.5 mL of TFA. The mixture was stirred for 2 hrs, then concentrated, and taken up in 75 mL of Ethyl Acetate. It was extracted with 20 mL of 1N HCl, and the aqueous solution was purified by prep HPLC to afford compound 48. ESMS ($C_{29}H_{42}N_2O_4$): calcd. 482.6636; obsd. 483.3 [M+H]$^+$. Retention time (anal. HPLC: 10–70% MeCN/H$_2$O over 5 min)=2.99 min.

Example 49

Compound 49 was prepared similarly as described in Example 1, except replacing 4,4'-methylene-bis(2,6-dimethylphenol) and the N-Boc-3-pyrrolidinol used with 4,4'-methylene-bisphenol and N-isopropyl-3-pyrrolidinol (without treatment with TFA). ESMS ($C_{27}H_{38}N_2O_2$): calcd. 422.61; obsd. 423.1 [M+H]$^+$. Retention time (anal. HPLC: 10–70% MeCN/H$_2$O over 5 min)=2.50 min.

Example 50

Compound 50 was prepared similarly as described in Example 1, except replacing 4,4'-methylene-bis(2,6-dimethylphenol) and the N-Boc-3-pyrrolidinol used with 4,4'-isopropylidene-bis(2,6-dimethylphenol) and N-methyl-3-pyrrolidinol, respectively (without treatment with TFA). ESMS ($C_{29}H_{42}N_2O_2$): calcd. 450.6648; obsd. 451.1 [M+H]$^+$. Retention time (anal. HPLC: 10–70% MeCN/H$_2$O over 5 min)=2.85 min.

Examples 51 to 58

Unless otherwise noted, compounds 51 to 58 were prepared similarly as described in Example 1, except replacing 4,4'-methylene-bis(2,6-dimethylphenol) and the N-Boc-3-pyrrolidinol used with 4,4'-isopropylidene(2-methylphenol) and the requisite alcohol.

Example 51

Compound 51 was prepared using N-(2-hydroxyethyl)morpholine (without treatment with TFA). ESMS ($C_{29}H_{42}N_2O_4$): calcd. 482.31; obsd. 483.3 [M+H]$^+$. Retention time (anal. HPLC: 2–70% MeCN/H$_2$O over 4 min)=2.860 min.

Example 52

Compound 52 was prepared using N,N-di-ethyl-5-amino-2-pentanol (without treatment with TFA). ESMS ($C_{35}H_{58}N_2O_3$): calcd. 538.45; obsd. 539.4 [M+H]$^+$. Retention time (anal. HPLC: 20–90% MeCN/H$_2$O over 4 min)=2.619 min.

Example 53

Compound 53 was prepared using N,N-di-methyl-3-amino-2,2-di-methyl-propanol (without treatment with TFA). ESMS ($C_{31}H_{50}N_2O_2$): calcd. 482.39; obsd. 483.3 [M+H]$^+$. Retention time (anal. HPLC: 2–70% MeCN/H$_2$O over 4 min)=3.472 min.

Example 54

Compound 54 was prepared using N-methyl-4-hydroxypiperidine (without treatment with TFA). ESMS ($C_{29}H_{42}N_2O_2$): calcd. 450.32; obsd. 451.3 [M+H]$^+$. Retention time (anal. HPLC: 2–70% MeCN/H$_2$O over 4 min)=2.985 min.

Example 55

Compound 55 was prepared using N-methyl-3-hydroxymethylpiperidine (without treatment with TFA). ESMS ($C_{31}H_{46}N_2O_2$): calcd. 478.36; obsd. 479.3 [M+H]$^+$. Retention time (anal. HPLC: 2–70% MeCN/H$_2$O over 4 min)=3.361 min.

Example 56

Compound 56 was prepared using N,N-di-methyl-3-amino-2-propanol (without treatment with TFA). ESMS ($C_{27}H_{42}N_2O_2$): calcd. 426.32; obsd. 427.2 [M+H]$^+$. Retention time (anal. HPLC: 2–70% MeCN/H$_2$O over 4 min) 3.103 min.

Example 57

Compound 57 was prepared using N-methyl-2-hydroxymethylpiperidine (without treatment with TFA). ESMS ($C_{31}H_{46}N_2O_2$): calcd. 478.36; obsd. 479.3 [M+H]$^+$. Retention time (anal. HPLC: 2–70% MeCN/H$_2$O over 4 min)=3.296 min.

Example 58

Compound 58 was prepared using N-methyl-3-pyrrolidinol (without treatment with TFA). ESMS ($C_{27}H_{38}N_2O_2$): calcd. 422.61; obsd. 423.1 [M+H]$^+$. Retention time (anal. HPLC: 10–70% MeCN/H$_2$O over 5 min)=2.79 min.

Example 59

Compound 59 was prepared similarly as described in Example 1, except replacing 4,4'-methylene-bis(2,6-dimethylphenol) and the N-Boc-3-pyrrolidinol used with 1,1-bis(4-hydroxyphenyl)cyclohexane and N-methyl-3-pyrrolidinol, respectively (without treatment with TFA). ESMS ($C_{28}H_{38}N_2O_2$): calcd. 434.622; obsd. 435.2 [M+H]$^+$. Retention time (anal. HPLC: 10–70% MeCN/H$_2$O over 5 min)=2.90 min.

Examples 60 to 71

Unless otherwise noted, compounds 60 to 71 were prepared similarly as described in Example 1, except replacing 4,4'-methylene-bis(2,6-dimethylphenol) and the N-Boc-3-pyrrolidinol used with 1,2-bis(3,5-dimethyl-4-hydroxyphenyl)ethane and the requisite alcohol.

Example 60

Compound 60 was prepared using N-(2-hydroxyethyl)morpholine (without treatment with TFA). ESMS ($C_{30}H_{44}N_2O_4$): calcd. 496.33; obsd. 497.2 [M+H]$^+$. Retention time (anal. DPLC: 2–70% MeCN/H$_2$O over 4 min)=2.928 mm.

Example 61

Compound 61 was prepared using N,N-di-methyl-3-amino-2-propanol (without treatment with TFA). ESMS ($C_{28}H_{44}N_2O_2$): calcd. 440.34; obsd. 441.3 [M+H]$^+$. Retention time (anal. HPLC: 2–70% MeCN/H$_2$O over 4 min)=3.037 min.

Example 62

Compound 62 was prepared using N-methyl-2-(2-hydroxyethyl)pyrrolidine (without treatment with TFA). ESMS ($C_{32}H_{48}N_2O_2$): calcd. 492.37; obsd. 493.3 [M+H]$^+$. Retention time (anal. HPLC: 2–70% MeCN/H$_2$O over 4 min)=3.357 min.

Example 63

Compound 63 was prepared using N-Boc-3-hydroxypyrrolidine. ESMS ($C_{26}H_{36}N_2O_2$): calcd. 408.58; obsd. 409.2 [M+H]$^+$. Retention time (anal. HPLC: 10–70% MeCN/H$_2$O over 5 min)=2.8 min.

Example 64

Compound 64 was prepared using N-methyl-3-hydroxypyrrolidine (without treatment with TFA). ESMS ($C_{28}H_{40}N_2O_2$): calcd. 436.64; obsd. 437.1 [M+H]$^+$. Retention time (anal. HPLC: 10–70% MeCN/H$_2$O over 5 min)=2.85 min.

Example 65

Compound 65 was prepared using N-Boc-4-hydroxypiperidine. ESMS ($C_{28}H_{40}N_2O$): calcd. 436.64; obsd. 437.1 [M+H]$^+$. Retention time (anal. HPLC: 10–70% MeCN/H$_2$O over 5 min)=2.9 min.

Example 66

Compound 66 was prepared using N-Boc-3-hydroxymethylpiperidine. ESMS ($C_{30}H_{44}N_2O_2$): calcd. 464.69; obsd. 465.3 [M+H]$^+$. Retention time (anal. HPLC: 10–70% MeCN/H$_2$O over 5 min)=3.25 min.

Example 67

Compound 67 was prepared using 4-hydroxy-N-methyl-piperidine (without treatment with TFA). ESMS ($C_{30}H_{44}N_2O$): calcd. 464.6916; obsd. 465.3 [M+H]$^+$. Retention time (anal. HPLC: 10–70% MeCN/H$_2$O over 5 min)=2.99 min.

Example 68

Compound 68 was prepared using N-methyl-piperidine-3-methanol (without treatment with TFA). ESMS ($C_{32}H_{48}N_2O$): calcd. 492.7454; obsd. 493.2 [M+H]$^+$. Retention time (anal. HPLC: 10–70% MeCN/H$_2$O over 5 min)=3.25 min.

Example 69

Compound 69 was prepared using N-methyl-2-piperidineethanol (without treatment with TFA). ESMS ($C_{32}H_{52}N_2O_2$): calcd. 520.7992; obsd. 521.4 [M+H]$^+$. Retention time (anal. HPLC: 10–70% MeCN/H$_2$O over 5 min)=3.40 mm.

Example 70

Compound 70 was prepared using N-methyl-piperidine-2-methanol (without treatment with TFA). ESMS ($C_{32}H_{48}N_2O_2$): calcd. 492.7454; obsd. 493.2 [M+H]$^+$. Retention time (anal. HPLC: 10–70% MeCN/H$_2$O over 5 min)=3.22 min.

Example 71

Compound 71 was prepared using N-(2-hydroxyethyl)-pyrrolidine (without treatment with TFA). ESMS ($C_{30}H_{44}N_2O_2$): calcd. 464.6916; obsd. 465.3 [M+H]$^+$. Retention time (anal. HPLC: 10–70% MeCN/H$_2$O over 5 min)=3.02 min.

Examples 72 to 75

Unless otherwise noted, compounds 72 to 75 were prepared similarly as described in Example 1, except replacing 4,4'-methylene-bis(2,6-dimethylphenol) and the N-Boc-3-pyrrolidinol used with 2,6-dimethyl-4-(2-hydroxy-3-methylbenzyl)phenol and the requisite alcohol.

Example 72

Compound 72 was prepared using N-methyl-3-pyrrolidinol (without treatment with TFA). ESMS ($C_{26}H_{36}N_2O_2$): calcd. 408.5841; obsd. 409.2 [M+H]$^+$ Retention time (anal. HPLC: 25–95% MeCN/H$_2$O over 5 min) 2.54 min.

Example 73

Compound 73 was prepared using N-methyl-piperidine-3-methanol (without treatment with TFA). ESMS ($C_{30}H_{44}N_2O_2$): calcd. 464.6916; obsd. 465.3 [M+H]$^+$. Retention time (anal. HPLC: 10–70% MeCN/H$_2$O over 5 min)=3.09 min.

Example 74

Compound 74 was prepared using N-methyl-4-hydroxypiperidine (without treatment with TFA). ESMS ($C_{28}H_{40}N_2O_2$): calcd. 436.6379; obsd. 437.1 [M+H]$^+$. Retention time (anal. HPLC: 10–70% MeCN/H$_2$O over 5 min)=2.89 min.

Example 75

Compound 75 was prepared using N-methyl-2-piperidineethanol (without treatment with TFA). ESMS ($C_{32}H_{42}N_2O_2$): calcd. 492.7294; obsd. 493.2 [M+H]$^+$. Retention time (anal. HPLC: 10–70% MeCN/H$_2$O over 5 min)=3.20 min.

Examples 76 to 83

Unless otherwise noted, compounds 76 to 83 were prepared similarly as described in Example 1, except replacing 4,4'-methylene-bis(2,6-dimethylphenol) and the N-Boc-3-pyrrolidinol used with 4-(2-hydroxybenzyl)phenol and the requisite alcohol.

Example 76

Compound 76 was prepared using N-methyl-3-hydroxypyrrolidine (without treatment with TFA). ESMS ($C_{23}H_{30}N_2O_2$): calcd. 366.23; obsd. 367.2 [M+H]$^+$. Retention time (anal. HPLC: 2–70% MeCN/H$_2$O over 4 min)=2.485 min.

Example 77

Compound 77 was prepared using N-(2-hydroxyethyl) morpholine (without treatment with TFA). ESMS ($C_{25}H_{34}N_2O_4$): calcd. 426.25; obsd. 427.2 [M+H]$^+$. Retention time (anal. HPLC: 2–70% MeCN/H$_2$O over 4 min)=2.466 min.

Example 78

Compound 78 was prepared using N,N-di-methyl-3-amino-2,2-di-methyl-propanol (without treatment with TFA). ESMS ($C_{27}H_{42}N_2O_2$): calcd. 426.32; obsd. 427.3 [M+H]$^+$. Retention time (anal. HPLC: 2–70% MeCN/H$_2$O over 4 min)=2.913 min.

Example 79

Compound 79 was prepared using N-methyl-4-hydroxypiperidine (without treatment with TFA). ESMS ($C_{25}H_{34}N_2O_2$): calcd. 394.26; obsd. 395.2 [M+H]$^+$. Retention time (anal. HPLC: 2–70% MeCN/H$_2$O over 4 min)=2.653 min.

Example 80

Compound 80 was prepared using N-methyl-3-hydroxymethylpiperidine (without treatment with TFA). ESMS ($C_{27}H_{38}N_2O_2$): calcd. 422.29; obsd. 423.2 [M+H]$^+$. Retention time (anal. HPLC: 2–70% MeCN/H$_2$O over 4 min)=2.856 min.

Example 81

Compound 81 was prepared using N-methyl-2-(2-hydroxyethyl)piperidine (without treatment with TFA). ESMS ($C_{29}H_{42}N_2O_2$): calcd. 450.32; obsd. 451.3 [M+H]$^+$. Retention time (anal. HPLC: 2–70% MeCN/H$_2$O over 4 min)=2.913 min.

Example 82

Compound 82 was prepared using N-methyl-2-(2-hydroxyethyl)pyrrolidine (without treatment with TFA). ESMS ($C_{27}H_{38}N_2O_2$): calcd. 422.29; obsd. 423.2 [M+H]$^+$. Retention time (anal. HPLC: 2–70% MeCN/H$_2$O over 4 min)=2.919 min.

Example 83

Compound 83 was prepared using N-methyl-2-hydroxymethylpiperidine (without treatment with TFA). ESMS ($C_{27}H_{38}N_2O_2$): calcd. 422.29; obsd. 423.3 [M+H]$^+$. Retention time (anal. HPLC: 2–70% MeCN/H$_2$O over 4 min)=2.902 min.

Examples 84 to 90

Unless otherwise noted, compounds 84 to 90 were prepared similarly as described in Example 1, except replacing 4,4'-methylene-bis(2,6-dimethylphenol) and the N-Boc-3-pyrrolidinol used with 3,3'-dihydroxydiphenylamine and the requisite alcohol, respectively.

Example 84

Compound 84 was prepared using N-methyl-3-hydroxypyrrolidine (without treatment with TFA). ESMS ($C_{22}H_{29}N_2O_3$): calcd. 367.23; obsd. 368.2 [M+H]$^+$. Retention time (anal. HPLC: 2–70% MeCN/H$_2$O over 4 min)=2.339 min.

Example 85

Compound 85 was prepared using N-(2-hydroxyethyl)morpholine (without treatment with TFA). ESMS ($C_{24}H_{33}N_3O_4$): calcd. 427.25; obsd. 428.2 [M+H]$^+$. Retention time (anal. HPLC: 2–70% MeCN/H$_2$O over 4 min)=2.280 min.

Example 86

Compound 86 was prepared using N,N-di-methyl-3-amino-2,2-di-methyl-propanol (without treatment with TFA). ESMS ($C_{26}H_{41}N_3O_2$): calcd. 427.32; obsd. 428.3 [M+H]$^+$. Retention time (anal. HPLC: 2–70% MeCN/H$_2$O over 4 min)=2.789 min.

Example 87

Compound 87 was prepared using N-methyl-4-hydroxypiperidine (without treatment with TFA). ESMS ($C_{24}H_{33}N_3O_2$): calcd. 395.26; obsd. 396.2 [M+H]$^+$. Retention time (anal. HPLC: 2–70% MeCN/H$_2$O over 4 min)=2.507 min.

Example 88

Compound 88 was prepared using N-methyl-2-(2-hydroxyethyl)piperidine (without treatment with TFA). ESMS ($C_{28}H_{41}N_3O_2$): calcd. 451.32; obsd. 452.3 [M+H]$^+$. Retention time (anal. HPLC: 2–70% MeCN/H$_2$O over 4 min)=2.784 min.

Example 89

Compound 89 was prepared using N-methyl-2-(2-hydroxyethyl)pyrrolidine (without treatment with TFA). ESMS ($C_{26}H_{37}N_3O_2$): calcd. 423.29; obsd. 424.2 [M+H]$^+$. Retention time (anal. HPLC: 2–70% MeCN/H$_2$O over 4 min)=2.780 min.

Example 90

Compound 90 was prepared using N-methyl-2-hydroxymethylpiperidine (without treatment with TFA). ESMS ($C_{26}H_{37}N_3O_2$): calcd. 423.29; obsd. 424.2 [M+H]$^+$. Retention time (anal. HPLC: 2–70% MeCN/H$_2$O over 4 min)=2.645 min.

Examples 91 to 99

Unless otherwise noted, compounds 91 to 99 were prepared similarly as described in Example 1, except replacing 4,4'-methylene-bis(2,6-dimethylphenol) and the N-Boc-3-pyrrolidinol used with 2,2'-methylene-bis(4-chlorophenol) and the requisite alcohol.

Example 91

Compound 91 was prepared using N-Boc-3-hydroxypyrrolidine. ESMS ($C_{21}H_{24}Cl_2N_2O_2$):calcd. 406.12; obsd. 407.0 [M+H]$^+$. Retention time (anal. HPLC: 10–70% MeCN/H$_2$O over 5 min)=2.836 min. $^1$H-NMR (CD$_3$OD, 299.96 MHz): δ (ppm) 1.25 (s, impurity) 2.30 (m, 4H), 3.57 (m, 8H), 3.94 (m, 2H), 5.18 (s, 2H), 6.96 (d, 2H), 7.11 (s, 2H), 7.20 (dd, 2H).

Example 92

Compound 92 was prepared using N-methyl-4-hydroxypiperidine (without treatment with TFA). ESMS ($C_{25}H_{32}Cl_2N_2O_2$): calcd. 462.18; obsd. 463.1 [M+H]$^+$. Retention time (anal. HPLC: 10–70% MeCN/H$_2$O over 5 min)=2.949 min. $^1$H-NMR (CD$_3$OD, 299.96 MHz): δ (ppm) 1.33 (m, 1H) 1.88 (m, 1H), 2.13 (s, 6H), 2.89 (m, 6H), 3.16 (t, 2H), 3.36 (m, 4H), 3.58 (m, 2H), 4.00 (d, 2H), 4.71 (m, 2H), 7.10 (m, 6H)

Example 93

Compound 93 was prepared using N-methyl-3-hydroxymethylpiperidine (without treatment with TFA). ESMS ($C_{27}H_{36}Cl_2N_2O_2$): calcd. 490.22; obsd. 491.0 [M+H]$^+$. Retention time (anal. HPLC: 10–70% MeCN/H$_2$O over 5 min)=3.197 min. $^1$H-NMR (CD$_3$OD, 299.96 MHz): δ (ppm) 1.35 (s, impurity) 1.78–2.10 (m, 6H), 2.33 (m, 2H), 2.79 (t, 2H), 2.89 (t, 2H), 2.89 (s, 6H), 3.49 (q, 4H), 3.98 (m, 6H), 6.98 (d, 2H), 7.10 (s, 2H), 7.29 (dd, 2H).

Example 94

Compound 94 was prepared using N-Boc-2-(2-hydroxyethyl)piperidine. ESMS (C$_{27}$H$_{36}$Cl$_2$N$_2$O$_2$): calcd. 490.22; obsd. 491.0 [M+H]$^+$. Retention time (anal. HPLC: 10–70% MeCN/H$_2$O over 5 min)=3.283 min. $^1$H-NMR (CD$_3$OD, 299.96 MHz): δ (ppm) 1.28 (s, impurity) 1.53 (t, 4H), 1.68 (m, 2H), 1.90 (m, 4H), 2.01 (m, 4H), 2.18 (m, 2H), 2.93 (t, 2H), 3.15 (s, 2H), 3.39 (m, 2H), 3.94 (s, 2H), 4.34 (t, 4H), 6.98 (m, 4H), 7.27 (dd, 2H).

Example 95

Compound 95 was prepared using N-methyl-3-hydroxypiperidine (without treatment with TFA). ESMS (C$_{23}$H$_{28}$Cl$_2$N$_2$O$_2$): calcd. 434.15; obsd. 434.9 [M+H]$^+$. Retention time (anal. HPLC: 10–70% MeCN/H$_2$O over 5 min)=2.846 min.

Example 96

Compound 96 was prepared using (S)-N-phthalimido-2-amino-propanol (after coupling, the phthalimide group was deprotected by treatment with hydrazine). ESMS (C$_{19}$H$_{24}$Cl$_2$N$_2$O$_2$): calcd. 382.12; obsd. 382.8 [M+H]$^+$. Retention time (anal. HPLC: 10–70% MeCN/H$_2$O over 5 min)=2.934 min. $^1$H-NMR (CD$_3$OD, 299.96 MHz): δ (ppm) 1.24(d, impurity), 1.39 (d, 6H) 3.73 (m, 2H), 4.0 6–4.31 (m, 6H), 7.10 (d, 4H), 7.31 (dd, 2H).

Example 97

Compound 97 was prepared using N,N-di-methyl-3-amino-2,2-dimethyl-propanol (without treatment with TFA). ESMS (C$_{27}$H$_{40}$Cl$_2$N$_2$O$_2$): calcd. 495.25; obsd. 495.4 [M+H]$^+$. Retention time (anal. HPLC: 10–70% MeCN/H$_2$O over 5 min)=3.260 min. $^1$H-NMR (CD$_3$OD, 299.96 MHz): δ (ppm) 1.20 (s, 12H) 2.91 (s, 12H), 3.16 (s, 4H), 3.91 (s, 4H), 4.05 (s, 2H), 7.02 (m, 4H), 7.31 (dd, 2H).

Example 98

Compound 98 was prepared using N,N-di-ethyl-3-aminopropanol (without treatment with TFA). ESMS (C$_{23}$H$_{34}$N$_2$O$_2$): calcd. 494.25; obsd. 495.4 [M+H]$^+$. Retention time (anal. HPLC: 10–70% MeCN/H$_2$O over 5 min)=3.207 min. $^1$H-NMR (CD$_3$OD, 299.96 MHz): δ (ppm) 1.28 (t, 12H), 2.18 (m, 4H), 3.23 (q, 12H), 3.96 (s, 2H), 4.13 (t, 4H), 6.99 (m, 4H), 7.28 (dd, 2H).

Example 99

Compound 99 was prepared using N-Boc-3-hydroxymethylpiperidine-ESMS (C$_{25}$H$_{32}$Cl$_2$N$_2$O$_2$): calcd. 462.18; obsd. 463.1 [M+H]$^+$. Retention time (anal. HPLC: 10–70% MeCN/H$_2$O over 5 min)=3.221 min. $^1$H-NMR (CD$_3$OD, 299.96 MHz): δ (ppm) 1.32–1.51 (m, 2H), 1.67–2.04 (m, 6H), 2.29 (m, 2H), 2.68–2.96 (m, 4H), 3.38 (m, 4H), 3.85–4.04 (m, 6H), 6.96 (d, 2H), 7.04 (d, 2H), 7.22 (dd, 2H).

Examples 100 to 109

Unless otherwise noted, compounds 100 to 109 were prepared similarly as described in Example 1, except replacing 4,4'-methylene-bis(2,6-dimethylphenol) and the N-Boc-3-pyrrolidinol used with 3,3'-ethylenedioxydiphenol and the requisite alcohol, respectively.

Example 100

Compound 100 was prepared using N-Boc-3-hydroxypyrrolidine. ESMS (C$_{22}$H$_{28}$N$_2$O$_4$): calcd. 384.20; obsd. 385.0 [M+H]$^+$. Retention time (anal. HPLC: 10–70% MeCN/H$_2$O over 5 min)=2.151 min.

Example 101

Compound 101 was prepared using N-methyl-4-hydroxypiperidine (without treatment with TFA). ESMS (C$_{26}$H$_{36}$N$_2$O$_4$): calcd. 440.27; obsd. 441.1 [M+H]$^+$. Retention time (anal. HPLC: 10–70% MeCN/H$_2$O over 5 min)= 2.402 min.

Example 102

Compound 102 was prepared using N-methyl-3-hydroxymethylpiperidine (without treatment with TFA). ESMS (C$_{28}$H$_{40}$N$_2$O$_4$): calcd. 468.30; obsd. 496.3 [M+H]$^+$. Retention time (anal. HPLC: 10–70% MeCN/H$_2$O over 5 min)=2.664 min. $^1$H-NMR (CD$_3$OD, 299.96 MHz): δ (ppm) 1.28 (s, impurity) 1.48 (m, 2H), 1.84–2.11 (m, 6H), 2.38 (m, 2H), 2.91 (s, m, 6H, 4H), 3.56 (d, 2H), 3.69 (d, 2H), 3.90 (m, 2H), 4.00 (dd, 2H), 4.33 (s, 4H), 6.57 (m, 6H), 7.22 (t, 2H)

Example 103

Compound 103 was prepared using N-Boc-2-(2-hydroxyethyl)piperidine. ESMS (C$_{28}$H$_{40}$N$_2$O$_4$): calcd. 468.30; obsd. 469.3 [M+H]$^+$. Retention time (anal. HPLC: 10–70% MeCN/H$_2$O over 5 min)=2.801 min.

Example 104

Compound 104 was prepared using N-methyl-3-hydroxypyrrolidine (without treatment with TFA). ESMS (C$_{24}$H$_{32}$N$_2$O$_4$): calcd. 412.24; obsd. 413.1 [M+H]$^+$. Retention time (anal. HPLC: 2–70% MeCN/H$_2$O over 4 min)= 2.496 min.

Example 105

Compound 105 was prepared using N-(2-hydroxyethyl) morpholine (without treatment with TFA). ESMS (C$_{26}$H$_{36}$N$_2$O$_6$): calcd. 472.26; obsd. 473.2 [M+H]$^+$. Retention time (anal. HPLC: 2–70% MeCN/H$_2$O over 4 min)= 2.647 min.

Example 106

Compound 106 was prepared using N,N-di-methyl-3-amino-2,2-di-methyl-propanol (without treatment with TFA). ESMS (C$_{28}$H$_{44}$N$_2$O$_4$): calcd. 472.33; obsd. 473.3 [M+H]$^+$. Retention time (anal. HPLC: 2–70% MeCN/H$_2$O over 4 min)=2.935 min.

Example 107

Compound 107 was prepared using N-methyl-2-(2-hydroxyethyl)piperidine (without treatment with TFA). ESMS ($C_{30}H_{44}N_2O_4$): calcd. 496.33; obsd. 497.3 [M+H]$^+$. Retention time (anal. HPLC: 2–70% MeCN/H$_2$O over 4 min)=3.046 min.

Example 108

Compound 108 was prepared using N-methyl-2-(2-hydroxyethyl)pyrrolidine (without treatment with TFA). ESMS ($C_{28}H_{40}N_2O_4$): calcd. 468.30; obsd. 469.2 [M+H]$^+$. Retention time (anal. HPLC: 2–70% MeCN/H$_2$O over 4 min)=2.819 min.

Example 109

Compound 109 was prepared using N-methyl-2-hydroxymethylpiperidine (without treatment with TFA). ESMS ($C_{28}H_{40}N_2O_4$): calcd. 468.30; obsd. 469.2 [M+H]$^+$. Retention time (anal. HPLC: 2–70% MeCN/H$_2$O over 4 min)=2.928 min.

Examples 110 to 113

Unless otherwise noted, compounds 110 to 113 were prepared similarly as described in Example 1, except replacing 4,4'-methylene-bis(2,6-dimethylphenol) and the N-Boc-3-pyrrolidinol used with 4,4'-(1,2-diethylethylene)diphenol and the requisite alcohol.

Example 110

Compound 110 was prepared using N-Boc-3-hydroxypyrrolidine. ESMS ($C_{26}H_{36}N_2O_2$): calcd. 408.28; obsd. 409.2 [M+H]$^+$. Retention time (anal. HPLC: 10–70% MeCN/H$_2$O over 5 min)=2.780 min.

Example 111

Compound 111 was prepared using N-methyl-4-hydroxypiperidine (without treatment with TFA). ESMS ($C_{30}H_{44}N_2O_2$): calcd. 464.34; obsd. 465.3 [M+H]$^+$. Retention time (anal. HPLC: 10–70% MeCN/H$_2$O over 5 min)=2.996 min. $^1$H-NMR (CD$_3$OD, 299.96 MHz): δ (ppm) 0.57 (t, 6H) 1.31 (d, 4H), 1.36 (m, 3H), 1.84–2.65 (m, 10H), 2.99 (s, 6H), 3.20 (t, 1H), 3.40 (m, 4H), 3.67 (d, 1H), 4.78 (s, 1H), 6.98 (m, 4H), 7.18 (m, 4H)

Example 112

Compound 112 was prepared using N-methyl-3-hydroxymethylpiperidine (without treatment with TFA). ESMS ($C_{32}H_{48}N_2O_2$): calcd. 492.37; obsd. 493.2 [M+H]$^+$. Retention time (anal. HPLC: 10–70% MeCN/H$_2$O over 5 min)=3.276 min. $^1$H-NMR (CD$_3$OD, 299.96 MHz): δ (ppm) 0.47 (t, 6H), 1.18–1.57 (m, 6H), 1.76–2.16 (m, 6H), 2.36 (m, 2H), 2.56 (m, 2H), 2.94 (s, 6H), 2.99 (m, 4H), 3.36 (d, 2H), 3.72 (d, 2H), 3.94 (m, 2H), 4.08 (q, 2H), 6.94 (d, 4H), 7.16 (d, 4H)

Example 113

Compound 113 was prepared using N-Boc-2-(2-hydroxyethyl)piperidine (without treatment with TFA). ESMS ($C_{32}H_{48}N_2O_2$): calcd. 492.37; obsd. 493.5 [M+H]$^+$. Retention time (anal. HPLC: 10–70% MeCN/H$_2$O over 5 min)=3.492 min.

Example 114

Compound 114 was prepared prepared similarly as described in Example 1, except replacing 4,4'-methylene-bis(2,6-dimethylphenol) and the N-Boc-3-pyrrolidinol used with 4,4-methylene-bis(2,6-dimethylaniline) and N-Boc-3-hydroxypyrrolidine, respectively. ESMS ($C_{25}H_{36}Cl_2N_4$): calcd. 392.6; obsd. 393.1 [M+H]$^+$. Retention time (anal. HPLC: 10–70% MeCN/H$_2$O over 4 min)=2.3 min.

Examples 115 to 124

Unless otherwise noted, compounds 115 to 124 were prepared similarly as described in Example 1, except replacing 4,4'-methylene-bis(2,6-dimethylphenol) and the N-Boc-3-pyrrolidinol used with 4,4'-methylene-bis(2-chlorophenol) and the requisite alcohol, respectively.

Example 115

Compound 115 was prepared using N-(2-hydroxyethyl)morpholine (without treatment with TFA). ESMS ($C_{25}H_{32}Cl_2N_2O_4$): calcd. 494.17; obsd. 495.1 [M+H]$^+$. Retention time (anal. HPLC: 2–70% MeCN/H$_2$O over 4 min)=2.894 min.

Example 116

Compound 116 was prepared using N,N-di-ethyl-5-amino-2-pentanol (without treatment with TFA). ESMS ($C_{31}H_{48}Cl_2N_2O_2$): calcd. 550.31; obsd. 551.3 [M+H]$^+$. Retention time (anal. HPLC: 2–70% MeCN/H$_2$O over 4 min)=3.357 min.

Example 117

Compound 117 was prepared using N,N-di-methyl-3-amino-2,2-di-methyl-propanol (without treatment with TFA). ESMS ($C_{27}H_{40}Cl_2N_2O_2$): calcd. 494.25; obsd. 495.2 [M+H]$^+$. Retention time (anal. HPLC: 2–70% MeCN/H$_2$O over 4 min)=3.116 min.

Example 118

Compound 118 was prepared using N-methyl-4-hydroxypiperidine (without treatment with TFA). ESMS ($C_{25}H_{32}Cl_2N_2O_2$): calcd. 462.18; obsd. 463.1 [M+H]$^+$. Retention time (anal. HPLC: 2–70% MeCN/H$_2$O over 4 min)=2.865 min.

Example 119

Compound 119 was prepared using N,N-di-methyl-3-amino-2-propanol (without treatment with TFA). ESMS ($C_{23}H_{32}Cl_2N_2O_2$): calcd. 438.18; obsd. 439.1 [M+H]$^+$. Retention time (anal. HPLC: 2–70% MeCN/H$_2$O over 4 min)=2.832 min.

Example 120

Compound 120 was prepared using N-methyl-2-(2-hydroxyethyl)piperidine (without treatment with TFA). ESMS ($C_{29}H_{40}Cl_2N_2O_2$): calcd. 518.25; obsd. 5519.2 $[M+H]^+$. Retention time (anal. HPLC: 2–70% MeCN/$H_2O$ over 4 min)=3.304 min.

Example 121

Compound 121 was prepared using N-methyl-2-(2-hydroxyethyl)pyrrolidine (without treatment with TFA). ESMS ($C_{27}H_{36}Cl_2N_2O_2$): 5 calcd. 490.22; obsd. 491.1 $[M+H]^+$. Retention time (anal. HPLC: 2–70% MeCN/$H_2O$ over 4 min)=3.127 min.

Example 122

Compound 122 was prepared using N-methyl-2-hydroxymethylpipenidine (without treatment with TFA). ESMS ($C_{27}H_{36}Cl_2N_2O_2$): calcd. 490.22; obsd. 491.1 $[M+H]^+$. Retention time (anal. HPLC: 20–90% MeCN/$H_2O$ over 4 min)=2.037 min.

Example 123

Compound 123 was prepared using N-methyl-3-pyrrolidinol (without treatment with TFA). ESMS ($C_{23}H_{28}Cl_2N_2O_2$): calcd. 435.393; obsd. 436.0 $[M+H]^+$. Retention time (anal. HPLC: 10–70% MeCN/$H_2O$ over 5 min)=2.49 min.

Example 124

Compound 124 was prepared using N-Boc-3-pyrrolidinol. ESMS ($C_{21}H_{24}Cl_2N_2O_2$): calcd. 407.3392; obsd. 408.0 $[M+H]^+$. Retention time (anal. HPLC: 10–70% MeCN/$H_2O$ over 5 min)=2.51 min.

Examples 125 to 126

Unless otherwise noted, compounds 125 to 126 were prepared similarly as described in Example 1, except replacing 4,4'-methylene-bis(2, 6-dimethylphenol) and the N-Boc-3-pyrrolidinol used with 4,4'-methylene-bis(2-methylphenol) and the requisite alcohol.

Example 125

Compound 125 was prepared using N-methyl-3-pyrrolidinol (without treatment with TFA). ESMS ($C_{25}H_{34}N_2O_2$): calcd. 394.5572; obsd. 394.9 $[M+H]^+$. Retention time (anal. HPLC: 10–70% MeCN/$H_2O$ over 5 min) 2.60 min.

Example 126

Compound 126 was prepared using N-Boc-3-pyrrolidinol. ESMS ($C_{23}H_{30}N_2O_2$): calcd. 366.5035; obsd. 367.0 $[M+H]^+$. Retention time (anal. HPLC: 10–70% MeCN/$H_2O$ over 5 min)=2.48 min.

Examples 127 to 134

Unless otherwise noted, compounds 127 to 134 were prepared similarly as described in Example 1, except replacing 4,4'-methylene-bis(2,6-dimethylphenol) and the N-Doc-3-pyrrolidinol used with 2,2'-methylene-bis(4-methylphenol) and the requisite alcohol.

Example 127

Compound 127 was prepared using N-methyl-3-hydroxypyrrolidine (without treatment with TFA). ESMS ($C_{25}H_{34}N_2O_2$): calcd. 394.26; obsd. 395.2 $[M+H]^+$. Retention time (anal. HPLC: 2–70% MeCN/$H_2O$ over 4 min)=2.733 min.

Example 128

Compound 128 was prepared using N-(2-hydroxyethyl)morpholine (without treatment with TFA). ESMS ($C_{27}H_{38}N_2O_4$): calcd. 454.28; obsd. 455.2 $[M+H]^+$. Retention time (anal. HPLC: 2–70% MeCN/$H_2O$ over 4 min)=2.739 min.

Example 129

Compound 129 was prepared using N,N-di-methyl-3-amino-2,2-di-methyl-propanol (without treatment with TFA). ESMS ($C_{29}H_{46}N_2O_2$): calcd. 454.36; obsd. 455.3 $[M+H]^+$. Retention time (anal. HPLC: 2–70% MeCN/$H_2O$ over 4 min)=3.097 min.

Example 130

Compound 130 was prepared using N-methyl-4-hydroxypiperidine (without treatment with TFA). ESMS ($C_{27}H_{38}N_2O_2$): calcd. 422.29; obsd. 423.2 $[M+H]^+$. Retention time (anal. HPLC: 2–70% MeCN/$H_2O$ over 4 min)=2.867 min.

Example 131

Compound 131 was prepared using N,N-di-methyl-3-amino-2-propanol (without treatment with TEFA). ESMS ($C_{25}H_{38}N_2O_2$): calcd. 398.29; obsd. 399.2 $[M+H]^+$. Retention time (anal. HPLC: 2–70% MeCN/$H_2O$ over 4 min)=2.813 min.

Example 132

Compound 132 was prepared using N-methyl-2-(2-hydroxyethyl)piperidine (without treatment with TFA). ESMS ($C_{31}H_{46}N_2O_2$): calcd. 478.36; obsd. 479.3 $[M+H]^+$. Retention time (anal. HPLC: 2–70% MeCN/$H_2O$ over 4 min)=3.164 min.

Example 133

Compound 133 was prepared using N-methyl-2-(2-hydroxyethyl)pyrrolidine (without treatment with TFA). ESMS ($C_{29}H_{42}N_2O_2$): calcd. 450.32; obsd. 451.3 $[M+H]^+$. Retention time (anal. HPLC: 2–70% MeCN/$H_2O$ over 4 min)=3.011 min.

Example 134

Compound 134 was prepared using N-methyl-2-hydroxymethylpiperidine (without treatment with TFA). ESMS ($C_{29}H_{42}N_2O_2$): calcd. 450.32; obsd. 451.2 $[M+H]^+$. Retention time (anal. HPLC: 2–70% MeCN/$H_2O$ over 4 min)=3.173 min.

Examples 135 to 143

Unless otherwise noted, compounds 135 to 143 were prepared similarly as described in Example 1, except replacing 4,4'-methylene-bis(2,6-dimethylphenol) and the N-Boc-3-pyrrolidinol used with 2,2'-dihydroxy-diphenyl ether and the requisite alcohol.

Example 135

Compound 135 was prepared using N-methyl-3-hydroxypyrrolidine (without treatment with TFA). ESMS ($C_{22}H_{28}N_2O_3$): calcd. 368.21; obsd. 369.1 [M+H]$^+$. Retention time (anal. HPLC: 2–70% MeCN/H$_2$O over 4 min)=2.302 min.

Example 136

Compound 136 was prepared using N-(2-hydroxyethyl)morpholine (without treatment with TFA). ESMS ($C_{24}H_{32}N_2O_5$): calcd. 428.23; obsd. 429.2 [M+H]$^+$. Retention time (anal. HPLC: 2–70% MeCN/H$_2$O over 4 min)=2.270 min.

Example 137

Compound 137 was prepared using N,N-di-methyl-3-amino-2, 2-di-methyl-propanol (without treatment with TFA). ESMS ($C_{26}H_{40}N_2O_3$): calcd. 428.30; obsd. 429.2 [M+H]$^+$. Retention time (anal. HPLC: 2–70% MeCN/H$_2$O over 4 min)=2.664 min.

Example 138

Compound 138 was prepared using N-methyl-4-hydroxypiperidine (without treatment with TFA). ESMS ($C_{24}H_{32}N_2O_3$): calcd. 396.24; obsd. 397.2 [M+H]$^+$. Retention time (anal. HPLC: 2–70% MeCN/H$_2$O over 4 min)=2.460 min.

Example 139

Compound 139 was prepared using N-methyl-3-hydroxymethylpiperidine (without treatment with TFA). ESMS ($C_{26}H_{36}N_2O_3$): calcd. 424.27; obsd. 425.2 [M+H]$^+$. Retention time (anal. HPLC: 2–70% MeCN/H$_2$O over 4 min)=2.785 min.

Example 140

Compound 140 was prepared using N,N-di-methyl-3-amino-2-propanol (without treatment with TFA). ESMS ($C_{22}H_{32}N_2O_3$): calcd. 372.24; obsd. 373.2 [M+H]$^+$. Retention time (anal. HPLC: 2–70% MeCN/H$_2$O over 4 min)=2.483 min.

Example 141

Compound 141 was prepared using N-methyl-2-(2-hydroxyethyl)piperidine (without treatment with TFA). ESMS ($C_{28}H_{40}N_2O_3$): calcd. 452.30; obsd. 453.3 [M+H]$^+$. Retention time (anal. HPLC: 2–70% MeCN/H$_2$O over 4 min)=2.836 min.

Example 142

Compound 142 was prepared using N-methyl-2-(2-hydroxyethyl)pyrrolidine (without treatment with TFA). ESMS ($C_{26}H_{36}N_2O_3$): calcd. 424.27; obsd. 425.2 [M+H]$^+$. Retention time (anal. HPLC: 2–70% MeCN/H$_2$O over 4 min)=2.573 min.

Example 143

Compound 143 was prepared using N-methyl-2-hydroxymethylpiperidine (without treatment with TFA). ESMS ($C_{26}H_{36}N_2O_3$): calcd. 424.27; obsd. 425.2 [M+H]$^+$. Retention time (anal. HPLC: 2–70% MeCN/H$_2$O over 4 min)=2.711 min.

Examples 144 to 151

Unless otherwise noted, compounds 144 to 151 were prepared similarly as described in Example 1, except replacing 4,4'-methylene-bis(2,6-dimethylphenol) and the N-Boc-3-pyrrolidinol used with 4,4'-dihydroxy-diphenyl ether and the requisite alcohol.

Example 144

Compound 144 was prepared using N-methyl-3-hydroxypyrrolidine (without treatment with TFA). ESMS ($C_{22}H_{28}N_2O_3$): calcd. 368.21; obsd. 369.1 [M+H]$^+$. Retention time (anal. HPLC: 2–70% MeCN/H$_2$O over 4 min)=2.333 min.

Example 145

Compound 145 was prepared using N-(2-hydroxyethyl)morpholine (without treatment with TFA). ESMS ($C_{24}H_{32}N_2O_5$): calcd. 428.23; obsd. 429.2 [M+H]$^+$. Retention time (anal. HPLC: 2–70% MeCN/H$_2$O over 4 min)=2.291 min.

Example 146

Compound 146 was prepared using N,N-di-methyl-3-amino-2,2-di-methyl-propanol (without treatment with TFA). ESMS ($C_{26}H_{40}N_2O_3$): calcd. 428.30; obsd. 429.3 [M+H]$^+$. Retention time (anal. HPLC: 2–70% MeCN/H$_2$O over 4 min)=2.826 min.

Example 147

Compound 147 was prepared using N-methyl-4-hydroxypiperidine (without treatment with TFA). ESMS ($C_{24}H_{32}N_2O_3$): calcd. 396.24; obsd. 397.2 [M+H]$^+$. Retention time (anal. HPLC: 2–70% MeCN/H$_2$O over 4 min)=2.513 min.

Example 148

Compound 148 was prepared using N-methyl-3-hydroxymethylpiperidine (without treatment with TFA). ESMS ($C_{26}H_{36}N_2O_3$): calcd. 424.27; obsd. 425.2 [M+H]$^+$. Retention time (anal. HPLC: 2–70% MeCN/H$_2$O over 4 min)=2.905 min.

Example 149

Compound 149 was prepared using N-methyl-2-(2-hydroxyethyl)piperidine (without treatment with TFA). ESMS ($C_{28}H_{40}N_2O_3$): calcd. 452.30; obsd. 453.3 [M+H]$^+$. Retention time (anal. HPLC: 2–70% MeCN/H$_2$O over 4 min)=2.821 min.

Example 150

Compound 150 was prepared using N-methyl-2-(2-hydroxyethyl)pyrrolidine (without treatment with TFA). ESMS ($C_{26}H_{36}N_2O_3$): calcd. 424.27; obsd. 425.2 $[M+H]^+$. Retention time (anal. HPLC: 2–70% MeCN/$H_2O$ over 4 min)=2.780 min.

Example 151

Compound 151 was prepared using N-methyl-2-hydroxymethylpiperidine (without treatment with TFA). ESMS ($C_{26}H_{36}N_2O_3$): calcd. 424.27; obsd. 425.2 $[M+H]^+$. Retention time (anal. HPLC: 2–70% MeCN/$H_2O$ over 4 min)=2.749 min.

Examples 152 to 154

Unless otherwise noted, compounds 152 to 154 were prepared similarly as described in Example 1, except replacing 4,4'-methylene-bis(2,6-dimethylphenol) and the N-Boc-3-pyrrolidinol used with 2,2'-methylene-bis(6-methylphenol), and the requisite alcohol, respectively.

Example 152

Compound 152 was prepared using N-methyl-4-hydroxypiperidine (without treatment with TFA). ESMS ($C_{27}H_{38}N_2O_2$): calcd. 422.611; obsd. 423.1 $[M+H]^+$. Retention time (anal. HPLC: 10–70% MeCN/$H_2O$ over 5 min)=2.60 min.

Example 153

Compound 153 was prepared using N-methyl-3-pyrrolidinol (without treatment with TFA). ESMS ($C_{25}H_{34}N_2O_2$): calcd. 394.5572; obsd. 395.1 $[M+H]^+$. Retention time (anal. HPLC: 10–70% MeCN/$H_2O$ over 5 min)=2.71 min.

Example 154

Compound 154 was prepared using N-methyl-2-piperidineethanol (without treatment with TFA). ESMS ($C_{31}H_{46}N_2O_2$): calcd. 478.7185; obsd. 479.3 $[M+H]^+$. Retention time (anal. HPLC: 10–70% MeCN/$H_2O$ over 5 min)=3.21 min.

Example 155

Determination of Sodium Channel Activity

Measurement of Sodium Channel Activity in Neonatal Rat Cerebellar Granule Neurons.

(a) Primary culture of rat cerebellar granule neurons:

Primary cultures of cerebellar granule neurons were prepared as described previously (Gallo et al., 1990; *J. Neurochem:* 54, 1619–25). Briefly, cerebella were dissected from 7 to 8 day-old Sprague-Dawley rats and cut into pieces using a McIlwain tissue chopper. Tissue pieces were incubated with 0.025% trypsin in Hanks Balanced Salt Solution (HBSS) for 10 min at 37° C. Following enzyme treatment, the tissue pieces were resuspended in HBSS buffer containing 2.8 mg/ml soybean trypsin inhibitor and 0.006% DNase and dissociated mechanically by trituration with a fire-polished glass pipette. The cell suspension then was centrifuged at 1000 g for 5 min, the supernatant discarded and the pellet resuspended in DMEM/F12 supplemented with 10% fetal bovine serum, 30 mM glucose, 25 mM KCl, 1 mM glutamine, 1 mM sodium pyruvate, N2 supplement and penicillin (20 U/ml)-streptomycin (20 mg/ml)-amphotericin B. Cells were plated in 96-well poly-D-lysine-coated black wall-clear bottom culture plates at a concentration of 1–2×$10^5$ cells/well. Cells were maintained at 37° C. in an atmosphere containing 5% $CO_2$. After 18–24 h, cytosine arabinoside (10 mM final concentration) was added, to inhibit replication of non-neuronal cells. All experiments were performed using cultures maintained for 4–6 days in vitro (4–6 DIC).

2. Analysis of sodium channel activity in rat cerebellar granule neurons using the fluorescent imaging plate reader (FLIPR):

To measure sodium channel activity, veratridine-evoked increases in intracellular $Ca^{2+}$($[Ca^{2+}]_i$) in fluo-4/AM loaded cerebellar granule neurons were monitored, in real-time, using the FLIPR (Molecular Devices, Sunnyvale, Calif.). Cerebellar granule neurons, at 4–6 DIC, were incubated with 4 mM fluo-4/AM in HBSS buffer containing 2.5 mM probenecid and 0.04% pluronic acid for 45 min at 37° C. The neurons then were washed three times with HBSS containing 2.5 mM probenecid (FLIPR buffer). The plates were transferred to the FLIPR and the cells incubated for 5 min in FLIPR buffer, in the absence (control) or presence of antagonist, prior to addition of veratridine (40 μM). Cell fluorescence ($\lambda_{Ex}$=488 nm; $1_{Em}\geq$510 nm) was monitored both before and after the addition of veratridine. Peak fluorescence intensity, after veratridine addition, was determined using the FLIPR software. Curve fitting and parameter estimation ($pIC_{50}$) were performed using GraphPad. Stock solutions (10 mM) of compounds were made in 100% DMSO.

Compounds of the invention corresponding to Examples 27, 29–33, 35–39, 41, 42, 44, 46, 48, 50–59, 61, 62, 64–70, 72–74, 76–83, 86–94, 96, 97, 101–110, 112, 115–134, 137, 139, 141, 143, 146, 148–150, and 152–154 have an $IC_{50}$ value of less than 100 μM in this assay. Compounds of Examples 45, 47, 60, 84, 85, 100, 111, 135, 136, 138, 140, 142, 144, 145, 147, and 151 exhibited less than 50% inhibition of the control response at 100 μM, the highest concentration tested. No $IC_{50}$ value was obtained for these compounds although they are expected to demonstrate sodium channel activity at higher concentrations. Compounds of Examples 28, 34, 40, 43, 49, 63, 71, 75, 95, 98, 99, 113, and 114 were not tested. In general, compounds of the invention corresponding to Examples 1–26 have an $IC_{50}$ value of less than 100 μM in a rat cerebellar granule neuron assay.

Example 156

In Vivo Pain Model

The ability of an agent or a combination of agents to treat pain can be determined using known pharmacological models (for example see Kim, S. H. and Chung, J. M., *Pain,* 1992, 50, 355–363), or using models that are similar to known models.

Male Sprague-Dawley rats (120–180 g, Harlan, Indianapolis, Ind.) are pre-screened to determine their baseline 50% withdrawal threshold using a set of von Frey filaments. The 50% withdrawal threshold for mechanical stimulation to the hind paw is determined by the up-down method described by Dixon W. J., *Ann. Rev. Pharmacol. Toxicol.,* 1980, 20, 441–462.

Briefly, 8 von Frey filaments with approximately equal logarithmic incremental (0.22) bending forces are chosen (von Frey numbers: 3.65, 3.87, 4.10, 4.31, 4.52, 4.74, 4.92, and 5.16; equivalent to: 0.45, 0.74, 1.26, 2.04, 3.31, 5.50, 8.32, and 14.45 g). A von Frey filament is applied perpendicularly to the plantar surface with sufficient force to bend it slightly and held for 3–5 seconds. An abrupt withdrawal of the foot during stimulation or immediately after the removal of stimulus is considered a positive response.

Whenever there is a positive or negative response, the next weaker or stronger filament is applied, respectively. The test is continued until six stimuli after the first change in response has been obtained. The pattern of positive and negative responses is converted into a 50% threshold value using the following formula: 50% threshold=10^(X+kd)/10^4, where X=the value of the final von Frey filament used (in log units), k=the tabular value for the pattern of positive/negative responses [obtained from Dixon], and d=the mean difference between stimuli in log units (0.22). In the cases where continuous positive or negative responses are observed all the way out to the end of the stimulus spectrum, values of 0.3 g or 15.0 g are assigned, respectively. For $ED_{50}$ calculations, a linear regression is determined for responses one either side of the 50% reversal and then an approximation is determined based upon the value which intersects the 50% point.

After pre-screening, rats which display a 50% withdrawal threshold greater than 8 g are acceptable for surgery. The spinal nerve ligation (SNL) surgery is carried out as follows. Rats are anesthetized with inhaled Isoflurance and the left L5 and L6 spinal nerves are tightly ligated with 6–0 silk thread. Postoperatively, rats are placed under a heat lamp until motor function returns and then single-housed. At 5–7 days post surgery, rats are re-tested to determine their post-surgery 50% withdrawal threshold. Rats which consistently display (2 or more days) a 50% withdrawal threshold less than 4.5 g are considered acceptable for compound investigation.

Experimental studies typically involve one or more therapeutic compounds, a standard (control), and a vehicle group. Compounds are formulated in saline for injection and pH adjusted with dilute sodium hydroxide. Groups sizes are normally 5 or 6 rats. For routine screening of compounds, a single dose is used (normally 30 mg/kg) and the compound is administered intraperitoneally (typically 2–4 ml/kg). At 1, 3, and 6 hours post administration, the 50% withdrawal threshold is determined by an investigator who is blinded to the treatment groups. If at 6 hours, some prolonged activity is present, i.e., 50% withdrawal thresholds greater than 8 g, then later timepoints may be attempted (normally at 12 and 24 hours). Compounds can also be administered orally to determine oral activity.

Compounds which show moderate activity in the screening studies are re-tested over a range of doses in order to construct a dose response curve and generate an $ED_{50}$. The $ED_{50}$ values are used to compare compound potencies. The compounds of this invention tested in this model were effective for treating pain.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula XX:

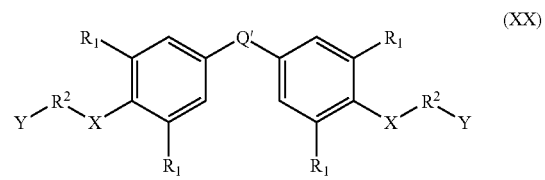

wherein
Q' is methylene;
each X is independently —O— or —NR—;
each $R^1$ is independently methyl or chloro;
each $R^2$ is independently 1,2-ethylene, 1,3-propylene, (2R)-2-(methyl)ethane-1,2-diyl, (2S)-2-(methyl) ethane-1,2-diyl, 1-(methyl)butane-1,4-diyl, 1-(methyl) ethane-1,2-diyl, or 2,2-(dimethyl)propane-1,3-diyl;
each Y is —NH$_2$;
or a pharmaceutically-acceptable salt thereof.

2. The compound of claim 1, which is any one of compounds 27, and 28:

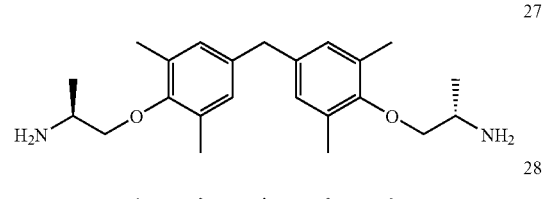

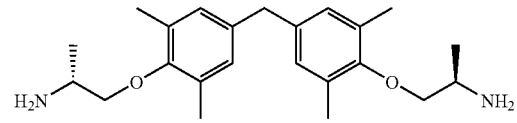

or a pharmaceutically acceptable salt thereof.

3. A pharmaceutical composition comprising a therapeutically effective amount of a compound as described in claim 1 and a pharmaceutically acceptable carrier.

4. A method of treating a disease or condition associated with sodium channel activity in a mammal, comprising administering to the mammal, a therapeutically effective amount of a pharmaceutical composition comprising a compound as described in claim 1 and a pharmaceutically acceptable carrier.

5. The method of claim 4 wherein the disease or condition is neuropathic pain.

* * * * *

UNITED STATES PATENT AND TRADEMARK OFFICE
CERTIFICATE OF CORRECTION

| | | |
|---|---|---|
| PATENT NO. | : 7,183,323 B2 | Page 1 of 1 |
| APPLICATION NO. | : 10/824738 | |
| DATED | : February 27, 2007 | |
| INVENTOR(S) | : Chinn et al. | |

It is certified that error appears in the above-identified patent and that said Letters Patent is hereby corrected as shown below:

At Column 96
line 24, "-NR-" should read -- -NH- --.

Signed and Sealed this

Thirty-first Day of July, 2007

JON W. DUDAS
*Director of the United States Patent and Trademark Office*